US010233459B2

(12) United States Patent
Lu et al.

(10) Patent No.: US 10,233,459 B2
(45) Date of Patent: Mar. 19, 2019

(54) PLANTS HAVING ALTERED AGRONOMIC CHARACTERISTICS UNDER NITROGEN LIMITING CONDITIONS AND RELATED CONSTRUCTS AND METHODS INVOLVING LOW NITROGEN TOLERANCE GENES

(71) Applicant: PIONEER OVERSEAS CORPORATION, Johnston, IA (US)

(72) Inventors: Guihua Lu, Beijing (CN); Yang Gao, Beijing (CN); Cong Li, Beijing (CN); Junhua Liu, Beijing (CN); Guanfan Mao, Beijing (CN); Wei Wang, Beijing (CN); Xiping Wang, Beijing (CN); Changgui Wang, Beijing (CN)

(73) Assignee: PIONEER OVERSEAS CORPORATION

( * ) Notice: Subject to any disclaimer, the term of this patent is extended or adjusted under 35 U.S.C. 154(b) by 0 days.

(21) Appl. No.: 15/318,062

(22) PCT Filed: Jul. 2, 2015

(86) PCT No.: PCT/CN2015/083236
§ 371 (c)(1),
(2) Date: Dec. 12, 2016

(87) PCT Pub. No.: WO2016/000646
PCT Pub. Date: Jan. 7, 2016

(65) Prior Publication Data

US 2017/0130242 A1 May 11, 2017

(30) Foreign Application Priority Data

Jul. 3, 2014 (WO) ................ PCT/CN2014/081606

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8261* (2013.01); *C12N 15/8271* (2013.01)

(58) Field of Classification Search
CPC ........................ C12N 15/8261; C12N 15/8271
See application file for complete search history.

(56) References Cited

U.S. PATENT DOCUMENTS

2004/0214272 A1* 10/2004 La Rosa ................ C07H 21/04 435/69.1
2011/0039263 A1 2/2011 Aukerman et al.

FOREIGN PATENT DOCUMENTS

| | | |
|---|---|---|
| CN | 101918560 | 12/2010 |
| CN | 102105590 | 6/2011 |
| CN | 102203263 | 9/2011 |
| CN | 102282261 | 12/2011 |
| CN | 102365365 | 2/2012 |

OTHER PUBLICATIONS

GenBank accession No. NP_001067495 (Year: 2010).*
International Search Report PCT /CN205/083236 dated Oct. 10, 2015.
Yongshen Wu et al. Low-nitrogen stress tolerance and nitrogen agronomic efficiency among maize inbreds: comparison of multiple indices and evaluation of genetic variation Euphytica, vol. vol180, Mar. 16, 2011 (Mar. 16, 2011), ISSN: pp. 281-290.
GenBank accession No. NM_001074027.1 GenBank, Jun. 8, 2010 (Jun. 8, 2010).
GenBank accession No. HV092857 GenBank, Jul. 15, 2011 (Jul. 15, 2011).
GenBank accession No. AK103177 GenBank, Dec. 4, 2008 (Dec. 4, 2008).
GenBank accession No. ABA92131 GenBank, May 5, 2011 (May 5, 2011).
GenBank accession No. NP_001067495 GenBank, Jun. 8, 2010 (Jun. 8, 2010).
GenBank accession No. BAD61690 GenBank, Feb. 16, 2008 (Feb. 16, 2008).

* cited by examiner

*Primary Examiner* — Lee A Visone

(57) ABSTRACT

Isolated polynucleotides and polypeptides, and recombinant DNA constructs useful for conferring improved nitrogen use efficiency and/or drought stress tolerance; compositions (such as plants or seeds) comprising these recombinant DNA constructs; and methods utilizing these recombinant DNA constructs are disclosed. The recombinant DNA constructs comprise a polynucleotide operably linked to a promoter that is functional in a plant, wherein said polynucleotides encode abiotic stress tolerance polypeptides.

4 Claims, 3 Drawing Sheets

Specification includes a Sequence Listing.

SEQUENCE LISTING

```
<160> NUMBER OF SEQ ID NOS: 27

<210> SEQ ID NO 1
<211> LENGTH: 10952
<212> TYPE: DNA
<213> ORGANISM: Artificial Sequence
<220> FEATURE:
<223> OTHER INFORMATION: vector DP0005

<400> SEQUENCE: 1

gaattctcta gtcccgatct agtaacatag atgacaccgc gcgcgataat ttatcctagt     60

ttgcgcgcta tattttgttt tctatcgcgt attaaatgta taattgcggg actctaatca    120

taaaaaccca tctcataaat aacgtcatgc attacatgtt aattattaca tgcttaacgt    180

aattcaacag aaattatatg ataatcatcg caagaccggc aacaggattc aatcttaaga    240

aacgcggccg cttcagttgt ggcccagctt ggaggtcgac tcgcgaggat cctctagtcc    300

cgatctagta acatagatga caccgcgcgc gataatttat cctagtttgc gcgctatatt    360

ttgttttcta tcgcgtatta aatgtataat tgcgggactc taatcataaa aacccatctc    420

ataaataacg tcatgcatta catgttaatt attacatgct taacgtaatt caacagaaat    480

tatatgataa tcatcgcaag accggcaaca ggattcaatc ttaagaaacg cggccgcttc    540

agttgtggcc cagcttggag gggcggcgt cgcagtagcg gcccacggcg gcctcgtact    600

gcttgtagca cttgcccttc tccacctcct ccaggatctc gatgcggtgg tcctcgaagt    660

ggaagccggg catcttcagg gcggaggcgg gcttcttgga gcggtaggtg gtgtgcaggt    720

ggcaggtcag gtggcgaccg ccggggcact ccagggccat cagggactgg ccgcgcagca    780

cgccgtccac ctcgtacacg atctcggtgg agggctccca gcggccggcc ttgttctgca    840
```

```
tcacggggcc gtcggcgggg aagttgttgc ccaggatctt caccttgtac accaggcagt    900
cgccgtccag ggaggtgtcc tggtgggcgg tcaggaagcc gccgtcctcg taggtggtgg    960
tgcgctccca ggtgaagccc tcggggaggg actgcttgaa gtagtcgggg atgccggaca   1020
cgtacttgat gaaggccttg gagccgtaca tgcaggaggt ggacaggatg tggaaggcga   1080
agggcagggg gccgccctcg atcacctcga tcttcatctc ctgggtgccc tccagggggt   1140
tgccctcgcc cttgccggtg cacttgaagt agtggccgtt cacggtgccc tcgatggtgg   1200
tcctgaaggg catggtcttc ttcagcaaag aggccatggt ggcgaccggt accagatctc   1260
tgcagagaga tagatttgta gagagagact ggtgatttca gcgtgtcctc tccaaatgaa   1320
atgaacttcc ttatatagag gaagggtctt gcgaaggata gtgggattgt gcgtcatccc   1380
ttacgtcagt ggagatatca catcaatcca cttgctttga agacgtggtt ggaacgtctt   1440
ctttttccac gatgctcctc gtgggtgggg gtccatcttt gggaccactg tcggcagagg   1500
catcttgaac gatagccttt cctttatcgc aatgatggca tttgtaggtg ccaccttcct   1560
tttctactgt ccttttgatg aagtgacaga tagctgggca atggaatccg aggaggtttc   1620
ccgatattac cctttgttga aaagtctcaa tagccctttg gtcttctgag actgtatctt   1680
tgatattctt ggagtagacg agagtgtcgt gctccaccat gttcacatca atccacttgc   1740
tttgaagacg tggttggaac gtcttctttt tccacgatgc tcctcgtggg tgggggtcca   1800
tctttgggac cactgtcggc agaggcatct tgaacgatag cctttccttt atcgcaatga   1860
tggcatttgt aggtgccacc ttccttttct actgtccttt tgatgaagtg acagatagct   1920
gggcaatgga atccgaggag gtttcccgat attacccttt gttgaaaagt ctcaatagcc   1980
ctttggtctt ctgagactgt atctttgata ttcttggagt agacgagagt gtcgtgctcc   2040
accatgttgc caagctgctc taagcttggc actggccgtc gttttacaac gtcgtgactg   2100
ggaaaaccct ggcgttaccc aacttaatcg ccttgcagca catccccctt tcgccagctg   2160
gcgtaatagc gaagaggccc gcaccgatcg cccttcccaa cagttgcgca gcctgaatgg   2220
cgaatgctag agcagcttga gcttggatca gattgtcgtt actatcagtg tttgacagga   2280
tatattggcg ggtaaaccta agagaaaaga gcgtttatta gaataacgga tatttaaaag   2340
ggcgtgaaaa ggtttatccg ttcgtccatt tgtatgtgca tgccaaccac agggttcccc   2400
tcgggatcaa agtactttga tccaacccct ccgctgctat agtgcagtcg gcttctgacg   2460
ttcagtgcag ccgtcttctg aaaacgacat gtcgcacaag tcctaagtta cgcgacaggc   2520
tgccgccctg cccttttcct ggcgttttct tgtcgcgtgt tttagtcgca taaagtagaa   2580
tacttgcgac tagaaccgga gacattacgc catgaacaag agcgccgccg ctggcctgct   2640
gggctatgcc cgcgtcagca ccgacgacca ggacttgacc aaccaacggg ccgaactgca   2700
cgcggccggc tgcaccaagc tgttttccga gaagatcacc ggcaccaggc gcgaccgccc   2760
ggagctggcc aggatgcttg accacctacg ccctggcgac gttgtgacag tgaccaggct   2820
agaccgcctg gcccgcagca cccgcgacct actggacatt gccgagcgca tccaggaggc   2880
cggcgcgggc ctgcgtagcc tggcagagcc gtgggccgac accaccacgc cggccggccg   2940
catggtgttg accgtgttcg ccggcattgc cgagttcgag cgttccctaa tcatcgaccg   3000
cacccggagc gggcgcgagg ccgccaaggc ccgaggcgtg aagtttggcc cccgccctac   3060
cctcaccccg gcacagatcg cgcacgcccg cgagctgatc gaccaggaag gccgcaccgt   3120
gaaagaggcg gctgcactgc ttggcgtgca tcgctcgacc ctgtaccgcg cacttgagcg   3180
```

```
cagcgaggaa gtgacgccca ccgaggccag gcggcgcggt gccttccgtg aggacgcatt   3240
gaccgaggcc gacgccctgg cggccgccga gaatgaacgc caagaggaac aagcatgaaa   3300
ccgcaccagg acggccagga cgaaccgttt ttcattaccg aagagatcga ggcggagatg   3360
atcgcggccg ggtacgtgtt cgagccgccc gcgcacgtct caaccgtgcg gctgcatgaa   3420
atcctggccg gtttgtctga tgccaagctg gcggcctggc cggccagctt ggccgctgaa   3480
gaaaccgagc gccgccgtct aaaaaggtga tgtgtatttg agtaaaacag cttgcgtcat   3540
gcggtcgctg cgtatatgat gcgatgagta aataaacaaa tacgcaaggg gaacgcatga   3600
aggttatcgc tgtacttaac cagaaaggcg ggtcaggcaa gacgaccatc gcaacccatc   3660
tagcccgcgc cctgcaactc gccggggccg atgttctgtt agtcgattcc gatccccagg   3720
gcagtgcccg cgattgggcg gccgtgcggg aagatcaacc gctaaccgtt gtcggcatcg   3780
accgcccgac gattgaccgc gacgtgaagg ccatcggccg gcgcgacttc gtagtgatcg   3840
acggagcgcc ccaggcggcg gacttggctg tgtccgcgat caaggcagcc gacttcgtgc   3900
tgattccggt gcagccaagc ccttacgaca tatgggccac cgccgacctg gtggagctgg   3960
ttaagcagcg cattgaggtc acggatggaa ggctacaagc ggcctttgtc gtgtcgcggg   4020
cgatcaaagg cacgcgcatc ggcggtgagg ttgccgaggc gctggccggg tacgagctgc   4080
ccattcttga gtcccgtatc acgcagcgcg tgagctaccc aggcactgcc gccgccggca   4140
caaccgttct tgaatcagaa cccgagggcg acgctgcccg cgaggtccag gcgctggccg   4200
ctgaaattaa atcaaaactc atttgagtta atgaggtaaa gagaaaatga gcaaaagcac   4260
aaacacgcta agtgccggcc gtccgagcgc acgcagcagc aaggctgcaa cgttggccag   4320
cctggcagac acgccagcca tgaagcgggt caactttcag ttgccggcgg aggatcacac   4380
caagctgaag atgtacgcgg tacgccaagg caagaccatt accgagctgc tatctgaata   4440
catcgcgcag ctaccagagt aaatgagcaa atgaataaat gagtagatga attttagcgg   4500
ctaaaggagg cggcatggaa aatcaagaac aaccaggcac cgacgccgtg gaatgcccca   4560
tgtgtggagg aacgggcggt tggccaggcg taagcggctg ggttgtctgc cggccctgca   4620
atggcactgg aacccccaag cccgaggaat cggcgtgacg gtcgcaaacc atccggcccg   4680
gtacaaatcg gcgcggcgct gggtgatgac ctggtggaga agttgaaggc cgcgcaggcc   4740
gcccagcggc aacgcatcga ggcagaagca cgccccggtg aatcgtggca agcggccgct   4800
gatcgaatcc gcaaagaatc ccggcaaccg ccggcagccg gtgcgccgtc gattaggaag   4860
ccgcccaagg gcgacgagca accagatttt ttcgttccga tgctctatga cgtgggcacc   4920
cgcgatagtc gcagcatcat ggacgtggcc gttttccgtc tgtcgaagcg tgaccgacga   4980
gctggcgagg tgatccgcta cgagcttcca gacgggcacg tagaggtttc cgcagggccg   5040
gccggcatgg ccagtgtgtg ggattacgac ctggtactga tggcggtttc ccatctaacc   5100
gaatccatga accgataccg ggaagggaag ggagacaagc ccggccgcgt gttccgtcca   5160
cacgttgcgg acgtactcaa gttctgccgg cgagccgatg gcggaaagca gaaagacgac   5220
ctggtagaaa cctgcattcg gttaaacacc acgcacgttg ccatgcagcg tacgaagaag   5280
gccaagaacg gccgcctggt gacggtatcc gagggtgaag ccttgattag ccgctacaag   5340
atcgtaaaga gcgaaaccgg gcggccggag tacatcgaga tcgagctagc tgattggatg   5400
taccgcgaga tcacagaagg caagaacccg gacgtgctga cggttcaccc cgattacttt   5460
ttgatcgatc ccggcatcgg ccgttttctc taccgcctgg cacgccgcgc cgcaggcaag   5520
gcagaagcca gatggttgtt caagacgatc tacgaacgca gtggcagcgc cggagagttc   5580
```

```
aagaagttct gtttcaccgt gcgcaagctg atcgggtcaa atgacctgcc ggagtacgat   5640
ttgaaggagg aggcggggca ggctggcccg atcctagtca tgcgctaccg caacctgatc   5700
gagggcgaag catccgccgg ttcctaatgt acggagcaga tgctagggca aattgcccta   5760
gcaggggaaa aaggtcgaaa aggtctcttt cctgtggata gcacgtacat tgggaaccca   5820
aagccgtaca ttgggaaccg gaacccgtac attgggaacc caaagccgta cattgggaac   5880
cggtcacaca tgtaagtgac tgatataaaa gagaaaaaag gcgatttttc cgcctaaaac   5940
tctttaaaac ttattaaaac tcttaaaacc cgcctggcct gtgcataact gtctggccag   6000
cgcacagccg aagagctgca aaaagcgcct acccttcggt cgctgcgctc cctacgcccc   6060
gccgcttcgc gtcggcctat cgcggccgct ggccgctcaa aaatggctgg cctacggcca   6120
ggcaatctac cagggcgcgg acaagccgcg ccgtcgccac tcgaccgccg gcgcccacat   6180
caaggcaccc tgcctcgcgc gtttcggtga tgacggtgaa aacctctgac acatgcagct   6240
cccggagacg gtcacagctt gtctgtaagc ggatgccggg agcagacaag cccgtcaggg   6300
cgcgtcagcg ggtgttggcg ggtgtcgggg cgcagccatg acccagtcac gtagcgatag   6360
cggagtgtat actggcttaa ctatgcggca tcagagcaga ttgtactgag agtgcaccat   6420
atgcggtgtg aaataccgca cagatgcgta aggagaaaat accgcatcag gcgctcttcc   6480
gcttcctcgc tcactgactc gctgcgctcg gtcgttcggc tgcggcgagc ggtatcagct   6540
cactcaaagg cggtaatacg gttatccaca gaatcagggg ataacgcagg aaagaacatg   6600
tgagcaaaag gccagcaaaa ggccaggaac cgtaaaaagg ccgcgttgct ggcgtttttc   6660
cataggctcc gcccccctga cgagcatcac aaaaatcgac gctcaagtca gaggtggcga   6720
aacccgacag gactataaag ataccaggcg tttccccctg gaagctccct cgtgcgctct   6780
cctgttccga ccctgccgct taccggatac ctgtccgcct ttctcccttc gggaagcgtg   6840
gcgctttctc atagctcacg ctgtaggtat ctcagttcgg tgtaggtcgt tcgctccaag   6900
ctgggctgtg tgcacgaacc ccccgttcag cccgaccgct gcgccttatc cggtaactat   6960
cgtcttgagt ccaacccggt aagacacgac ttatcgccac tggcagcagc cactggtaac   7020
aggattagca gagcgaggta tgtaggcggt gctacagagt tcttgaagtg gtggcctaac   7080
tacggctaca ctagaaggac agtatttggt atctgcgctc tgctgaagcc agttaccttc   7140
ggaaaaagag ttggtagctc ttgatccggc aaacaaacca ccgctggtag cggtggtttt   7200
tttgtttgca agcagcagat tacgcgcaga aaaaaaggat ctcaagaaga tcctttgatc   7260
ttttctacgg ggtctgacgc tcagtggaac gaaaactcac gttaagggat tttggtcatg   7320
cattctaggt actaaaacaa ttcatccagt aaaatataat attttatttt ctcccaatca   7380
ggcttgatcc ccagtaagtc aaaaaatagc tcgacatact gttcttcccc gatatcctcc   7440
ctgatcgacc ggacgcagaa ggcaatgtca taccacttgt ccgccctgcc gcttctccca   7500
agatcaataa agccacttac tttgccatct ttcacaaaga tgttgctgtc tcccaggtcg   7560
ccgtgggaaa agacaagttc ctcttcgggc ttttccgtct ttaaaaaatc atacagctcg   7620
cgcggatctt taaatggagt gtcttcttcc cagttttcgc aatccacatc ggccagatcg   7680
ttattcagta agtaatccaa ttcggctaag cggctgtcta agctattcgt atagggacaa   7740
tccgatatgt cgatggagtg aaagagcctg atgcactccg catacagctc gataatcttt   7800
tcagggcttt gttcatcttc atactcttcc gagcaaagga cgccatcggc ctcactcatg   7860
agcagattgc tccagccatc atgccgttca aagtgcagga cctttggaac aggcagcttt   7920
```

-continued

```
ccttccagcc atagcatcat gtccttttcc cgttccacat cataggtggt ccctttatac   7980
cggctgtccg tcatttttaa atataggttt tcattttctc ccaccagctt atataccta    8040
gcaggagaca ttccttccgt atcttttacg cagcggtatt tttcgatcag ttttttcaat   8100
tccggtgata ttctcatttt agccatttat tatttccttc ctcttttcta cagtatttaa   8160
agatacccca agaagctaat tataacaaga cgaactccaa ttcactgttc cttgcattct   8220
aaaaccttaa ataccagaaa acagcttttt caaagttgtt ttcaaagttg gcgtataaca   8280
tagtatcgac ggagccgatt ttgaaaccgc ggtgatcaca ggcagcaacg ctctgtcatc   8340
gttacaatca acatgctacc ctccgcgaga tcatccgtgt ttcaaacccg gcagcttagt   8400
tgccgttctt ccgaatagca tcggtaacat gagcaaagtc tgccgcctta caacggctct   8460
cccgctgacg ccgtcccgga ctgatgggct gcctgtatcg agtggtgatt ttgtgccgag   8520
ctgccggtcg gggagctgtt ggctggctgg tggcaggata tattgtggtg taaacaaatt   8580
gacgcttaga caacttaata acacattgcg gacgttttta atgtactgaa ttaacgccga   8640
attaattcgg gggatctgga ttttagtact ggattttggt tttaggaatt agaaatttta   8700
ttgatagaag tattttacaa atacaaatac atactaaggg tttcttatat gctcaacaca   8760
tgagcgaaac cctataggaa ccctaattcc cttatctggg aactactcac acattattat   8820
ggagaaactc gagcttgtcg atcgacagat ccggtcggca tctactctat ttctttgccc   8880
tcggacgagt gctggggcgt cggtttccac tatcggcgag tacttctaca cagccatcgg   8940
tccagacggc cgcgcttctg cgggcgattt gtgtacgccc gacagtcccg gctccggatc   9000
ggacgattgc gtcgcatcga ccctgcgccc aagctgcatc atcgaaattg ccgtcaacca   9060
agctctgata gagttggtca agaccaatgc ggagcatata cgcccggagt cgtggcgatc   9120
ctgcaagctc cggatgcctc cgctcgaagt agcgcgtctg ctgctccata caagccaacc   9180
acggcctcca gaagaagatg ttggcgacct cgtattggga atccccgaac atcgcctcgc   9240
tccagtcaat gaccgctgtt atgcggccat tgtccgtcag gacattgttg gagccgaaat   9300
ccgcgtgcac gaggtgccgg acttcggggc agtcctcggc ccaaagcatc agctcatcga   9360
gagcctgcgc gacggacgca ctgacggtgt cgtccatcac agtttgccag tgatacacat   9420
ggggatcagc aatcgcgcat atgaaatcac gccatgtagt gtattgaccg attccttgcg   9480
gtccgaatgg gccgaacccg ctcgtctggc taagatcggc cgcagcgatc gcatccatag   9540
cctccgcgac cggttgtaga acagcgggca gttcggtttc aggcaggtct tgcaacgtga   9600
caccctgtgc acggcgggag atgcaatagg tcaggctctc gctaaactcc ccaatgtcaa   9660
gcacttccgg aatcgggagc gcggccgatg caaagtgccg ataaacataa cgatctttgt   9720
agaaaccatc ggcgcagcta tttacccgca ggacatatcc acgccctcct acatcgaagc   9780
tgaaagcacg agattcttcg ccctccgaga gctgcatcag gtcggagacg ctgtcgaact   9840
tttcgatcag aaacttctcg acagacgtcg cggtgagttc aggcttttc atatctcatt    9900
gccccccggg atctgcgaaa gctcgagaga gatagatttg tagagagaga ctggtgattt   9960
cagcgtgtcc tctccaaatg aaatgaactt ccttatatag aggaaggtct tgcgaaggat  10020
agtgggattg tgcgtcatcc cttacgtcag tggagatatc acatcaatcc acttgctttg  10080
aagacgtggt tggaacgtct tctttttcca cgatgctcct cgtgggtggg ggtccatctt  10140
tgggaccact gtcggcagag gcatcttgaa cgatagcctt tcctttatcg caatgatggc  10200
atttgtaggt gccaccttcc ttttctactg tccttttgat gaagtgacag atagctgggc  10260
aatggaatcc gaggaggttt cccgatatta ccctttgttg aaaagtctca atagcccttt  10320
```

```
ggtcttctga gactgtatct ttgatattct tggagtagac gagagtgtcg tgctccacca  10380

tgttatcaca tcaatccact tgctttgaag acgtggttgg aacgtcttct ttttccacga  10440

tgctcctcgt gggtgggggt ccatctttgg gaccactgtc ggcagaggca tcttgaacga  10500

tagcctttcc tttatcgcaa tgatggcatt tgtaggtgcc accttccttt tctactgtcc  10560

ttttgatgaa gtgacagata gctgggcaat ggaatccgag gaggtttccc gatattaccc  10620

tttgttgaaa agtctcaata gccctttggt cttctgagac tgtatctttg atattcttgg  10680

agtagacgag agtgtcgtgc tccaccatgt tggcaagctg ctctagccaa tacgcaaacc  10740

gcctctcccc gcgcgttggc cgattcatta atgcagctgg cacgacaggt ttcccgactg  10800

gaaagcgggc agtgagcgca acgcaattaa tgtgagttag ctcactcatt aggcacccca  10860

ggctttacac tttatgcttc cggctcgtat gttgtgtgga attgtgagcg gataacaatt  10920

tcacacagga aacagctatg accatgatta cg                                10952
```

<210> SEQ ID NO 2
<211> LENGTH: 16843
<212> TYPE: DNA
<213> ORGANISM: Artificial Sequence
<220> FEATURE:
<223> OTHER INFORMATION: pBC-yellow vector

<400> SEQUENCE: 2

```
ccgggctggt tgccctcgcc gctgggctgg cggccgtcta tggccctgca aacgcgccag     60

aaacgccgtc gaagccgtgt gcgagacacc gcggccgccg gcgttgtgga tacctcgcgg    120

aaaacttggc cctcactgac agatgagggg cggacgttga cacttgaggg gccgactcac    180

ccggcgcggc gttgacagat gaggggcagg ctcgatttcg gccggcgacg tggagctggc    240

cagcctcgca aatcggcgaa aacgcctgat tttacgcgag tttcccacag atgatgtgga    300

caagcctggg gataagtgcc ctgcggtatt gacacttgag ggcgcgact actgacagat     360

gaggggcgcg atccttgaca cttgaggggc agagtgctga cagatgaggg gcgcacctat    420

tgacatttga ggggctgtcc acaggcagaa aatccagcat ttgcaagggt ttccgcccgt    480

ttttcggcca ccgctaacct gtcttttaac ctgcttttaa accaatattt ataaaccttg    540

tttttaacca gggctgcgcc ctgtgcgcgt gaccgcgcac gccgaagggg ggtgcccccc    600

cttctcgaac cctcccggcc cgctaacgcg ggcctcccat ccccccaggg gctgcgcccc    660

tcggccgcga acggcctcac cccaaaaatg gcagcgctgg cagtccttgc cattgccggg    720

atcggggcag taacgggatg ggcgatcagc ccgagcgcga cgcccggaag cattgacgtg    780

ccgcaggtgc tggcatcgac attcagcgac caggtgccgg gcagtgaggg cggcggcctg    840

ggtggcggcc tgcccttcac ttcggccgtc ggggcattca cggacttcat ggcggggccg    900

gcaattttta ccttgggcat tcttggcata gtggtcgcgg gtgccgtgct cgtgttcggg    960

ggtgcgataa acccagcgaa ccatttgagg tgataggtaa gattataccg aggtatgaaa   1020

acgagaattg gacctttaca gaattactct atgaagcgcc atatttaaaa agctaccaag   1080

acgaagagga tgaagaggat gaggaggcag attgccttga atatattgac aatactgata   1140

agataatata tcttttatat agaagatatc gccgtatgta aggatttcag ggggcaaggc   1200

ataggcagcg cgcttatcaa tatatctata gaatgggcaa agcataaaaa cttgcatgga   1260

ctaatgcttg aaacccagga caataacctt atagcttgta aattctatca taattgggta   1320

atgactccaa cttattgata gtgttttatg ttcagataat gcccgatgac tttgtcatgc   1380
```

```
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttaccga ctgcggcctg agtttttttaa gtgacgtaaa atcgtgttga   1800
ggccaacgcc cataatgcgg gctgttgccc ggcatccaac gccattcatg gccatatcaa   1860
tgattttctg gtgcgtaccg ggttgagaag cggtgtaagt gaactgcagt tgccatgttt   1920
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta aatcagtaag ttggcagcat cacccataat tgtggtttca   2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340
tacggaagga atgtctcctg ctaaggtata taagctggtg ggagaaaatg aaaacctata   2400
tttaaaaatg acggacagcc ggtataaagg gaccacctat gatgtggaac gggaaaagga   2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
attggattac ttactgaata acgatctggc cgatgtggat tgcgaaaact gggaagaaga   2760
cactccattt aaagatccgc gcgagctgta tgattttttta aagacggaaa agcccgaaga   2820
ggaacttgtc ttttcccacg gcgacctggg agacagcaac atctttgtga aagatggcaa   2880
agtaagtggc tttattgatc ttgggagaag cggcagggcg gacaagtggt atgacattgc   2940
cttctgcgtc cggtcgatca gggaggatat cggggaagaa cagtatgtcg agctattttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctcccccct gccctgcccg cgccatcggc cgccgtggag cgttcgcgtc   3600
gtctcgaaca ggaggcggca ggtttggcga agtcgatgac catcgacacg cgaggaacta   3660
tgacgaccaa gaagcgaaaa accgccggcg aggacctggc aaaacaggtc agcgaggcca   3720
agcaggccgc gttgctgaaa cacacgaagc agcagatcaa ggaaatgcag ctttccttgt   3780
```

```
tcgatattgc gccgtggccg gacacgatgc gagcgatgcc aaacgacacg gcccgctctg   3840
ccctgttcac cacgcgcaac aagaaaatcc cgcgcgaggc gctgcaaaac aaggtcattt   3900
tccacgtcaa caaggacgtg aagatcacct acaccggcgt cgagctgcgg gccgacgatg   3960
acgaactggt gtggcagcag gtgttggagt acgcgaagcg cacccctatc ggcgagccga   4020
tcaccttcac gttctacgag ctttgccagg acctgggctg gtcgatcaat ggccggtatt   4080
acacgaaggc cgaggaatgc ctgtcgcgcc tacaggcgac ggcgatgggc ttcacgtccg   4140
accgcgttgg gcacctggaa tcggtgtcgc tgctgcaccg cttccgcgtc ctggaccgtg   4200
gcaagaaaac gtcccgttgc caggtcctga tcgacgagga aatcgtcgtg ctgtttgctg   4260
gcgaccacta cacgaaattc atatgggaga agtaccgcaa gctgtcgccg acggcccgac   4320
ggatgttcga ctatttcagc tcgcaccggg agccgtaccc gctcaagctg gaaaccttcc   4380
gcctcatgtg cggatcggat tccacccgcg tgaagaagtg gcgcgagcag gtcggcgaag   4440
cctgcgaaga gttgcgaggc agcggcctgg tggaacacgc ctgggtcaat gatgacctgg   4500
tgcattgcaa acgctagggc cttgtggggt cagttccggc tgggggttca gcagccagcg   4560
ctttactggc atttcaggaa caagcgggca ctgctcgacg cacttgcttc gctcagtatc   4620
gctcgggacg cacggcgcgc tctacgaact gccgataaac agaggattaa aattgacaat   4680
tgtgattaag gctcagattc gacggcttgg agcggccgac gtgcaggatt tccgcgagat   4740
ccgattgtcg gccctgaaga aagctccaga gatgttcggg tccgtttacg agcacgagga   4800
gaaaaagccc atggaggcgt tcgctgaacg gttgcgagat gccgtggcat tcggcgccta   4860
catcgacggc gagatcattg ggctgtcggt cttcaaacag gaggacggcc ccaaggacgc   4920
tcacaaggcg catctgtccg gcgttttcgt ggagcccgaa cagcgaggcc gaggggtcgc   4980
cggtatgctg ctgcgggcgt tgccggcggg tttattgctc gtgatgatcg tccgacagat   5040
tccaacggga atctggtgga tgcgcatctt catcctcggc gcacttaata tttcgctatt   5100
ctggagcttg ttgtttattt cggtctaccg cctgccgggc ggggtcgcgg cgacggtagg   5160
cgctgtgcag ccgctgatgg tcgtgttcat ctctgccgct ctgctaggta gcccgatacg   5220
attgatggcg gtcctggggg ctatttgcgg aactgcgggc gtggcgctgt tggtgttgac   5280
accaaacgca gcgctagatc ctgtcggcgt cgcagcgggc ctggcggggg cggtttccat   5340
ggcgttcgga accgtgctga cccgcaagtg gcaacctccc gtgcctctgc tcacctttac   5400
cgcctggcaa ctggcggccg gaggacttct gctcgttcca gtagctttag tgtttgatcc   5460
gccaatcccg atgcctacag gaaccaatgt tctcggcctg gcgtggctcg gcctgatcgg   5520
agcgggttta acctacttcc tttggttccg ggggatctcg cgactcgaac ctacagttgt   5580
ttccttactg ggctttctca gccccagatc tggggtcgat cagccgggga tgcatcaggc   5640
cgacagtcgg aacttcgggt ccccgacctg taccattcgg tgagcaatgg ataggggagt   5700
tgatatcgtc aacgttcact tctaaagaaa tagcgccact cagcttcctc agcggcttta   5760
tccagcgatt tcctattatg tcggcatagt tctcaagatc gacagcctgt cacggttaag   5820
cgagaaatga ataagaaggc tgataattcg gatctctgcg agggagatga tatttgatca   5880
caggcagcaa cgctctgtca tcgttacaat caacatgcta ccctccgcga gatcatccgt   5940
gtttcaaacc cggcagctta gttgccgttc ttccgaatag catcggtaac atgagcaaag   6000
tctgccgcct tacaacggct ctcccgctga cgccgtcccg gactgatggg ctgcctgtat   6060
cgagtggtga ttttgtgccg agctgccggt cggggagctg ttggctggct ggtggcagga   6120
```

```
tatattgtgg tgtaaacaaa ttgacgctta gacaacttaa taacacattg cggacgtttt   6180
taatgtactg gggtggtttt tcttttcacc agtgagacgg gcaacagctg attgcccttc   6240
accgcctggc cctgagagag ttgcagcaag cggtccacgc tggtttgccc cagcaggcga   6300
aaatcctgtt tgatggtggt tccgaaatcg gcaaaatccc ttataaatca aaagaatagc   6360
ccgagatagg gttgagtgtt gttccagttt ggaacaagag tccactatta aagaacgtgg   6420
actccaacgt caaagggcga aaaaccgtct atcagggcga tggcccacta cctgtatggc   6480
cgcattcgca aaacacacct agactagatt tgttttgcta acccaattga tattaattat   6540
atatgattaa tatttatatg tatatggatt tggttaatga aatgcatctg gttcatcaaa   6600
gaattataaa gacacgtgac attcatttag gataagaaat atggatgatc tctttctctt   6660
ttattcagat aactagtaat tacacataac acacaacttt gatgcccaca ttatagtgat   6720
tagcatgtca ctatgtgtgc atccttttat ttcatacatt aattaagttg gccaatccag   6780
aagatggaca agtctaggtt aaccatgtgg tacctacgcg ttcgaatatc catgggccgc   6840
ttcaggccag ggcgctgggg aaggcgatgg cgtgctcggt cagctgccac ttctggttct   6900
tggcgtcgct ccggtcctcc cgcagcagct tgtgctggat gaagtgccac tcgggcatct   6960
tgctgggcac gctcttggcc ttgtacacgg tgtcgaactg gcaccggtac cggccgccgt   7020
ccttcagcag caggtacatg ctcacgtcgc ccttcaggat gccctgctta ggcacgggca   7080
tgatcttctc gcagctggcc tcccagttgg tggtcatctt cttcatcacg gggccgtcgg   7140
cggggaagtt cacgccgttg aagatgctct tgtggtagat gcagttctcc ttcacgctca   7200
cggtgatgtc cacgttacag atgcacacgg cgccgtcctc gaacaggaag ctccggcccc   7260
aggtgtagcc ggcggggcag ctgttcttga agtagtccac gatgtcctgg gggtactcgg   7320
tgaagatccg gtcgccgtac ttgaagccgg cgctcaggat gtcctcgctg aagggcaggg   7380
ggccgccctc gatcacgcac aggttgatgg tctgcttgcc cttgaagggg tagccgatgc   7440
cctcgccggt gatcacgaac ttgtggccgt tcacgcagcc ctccatgtgg tacttcatgg   7500
tcatctcctc cttcaggccg tgcttgctgt gggccatggt ggcgaccggt gaattcgagc   7560
tcggtacccg gggatcctga gtaaaacaga ggagggtctc actaagttta tagagagact   7620
gagagagata aagggacacg tatgaagcgt ctgttttcgt ggtgtgacgt caaagtcatt   7680
ttgctctcta cgcgtgtctg tgtcggcttg atcttttttt ttgctttttg gaactcatgt   7740
cggtagtata tcttttattt atttttttctt tttttccctt ttctttcaaa ctgatgtcgg   7800
tatgatattt attccatcct aaaatgtaac ttactattat tagtagtcgg tccatgtcta   7860
ttggcccatc atgtggtcat tttacgttta cgtcgtgtgg ctgtttatta taacaaacgg   7920
cacatccttc tcattcgaat tgtatttctc cttaatcgtt ctaataggta tgatctttta   7980
ttttatacgt aaaattaaaa ttgaatgatg tcaagaacga aaattaattt gtatttacaa   8040
aggagctaaa tattgtttat tcctctactg gtagaagata aaagaagtag atgaaataat   8100
gatcttacta gagaatattc ctcatttaca ctagtcaaat ggaaatcttg taaactttta   8160
caataattta tcctgaaaat atgaaaaaat agaagaaaat gtttacctcc tctctcctct   8220
taattcacct acgatcggtg cgggcctctt cgctattacg ccagctggcg aaagggggat   8280
gtgctgcaag gcgattaagt tgggtaacgc cagggttttc ccagtcacga cgttgtaaaa   8340
cgacggccag tgaattcgag ctcggtaccc ggggatcctc tagagtcgac ctgcaggcat   8400
gcaagcttgt tgaaacatcc ctgaagtgtc tcattttatt ttatttattc tttgctgata   8460
aaaaaataaa ataaaagaag ctaagcacac ggtcaaccat tgctctactg ctaaaagggt   8520
```

```
tatgtgtagt gttttactgc ataaattatg cagcaaacaa gacaactcaa attaaaaaat   8580
ttcctttgct tgtttttttg ttgtctctga cttgactttc ttgtggaagt tggttgtata   8640
aggattggga cacaccattg tccttcttaa tttaatttta tttctttgct gataaaaaaa   8700
aaaaatttca tatagtgtta aataataatt tgttaaataa ccaaaaagtc aaatatgttt   8760
actctcgttt aaataattga gagtcgtcca gcaaggctaa acgattgtat agatttatga   8820
caatatttac ttttttatag ataaatgtta tattataata aatttatata catatattat   8880
atgttattta ttatttatta ttattttaaa tccttcaata ttttatcaaa ccaactcata   8940
attttttttt tatctgtaag aagcaataaa attaaataga cccactttaa ggatgatcca   9000
acctttatac agagtaagag agttcaaata gtaccctttc atatacatat caactaaaat   9060
attagaaata tcatggatca aaccttataa agacattaaa taagtggata agtataaatat  9120
ataaatgggt agtatataat atataaatgg atacaaactt ctctctttat aattgttatg   9180
tctccttaac atcctaatat aatacataag tgggtaatat ataatatata aatggagaca   9240
aacttcttcc attataattg ttatgtcttc ttaacactta tgtctcgttc acaatgctaa   9300
agttagaatt gtttagaaag tcttatagta cacatttgtt tttgtactat ttgaagcatt   9360
ccataagccg tcacgattca gatgatttat aataataaga ggaaatttat catagaacaa   9420
taaggtgcat agatagagtg ttaatatatc ataacatcct ttgtttattc atagaagaag   9480
tgagatggag ctcagttatt atactgttac atggtcggat acaatattcc atgctctcca   9540
tgagctctta cacctacatg cattttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaaccact ttgtacaaga aagctgaacg   9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcag gttaatggcg tttttgatgt   9900
cattttcgcg gtggctgaga tcagccactt cttccccgat aacggagacc ggcacactgg   9960
ccatatcggt ggtcatcatg cgccagcttt catccccgat atgcaccacc gggtaaagtt  10020
cacgggagac tttatctgac agcagacgtg cactggccag gggatcacc atccgtcgcc   10080
cgggcgtgtc aataatatca ctctgtacat ccacaaacag acgataacgg ctctctcttt  10140
tataggtgta aaccttaaac tgcatttcac cagtccctgt tctcgtcagc aaaagagccg  10200
ttcatttcaa taaaccgggc gacctcagcc atcccttcct gattttccgc tttccagcgt  10260
tcggcacgca gacgacgggc ttcattctgc atggttgtgc ttaccagacc ggagatattg  10320
acatcatata tgccttgagc aactgatagc tgtcgctgtc aactgtcact gtaatacgct  10380
gcttcatagc acacctcttt ttgacatact tcgggtatac atatcagtat atattcttat  10440
accgcaaaaa tcagcgcgca aatacgcata ctgttatctg gcttttagta agccggatcc  10500
tctagattac gccccgccct gccactcatc gcagtactgt tgtaattcat taagcattct  10560
gccgacatgg aagccatcac agacggcatg atgaacctga atcgccagcg gcatcagcac  10620
cttgtcgcct tgcgtataat atttgcccat ggtgaaaacg ggggcgaaga agttgtccat  10680
attggccacg tttaaatcaa aactggtgaa actcacccag ggattggctg agacgaaaaa  10740
catattctca ataaaccctt tagggaaata ggccaggttt tcaccgtaac acgccacatc  10800
ttgcgaatat atgtgtagaa actgccggaa atcgtcgtgg tattcactcc agagcgatga  10860
```

```
aaacgtttca gtttgctcat ggaaaacggt gtaacaaggg tgaacactat cccatatcac  10920
cagctcaccg tctttcattg ccatacggaa ttccggatga gcattcatca ggcgggcaag  10980
aatgtgaata aaggccggat aaaacttgtg cttatttttc tttacggtct ttaaaaaggc  11040
cgtaatatcc agctgaacgg tctggttata ggtacattga gcaactgact gaaatgcctc  11100
aaaatgttct ttacgatgcc attgggatat atcaacggtg gtatatccag tgattttttt  11160
ctccatttta gcttccttag ctcctgaaaa tctcgccgga tcctaactca aaatccacac  11220
attatacgag ccggaagcat aaagtgtaaa gcctggggtg cctaatgcgg ccgccatagt  11280
gactggatat gttgtgtttt acagtattat gtagtctgtt ttttatgcaa aatctaattt  11340
aatatattga tatttatatc attttacgtt tctcgttcag cttttttgta caaacttgtt  11400
tgataaccgg tactagtgtg cacgtcgagc gtgtcctctc caaatgaaat gaacttcctt  11460
atatagagga agggtcttgc gaaggatagt gggattgtgc gtcatccctt acgtcagtgg  11520
agatgtcaca tcaatccact tgctttgaag acgtggttgg aacgtcttct ttttccacga  11580
tgctcctcgt gggtgggggt ccatctttgg gaccactgtc ggcagaggca tcttgaatga  11640
tagcctttcc tttatcgcaa tgatggcatt tgtaggagcc accttccttt tctactgtcc  11700
tttcgatgaa gtgacagata gctgggcaat ggaatccgag gaggtttccc gaaattatcc  11760
tttgttgaaa agtctcaata gccctttggt cttctgagac tgtatctttg acatttttgg  11820
agtagaccag agtgtcgtgc tccaccatgt tgacgaagat tttcttcttg tcattgagtc  11880
gtaaaagact ctgtatgaac tgttcgccag tcttcacggc gagttctgtt agatcctcga  11940
tttgaatctt agactccatg catggcctta gattcagtag gaactacctt tttagagact  12000
ccaatctcta ttacttgcct tggtttatga agcaagcctt gaatcgtcca tactggaata  12060
gtacttctga tcttgagaaa tatgtctttc tctgtgttct tgatgcaatt agtcctgaat  12120
cttttgactg catctttaac cttcttggga aggtatttga tctcctggag attgttactc  12180
gggtagatcg tcttgatgag acctgctgcg taggcctctc taaccatctg tgggtcagca  12240
ttctttctga aattgaagag gctaaccttc tcattatcag tggtgaacat agtgtcgtca  12300
ccttcacctt cgaacttcct tcctagatcg taaagataga ggaaatcgtc cattgtaatc  12360
tccggggcaa aggagatctc ttttggggct ggatcactgc tgggcctttt ggttcctagc  12420
gtgagccagt gggctttttg ctttggtggg cttgttaggg ccttagcaaa gctcttgggc  12480
ttgagttgag cttctccttt ggggatgaag ttcaacctgt ctgtttgctg acttgttgtg  12540
tacgcgtcag ctgctgctct tgcctctgta atagtggcaa atttcttgtg tgcaactccg  12600
ggaacgccgt ttgttgccgc ctttgtacaa ccccagtcat cgtatatacc ggcatgtgga  12660
ccgttataca caacgtagta gttgatatga gggtgttgaa tacccgattc tgctctgaga  12720
ggagcaactg tgctgttaag ctcagatttt tgtgggattg gaattggatc ctctagagca  12780
aagcttggcg taatcatggt catagctgtt tcctgtgtga aattgttatc cgctcacaat  12840
tccacacaac atacgagccg gaagcataaa gtgtaaagcc tggggtgcct aatgagtgag  12900
ctaactcaca ttaattgcgt tgcgctcact gcccgctttc cagtcgggaa acctgtcgtg  12960
ccagctgcat taatgaatcg gccaacgcgc ggggagaggc ggtttgcgta ttgggccaaa  13020
gacaaaaggg cgacattcaa ccgattgagg gagggaaggt aaatattgac ggaaattatt  13080
cattaaaggt gaattatcac cgtcaccgac ttgagccatt tgggaattag agccagcaaa  13140
atcaccagta gcaccattac cattagcaag gccggaaacg tcaccaatga aaccatcatc  13200
tagtaacata gatgacaccg cgcgcgataa tttatcctag tttgcgcgct atattttgtt  13260
```

```
ttctatcgcg tattaaatgt ataattgcgg gactctaatc ataaaaaccc atctcataaa  13320
taacgtcatg cattacatgt taattattac atgcttaacg taattcaaca gaaattatat  13380
gataatcatc gcaagaccgg caacaggatt caatcttaag aaactttatt gccaaatgtt  13440
tgaacgatct gcttcgacgc actccttctt taggtacgga ctagatctcg gtgacgggca  13500
ggaccggacg gggcggtacc ggcaggctga agtccagctg ccagaaaccc acgtcatgcc  13560
agttcccgtg cttgaagccg gccgcccgca gcatgccgcg gggggcatat ccgagcgcct  13620
cgtgcatgcg cacgctcggg tcgttgggca gcccgatgac agcgaccacg ctcttgaagc  13680
cctgtgcctc cagggacttc agcaggtggg tgtagagcgt ggagcccagt cccgtccgct  13740
ggtggcgggg ggagacgtac acggtcgact cggccgtcca gtcgtaggcg ttgcgtgcct  13800
tccaggggcc cgcgtaggcg atgccggcga cctcgccgtc cacctcggcg acgagccagg  13860
gatagcgctc ccgcagacgg acgaggtcgt ccgtccactc ctgcggttcc tgcggctcgg  13920
tacggaagtt gaccgtgctt gtctcgatgt agtggttgac gatggtgcag accgccggca  13980
tgtccgcctc ggtggcacgg cggatgtcgg ccgggcgtcg ttctgggctc atggatctgg  14040
attgagagtg aatatgagac tctaattgga taccgagggg aatttatgga acgtcagtgg  14100
agcatttttg acaagaaata tttgctagct gatagtgacc ttaggcgact tttgaacgcg  14160
caataatggt ttctgacgta tgtgcttagc tcattaaact ccagaaaccc gcggctgagt  14220
ggctccttca acgttgcggt tctgtcagtt ccaaacgtaa aacggcttgt cccgcgtcat  14280
cggcgggggt cataacgtga ctcccttaat tctccgctca tgatcagatt gtcgtttccc  14340
gccttcagtt taaactatca gtgtttgaca ggatatattg gcgggtaaac ctaagagaaa  14400
agagcgttta ttagaataat cggatattta aaagggcgtg aaaaggttta tccgttcgtc  14460
catttgtatg tgcatgccaa ccacagggtt ccccagatct ggcgccggcc agcgagacga  14520
gcaagattgg ccgccgcccg aaacgatccg acagcgcgcc cagcacaggt gcgcaggcaa  14580
attgcaccaa cgcatacagc gccagcagaa tgccatagtg ggcggtgacg tcgttcgagt  14640
gaaccagatc gcgcaggagg cccggcagca ccggcataat caggccgatg ccgacagcgt  14700
cgagcgcgac agtgctcaga attacgatca ggggtatgtt gggtttcacg tctggcctcc  14760
ggaccagcct ccgctggtcc gattgaacgc gcggattctt tatcactgat aagttggtgg  14820
acatattatg tttatcagtg ataaagtgtc aagcatgaca aagttgcagc cgaatacagt  14880
gatccgtgcc gccctggacc tgttgaacga ggtcggcgta gacggtctga cgacacgcaa  14940
actggcggaa cggttggggg ttcagcagcc ggcgctttac tggcacttca ggaacaagcg  15000
ggcgctgctc gacgcactgg ccgaagccat gctggcggag aatcatacgc attcggtgcc  15060
gagagccgac gacgactggc gctcatttct gatcgggaat gcccgcagct tcaggcaggc  15120
gctgctcgcc taccgcgatg gcgcgcgcat ccatgccggc acgcgaccgg gcgcaccgca  15180
gatggaaacg gccgacgcgc agcttcgctt cctctgcgag gcgggttttt cggccgggga  15240
cgccgtcaat gcgctgatga caatcagcta cttcactgtt ggggccgtgc ttgaggagca  15300
ggccggcgac agcgatgccg gcgagcgcgg cggcaccgtt gaacaggctc cgctctcgcc  15360
gctgttgcgg gccgcgatag acgccttcga cgaagccggt ccggacgcag cgttcgagca  15420
gggactcgcg gtgattgtcg atggattggc gaaaaggagg ctcgttgtca ggaacgttga  15480
aggaccgaga aagggtgacg attgatcagg accgctgccg gagcgcaacc cactcactac  15540
agcagagcca tgtagacaac atcccctccc cctttccacc gcgtcagacg cccgtagcag  15600
```

```
cccgctacgg gctttttcat gccctgccct agcgtccaag cctcacggcc gcgctcggcc  15660

tctctggcgg ccttctggcg ctcttccgct tcctcgctca ctgactcgct gcgctcggtc  15720

gttcggctgc ggcgagcggt atcagctcac tcaaaggcgg taatacggtt atccacagaa  15780

tcaggggata acgcaggaaa gaacatgtga gcaaaaggcc agcaaaaggc caggaaccgt  15840

aaaaaggccg cgttgctggc gtttttccat aggctccgcc cccctgacga gcatcacaaa  15900

aatcgacgct caagtcagag gtggcgaaac ccgacaggac tataaagata ccaggcgttt  15960

ccccctggaa gctccctcgt gcgctctcct gttccgaccc tgccgcttac cggatacctg  16020

tccgcctttc tcccttcggg aagcgtggcg cttttccgct gcataaccct gcttcggggt  16080

cattatagcg attttttcgg tatatccatc ctttttcgca cgatatacag gattttgcca  16140

aagggttcgt gtagactttc cttggtgtat ccaacggcgt cagccgggca ggataggtga  16200

agtaggccca cccgcgagcg ggtgttcctt cttcactgtc ccttattcgc acctggcggt  16260

gctcaacggg aatcctgctc tgcgaggctg gccggctacc gccggcgtaa cagatgaggg  16320

caagcggatg gctgatgaaa ccaagccaac caggaagggc agcccaccta tcaaggtgta  16380

ctgccttcca gacgaacgaa gagcgattga ggaaaaggcg gcggcggccg gcatgagcct  16440

gtcggcctac ctgctggccg tcggccaggg ctacaaaatc acgggcgtcg tggactatga  16500

gcacgtccgc gagctggccc gcatcaatgg cgacctgggc cgcctgggcg gcctgctgaa  16560

actctggctc accgacgacc cgcgcacggc gcggttcggt gatgccacga tcctcgccct  16620

gctggcgaag atcgaagaga agcaggacga gcttggcaag gtcatgatgg gcgtggtccg  16680

cccgagggca gagccatgac ttttttagcc gctaaaacgg ccgggggggtg cgcgtgattg  16740

ccaagcacgt ccccatgcgc tccatcaaga agagcgactt cgcggagctg gtgaagtaca  16800

tcaccgacga gcaaggcaag accgagcgcc tttgcgacgc tca                   16843
```

<210> SEQ ID NO 3
<211> LENGTH: 1921
<212> TYPE: DNA
<213> ORGANISM: Artificial Sequence
<220> FEATURE:
<223> OTHER INFORMATION: The nucleotide sequence of DsRed expression cassette

<400> SEQUENCE: 3

```
cgaagctggc cgctctagaa ctagtggatc tcgatgtgta gtctacgaga agggttaacc     60

gtctcttcgt gagaataacc gtggcctaaa aataagccga tgaggataaa taaaatgtgg    120

tggtacagta cttcaagagg tttactcatc aagaggatgc ttttccgatg agctctagta    180

gtacatcgga cctcacatac ctccattgtg gtgaaatatt ttgtgctcat ttagtgatgg    240

gtaaattttg tttatgtcac tctaggtttt gacatttcag ttttgccact cttaggtttt    300

gacaaataat ttccattccg cggcaaaagc aaaacaattt tattttactt ttaccactct    360

tagctttcac aatgtatcac aaatgccact ctagaaattc tgtttatgcc acagaatgtg    420

aaaaaaaaca ctcacttatt tgaagccaag gtgttcatgg catggaaatg tgacataaag    480

taacgttcgt gtataagaaa aaattgtact cctcgtaaca agagacggaa acatcatgag    540

acaatcgcgt ttggaaggct ttgcatcacc tttggatgat gcgcatgaat ggagtcgtct    600

gcttgctagc cttcgcctac cgcccactga gtccgggcgg caactaccat cggcgaacga    660

cccagctgac ctctaccgac cggacttgaa tgcgctacct tcgtcagcga cgatggccgc    720

gtacgctggc gacgtgcccc cgcatgcatg gcggcacatg gcgagctcag accgtgcgtg    780
```

```
gctggctaca aatacgtacc ccgtgagtgc cctagctaga aacttacacc tgcaactgcg    840

agagcgagcg tgtgagtgta gccgagtaga tcctcgccac catggcctcc tccgagaacg    900

tcatcaccga gttcatgcgc ttcaaggtgc gcatggaggg caccgtgaac ggccacgagt    960

tcgagatcga gggcgagggc gagggccgcc cctacgaggg ccacaacacc gtgaagctga   1020

aggtgacgaa gggcggcccc ctgcccttcg cctgggacat cctgtccccc cagttccagt   1080

acggctccaa ggtgtacgtg aagcaccccg ccgacatccc cgactacaag aagctgtcct   1140

tccccgaggg cttcaagtgg gagcgcgtga tgaacttcga ggacggcggc gtggcgaccg   1200

tgacccagga ctcctccctg caggacggct gcttcatcta caaggtgaag ttcatcggcg   1260

tgaacttccc ctccgacggc cccgtgatgc agaagaagac catgggctgg gaggcctcca   1320

ccgagcgcct gtacccccgc gacggcgtgc tgaagggcga gacccacaag gccctgaagc   1380

tgaaggacgg cggccactac ctggtggagt tcaagtccat ctacatggcc aagaagcccg   1440

tgcagctgcc cggctactac tacgtggacg ccaagctgga catcacctcc cacaacgagg   1500

actacaccat cgtggagcag tacgagcgca ccgagggccg ccaccacctg ttcctgtagc   1560

ggcccatgga tattcgaacg cgtaggtacc acatggttaa cctagacttg tccatcttct   1620

ggattggcca acttaattaa tgtatgaaat aaaaggatgc acacatagtg acatgctaat   1680

cactataatg tgggcatcaa agttgtgtgt tatgtgtaat tactagttat ctgaataaaa   1740

gagaaagaga tcatccatat ttcttatcct aaatgaatgt cacgtgtctt tataattctt   1800

tgatgaacca gatgcatttc attaaccaaa tccatataca tataaatatt aatcatatat   1860

aattaatatc aattgggtta gcaaaacaaa tctagtctag gtgtgttttg cgaatgcggc   1920

c                                                                   1921
```

<210> SEQ ID NO 4
<211> LENGTH: 1444
<212> TYPE: DNA
<213> ORGANISM: Oryza sativa

<400> SEQUENCE: 4

```
gagcgaactg cttggttggg aatggcggcg cccgtggccg gccgcctctc cgggctcctc     60

cggcgatgcg cggcggccgg ggcggtccgg ccgggagagc aggcgcacgc gagggcggtg    120

gtgggcgggt ggctccccga cgccaccctg gagaccgacc tcgtgctgat gtactgcagg    180

tgcggcgagc gtcggcgcgc acgcagggtg ttcgacggaa tgcgtgcgcc gtccatgcac    240

gcgtacaacg tgctcctcgc ggcgtcgcct ccccgcgacg cgatggaggt gttctcccgc    300

ctcctcgcgt cggggctccg ccctgacggt tactctgtcc ccgccgtggt acgtgcctgc    360

gctgagctcc ccgacgcggt gcttggcggg gtgatccacg gcttcgccgt ccggctcggc    420

ttgatgggga acgttgttgt ggccgctgcg cttctggata tgtatgccaa ggctggtttc    480

ctggatgatg cggtgagggt gttcgacgag atgacggaga gggatgctgt cgtctggaac    540

tgcatggttg cagggtatgc gagggctggg agggcagtag aaacctttga gattttcagc    600

agagcgcagg ttgaggcggt gaacatggtg aatggtctgc aggctgtgcc cagcgtgttg    660

aatatctgcg cgaaggaagg ggagctgatg aagggtaggg aaatccatgg taggatggtg    720

aggtgccttg catttgattc ggatatcgca gtggggaacg ctttgatcaa catgtatgca    780

aagtgcggcc gggtcaatgt atcacaagca gtgttttctg gcatgcagca gagggatgtg    840

gtgagctggt ctacaatgat tcatagctac agcattcatg gcaaggggga acaggcattg    900

aaggtttaca tggaaatgtt gtctgaggga gtgaaaccaa attggatcac attcacatca    960
```

```
gttctgtcaa gttgcagcca ctccgggctt gtaaccgagg gtcggaagat cttcgagtcg   1020

atgactaagg ttcatggtgt ccaccctgct gctgagcact atgcatgtat ggttgacctc   1080

ttagggcgtg ctggagccat tgaagaagct gttgggctta taaggaagat gcccatggaa   1140

ccttgtgcta gcgtgtgggg agctttgctc tctgcatgtg ctatgcataa taacgtcgat   1200

gttggagaga ttgcagcttt taggctattt gagttagaag aaggcagtgc tagcaattat   1260

gttaccctct gtggaattta tgacgcagtt ggtcaatctg atggtgttgc agggttgaga   1320

tcaaggatga gagaactcgg catggtgaag acgcctgggt gcagtcggat cgatgtgaag   1380

ggaagagctc atgctttcta ccaggggagc atcccacgtt atttgaggag atgaatgctt   1440

tggg                                                                1444
```

<210> SEQ ID NO 5
<211> LENGTH: 1413
<212> TYPE: DNA
<213> ORGANISM: Oryza sativa

<400> SEQUENCE: 5

```
atggcggcgc ccgtggccgg ccgcctctcc gggctcctcc ggcgatgcgc ggcggccggg     60

gcggtccggc cgggagagca ggcgcacgcg agggcggtgg tgggcgggtg gctccccgac    120

gccaccctgg agaccgacct cgtgctgatg tactgcaggt gcggcgagcg tcggcgcgca    180

cgcagggtgt tcgacggaat gcgtgcgccg tccatgcacg cgtacaacgt gctcctcgcg    240

gcgtcgcctc cccgcgacgc gatggaggtg ttctcccgcc tcctcgcgtc ggggctccgc    300

cctgacggtt actctgtccc cgccgtggta cgtgcctgcg ctgagctccc cgacgcggtg    360

cttggcgggg tgatccacgg cttcgccgtc cggctcggct tgatggggaa cgttgttgtg    420

gccgctgcgc ttctggatat gtatgccaag gctggtttcc tggatgatgc ggtgagggtg    480

ttcgacgaga tgacggagag ggatgctgtc gtctggaact gcatggttgc agggtatgcg    540

agggctggga gggcagtaga aacctttgag attttcagca gagcgcaggt tgaggcggtg    600

aacatggtga atggtctgca ggctgtgccc agcgtgttga atatctgcgc gaaggaaggg    660

gagctgatga agggtaggga aatccatggt aggatggtga ggtgccttgc atttgattcg    720

gatatcgcag tggggaacgc tttgatcaac atgtatgcaa agtgcggccg ggtcaatgta    780

tcacaagcag tgttttctgg catgcagcag agggatgtgg tgagctggtc tacaatgatt    840

catagctaca gcattcatgg caagggggaa caggcattga aggtttacat ggaaatgttg    900

tctgagggag tgaaaccaaa ttggatcaca ttcacatcag ttctgtcaag ttgcagccac    960

tccgggcttg taaccgaggg tcggaagatc ttcgagtcga tgactaaggt tcatggtgtc   1020

caccctgctg ctgagcacta tgcatgtatg gttgacctct tagggcgtgc tggagccatt   1080

gaagaagctg ttgggcttat aaggaagatg cccatggaac cttgtgctag cgtgtgggga   1140

gctttgctct ctgcatgtgc tatgcataat aacgtcgatg ttggagagat tgcagctttt   1200

aggctatttg agttagaaga aggcagtgct agcaattatg ttaccctctg tggaatttat   1260

gacgcagttg gtcaatctga tggtgttgca gggttgagat caaggatgag agaactcggc   1320

atggtgaaga cgcctgggtg cagtcggatc gatgtgaagg gaagagctca tgctttctac   1380

caggggagca tcccacgtta tttgaggaga tga                                1413
```

<210> SEQ ID NO 6
<211> LENGTH: 470
<212> TYPE: PRT

<213> ORGANISM: Oryza sativa

<400> SEQUENCE: 6

```
Met Ala Ala Pro Val Ala Gly Arg Leu Ser Gly Leu Leu Arg Arg Cys
1               5                   10                  15

Ala Ala Ala Gly Ala Val Arg Pro Gly Glu Gln Ala His Ala Arg Ala
            20                  25                  30

Val Val Gly Gly Trp Leu Pro Asp Ala Thr Leu Glu Thr Asp Leu Val
        35                  40                  45

Leu Met Tyr Cys Arg Cys Gly Glu Arg Arg Arg Ala Arg Arg Val Phe
    50                  55                  60

Asp Gly Met Arg Ala Pro Ser Met His Ala Tyr Asn Val Leu Leu Ala
65                  70                  75                  80

Ala Ser Pro Pro Arg Asp Ala Met Glu Val Phe Ser Arg Leu Leu Ala
                85                  90                  95

Ser Gly Leu Arg Pro Asp Gly Tyr Ser Val Pro Ala Val Val Arg Ala
            100                 105                 110

Cys Ala Glu Leu Pro Asp Ala Val Leu Gly Gly Val Ile His Gly Phe
        115                 120                 125

Ala Val Arg Leu Gly Leu Met Gly Asn Val Val Val Ala Ala Ala Leu
    130                 135                 140

Leu Asp Met Tyr Ala Lys Ala Gly Phe Leu Asp Asp Ala Val Arg Val
145                 150                 155                 160

Phe Asp Glu Met Thr Glu Arg Asp Ala Val Val Trp Asn Cys Met Val
                165                 170                 175

Ala Gly Tyr Ala Arg Ala Gly Arg Ala Val Glu Thr Phe Glu Ile Phe
            180                 185                 190

Ser Arg Ala Gln Val Glu Ala Val Asn Met Val Asn Gly Leu Gln Ala
        195                 200                 205

Val Pro Ser Val Leu Asn Ile Cys Ala Lys Glu Gly Glu Leu Met Lys
    210                 215                 220

Gly Arg Glu Ile His Gly Arg Met Val Arg Cys Leu Ala Phe Asp Ser
225                 230                 235                 240

Asp Ile Ala Val Gly Asn Ala Leu Ile Asn Met Tyr Ala Lys Cys Gly
                245                 250                 255

Arg Val Asn Val Ser Gln Ala Val Phe Ser Gly Met Gln Gln Arg Asp
            260                 265                 270

Val Val Ser Trp Ser Thr Met Ile His Ser Tyr Ser Ile His Gly Lys
        275                 280                 285

Gly Glu Gln Ala Leu Lys Val Tyr Met Glu Met Leu Ser Glu Gly Val
    290                 295                 300

Lys Pro Asn Trp Ile Thr Phe Thr Ser Val Leu Ser Ser Cys Ser His
305                 310                 315                 320

Ser Gly Leu Val Thr Glu Gly Arg Lys Ile Phe Glu Ser Met Thr Lys
                325                 330                 335

Val His Gly Val His Pro Ala Ala Glu His Tyr Ala Cys Met Val Asp
            340                 345                 350

Leu Leu Gly Arg Ala Gly Ala Ile Glu Glu Ala Val Gly Leu Ile Arg
        355                 360                 365

Lys Met Pro Met Glu Pro Cys Ala Ser Val Trp Gly Ala Leu Leu Ser
    370                 375                 380

Ala Cys Ala Met His Asn Asn Val Asp Val Gly Glu Ile Ala Ala Phe
385                 390                 395                 400
```

```
Arg Leu Phe Glu Leu Glu Glu Gly Ser Ala Ser Asn Tyr Val Thr Leu
                405                 410                 415

Cys Gly Ile Tyr Asp Ala Val Gly Gln Ser Asp Gly Val Ala Gly Leu
            420                 425                 430

Arg Ser Arg Met Arg Glu Leu Gly Met Val Lys Thr Pro Gly Cys Ser
        435                 440                 445

Arg Ile Asp Val Lys Gly Arg Ala His Ala Phe Tyr Gln Gly Ser Ile
    450                 455                 460

Pro Arg Tyr Leu Arg Arg
465                 470


<210> SEQ ID NO 7
<211> LENGTH: 2315
<212> TYPE: DNA
<213> ORGANISM: Oryza sativa

<400> SEQUENCE: 7

cgaatggccg gcaatgtcat ccggcttgaa ctctctgagg cttctttggg tggccaagtt      60

ttgcaaggcc ggatgagtcc ttccttggct tctctcgagc atcttgagta cctcgacctc     120

agtgctctcg tccttccggg catcaacagc agtagcccaa agttcttggg ttctatgacg     180

aacctgagat atcttgatct ctctgggtgt tttctctctg gtagtgtgtc tccttggctc     240

ggcaaccttt ccaaattgga gtaccttgat ctctctttct caaccttgtc aggtagggtt     300

ccacctgagc tcggtaacct gacaaggttg aaacatctgg accttggtaa catgcaacat     360

atgtactcgg cagatatctc atggattact catctgcgat ccttggagta tcttgacatg     420

agcttggtga atctgctgaa cacaattcca tctttggagg ttctcaacct tgtgaaattc     480

acacttccta gtacacccca agcactcgcg caactaaacc tcacgaaact cgtgcagctc     540

gatctctcgt cgaacagatt gggccatcca atccaatcat gttggttttg gaacctgacg     600

agtatcgaat ccctcgagct ctctgaaaca tttcttcatg gtccgtttcc taccgcgcta     660

ggaagtttca cggcactcca gtggcttggg tttagtgata acggtaatgc agcaacgttg     720

ctagcggaca tgagaagtct ctgttctatg aaaagcttgg gtctaggtgg tagtctatct     780

catgggaaca tagaggattt ggtagacagg ttgccacatg gtattactag agataaacca     840

gcacaagaag ggaattttac aagtttgtct tatcttgatc tttctgacaa ccatcttgct     900

gggattatac catcagatat tgcatatacc atccctagct tatgtcacct tgacctttct     960

aggaataatc tgactggacc tatacccata atagagaact ctagcttaag tgagctcatc    1020

ctccgttcca accaactaac gggtcaaata ccgaaattag atagaaaaat tgaagtcatg    1080

gatatctcca taaacttgtt gtcagggcct ttgcccatag atattgggtc tccaaacctt    1140

ctagcactaa ttctgtcctc taattatctt atcggtcgaa ttccagaatc agtttgtgaa    1200

tcacagtcca tgattatcgt ggatttgtcc aacaattttc ttgagggagc ctttcccaag    1260

tgttttcaga tgcaaaggtt gattttcctc ctcttaagtc acaatagctt ctctgctaaa    1320

ctcccatcat ttctccgcaa ctcaaatttg ttaagctatg tggatctatc atggaacaaa    1380

ttcagtggaa cattgccaca atggattgga catatggtga acttgcattt tctacacctt    1440

agccacaaca tgttttacgg tcatattcca atcaaaatca caaatcttaa aaatctccac    1500

tacttcagtt tagcagcaaa caatatatct ggtgcaatac cacggtgttt gtcaaagtta    1560

acaatgatga taggaaaaca atcgacaata atagagatcg attggtttca tgcgtatttt    1620

gacgttgtgg atgggtctct tggaagaatt ttctctgttg tgatgaagca ccaagaacaa    1680
```

```
caatatggtg atagcattct cgatgtggtg ggcatcgact tgtcactcaa tagtttaact   1740

ggtggaatac cggatgagat cacttctctt aaaagattgc tcagtttaaa tttatcatgg   1800

aatcaattga gcggagaaat cgtagagaag attggggcga tgaattcatt ggaatcactt   1860

gacctctcgc ggaacaaatt ttctggtgaa attcctccaa gtttggccaa tctggcatat   1920

ctaagctact tggacttgtc atacaataat cttacaggaa gaattccacg aggaagccaa   1980

ctcgataccc tctatgccga gaaccctcac atatatgatg gaaacaacgg tctctatggt   2040

cctcccctcc aaaggaattg cttgggcagt gaactaccaa agaatagcag ccaaatcatg   2100

agcaaaaatg tttctgatga actaatgttc tactttggac ttgggtccgg gtttacagtt   2160

ggtctctggg ttgttttctg tgttgtattg ttcaagaaaa cttggagaat tgccttgttt   2220

cgcctctttg ataggataca cgacaaagta tatgtgtttg tcgccataac ctgggccagt   2280

attggtagag aggctaccac agattaatag gtact                              2315
```

<210> SEQ ID NO 8
<211> LENGTH: 2304
<212> TYPE: DNA
<213> ORGANISM: Oryza sativa

<400> SEQUENCE: 8

```
atggccggca atgtcatccg gcttgaactc tctgaggctt ctttgggtgg ccaagttttg     60

caaggccgga tgagtccttc cttggcttct ctcgagcatc ttgagtacct cgacctcagt    120

gctctcgtcc ttccgggcat caacagcagt agcccaaagt tcttgggttc tatgacgaac    180

ctgagatatc ttgatctctc tgggtgtttt ctctctggta gtgtgtctcc ttggctcggc    240

aacctttcca aattggagta ccttgatctc tctttctcaa ccttgtcagg tagggttcca    300

cctgagctcg gtaacctgac aaggttgaaa catctggacc ttggtaacat gcaacatatg    360

tactcggcag atatctcatg gattactcat ctgcgatcct tggagtatct tgacatgagc    420

ttggtgaatc tgctgaacac aattccatct ttggaggttc tcaaccttgt gaaattcaca    480

cttcctagta caccccaagc actcgcgcaa ctaaacctca cgaaactcgt gcagctcgat    540

ctctcgtcga acagattggg ccatccaatc caatcatgtt ggttttggaa cctgacgagt    600

atcgaatccc tcgagctctc tgaaacattt cttcatggtc cgtttcctac cgcgctagga    660

agtttcacgg cactccagtg gcttgggttt agtgataacg gtaatgcagc aacgttgcta    720

gcggacatga gaagtctctg ttctatgaaa agcttgggtc taggtggtag tctatctcat    780

gggaacatag aggatttggt agacaggttg ccacatggta ttactagaga taaaccagca    840

caagaaggga attttacaag tttgtcttat cttgatcttt ctgacaacca tcttgctggg    900

attataccat cagatattgc atataccatc cctagcttat gtcaccttga cctttctagg    960

aataatctga ctggacctat acccataata gagaactcta gcttaagtga gctcatcctc   1020

cgttccaacc aactaacggg tcaaataccg aaattagata gaaaaattga agtcatggat   1080

atctccataa acttgttgtc agggcctttg cccatagata ttgggtctcc aaaccttcta   1140

gcactaattc tgtcctctaa ttatcttatc ggtcgaattc cagaatcagt ttgtgaatca   1200

cagtccatga ttatcgtgga tttgtccaac aattttcttg agggagcctt tcccaagtgt   1260

tttcagatgc aaaggttgat tttcctcctc ttaagtcaca atagcttctc tgctaaactc   1320

ccatcatttc tccgcaactc aaatttgtta agctatgtgg atctatcatg gaacaaattc   1380

agtggaacat tgccacaatg gattggacat atggtgaact tgcattttct acaccttagc   1440

cacaacatgt tttacggtca tattccaatc aaaatcacaa atcttaaaaa tctccactac   1500
```

-continued

```
ttcagtttag cagcaaacaa tatatctggt gcaataccac ggtgtttgtc aaagttaaca   1560
atgatgatag gaaaacaatc gacaataata gagatcgatt ggtttcatgc gtattttgac   1620
gttgtggatg ggtctcttgg aagaattttc tctgttgtga tgaagcacca agaacaacaa   1680
tatggtgata gcattctcga tgtggtgggc atcgacttgt cactcaatag tttaactggt   1740
ggaataccgg atgagatcac ttctcttaaa agattgctca gtttaaattt atcatggaat   1800
caattgagcg gagaaatcgt agagaagatt ggggcgatga attcattgga atcacttgac   1860
ctctcgcgga acaaattttc tggtgaaatt cctccaagtt tggccaatct ggcatatcta   1920
agctacttgg acttgtcata caataatctt acaggaagaa ttccacgagg aagccaactc   1980
gataccctct atgccgagaa ccctcacata tatgatggaa acaacggtct ctatggtcct   2040
cccctccaaa ggaattgctt gggcagtgaa ctaccaaaga atagcagcca aatcatgagc   2100
aaaaatgttt ctgatgaact aatgttctac tttggacttg ggtccgggtt tacagttggt   2160
ctctgggttg ttttctgtgt tgtattgttc aagaaaactt ggagaattgc cttgtttcgc   2220
ctctttgata ggatacacga caaagtatat gtgtttgtcg ccataacctg ggccagtatt   2280
ggtagagagg ctaccacaga ttaa                                           2304
```

<210> SEQ ID NO 9
<211> LENGTH: 767
<212> TYPE: PRT
<213> ORGANISM: Oryza sativa

<400> SEQUENCE: 9

```
Met Ala Gly Asn Val Ile Arg Leu Glu Leu Ser Glu Ala Ser Leu Gly
1               5                   10                  15

Gly Gln Val Leu Gln Gly Arg Met Ser Pro Ser Leu Ala Ser Leu Glu
            20                  25                  30

His Leu Glu Tyr Leu Asp Leu Ser Ala Leu Val Leu Pro Gly Ile Asn
        35                  40                  45

Ser Ser Ser Pro Lys Phe Leu Gly Ser Met Thr Asn Leu Arg Tyr Leu
    50                  55                  60

Asp Leu Ser Gly Cys Phe Leu Ser Gly Ser Val Ser Pro Trp Leu Gly
65                  70                  75                  80

Asn Leu Ser Lys Leu Glu Tyr Leu Asp Leu Ser Phe Ser Thr Leu Ser
                85                  90                  95

Gly Arg Val Pro Pro Glu Leu Gly Asn Leu Thr Arg Leu Lys His Leu
            100                 105                 110

Asp Leu Gly Asn Met Gln His Met Tyr Ser Ala Asp Ile Ser Trp Ile
        115                 120                 125

Thr His Leu Arg Ser Leu Glu Tyr Leu Asp Met Ser Leu Val Asn Leu
    130                 135                 140

Leu Asn Thr Ile Pro Ser Leu Glu Val Leu Asn Leu Val Lys Phe Thr
145                 150                 155                 160

Leu Pro Ser Thr Pro Gln Ala Leu Ala Gln Leu Asn Leu Thr Lys Leu
                165                 170                 175

Val Gln Leu Asp Leu Ser Ser Asn Arg Leu Gly His Pro Ile Gln Ser
            180                 185                 190

Cys Trp Phe Trp Asn Leu Thr Ser Ile Glu Ser Leu Glu Leu Ser Glu
        195                 200                 205

Thr Phe Leu His Gly Pro Phe Pro Thr Ala Leu Gly Ser Phe Thr Ala
    210                 215                 220
```

-continued

```
Leu Gln Trp Leu Gly Phe Ser Asp Asn Gly Asn Ala Ala Thr Leu Leu
225                 230                 235                 240

Ala Asp Met Arg Ser Leu Cys Ser Met Lys Ser Leu Gly Leu Gly Gly
                245                 250                 255

Ser Leu Ser His Gly Asn Ile Glu Asp Leu Val Asp Arg Leu Pro His
            260                 265                 270

Gly Ile Thr Arg Asp Lys Pro Ala Gln Glu Gly Asn Phe Thr Ser Leu
        275                 280                 285

Ser Tyr Leu Asp Leu Ser Asp Asn His Leu Ala Gly Ile Ile Pro Ser
    290                 295                 300

Asp Ile Ala Tyr Thr Ile Pro Ser Leu Cys His Leu Asp Leu Ser Arg
305                 310                 315                 320

Asn Asn Leu Thr Gly Pro Ile Pro Ile Ile Glu Asn Ser Ser Leu Ser
                325                 330                 335

Glu Leu Ile Leu Arg Ser Asn Gln Leu Thr Gly Gln Ile Pro Lys Leu
            340                 345                 350

Asp Arg Lys Ile Glu Val Met Asp Ile Ser Ile Asn Leu Leu Ser Gly
        355                 360                 365

Pro Leu Pro Ile Asp Ile Gly Ser Pro Asn Leu Leu Ala Leu Ile Leu
    370                 375                 380

Ser Ser Asn Tyr Leu Ile Gly Arg Ile Pro Glu Ser Val Cys Glu Ser
385                 390                 395                 400

Gln Ser Met Ile Ile Val Asp Leu Ser Asn Asn Phe Leu Glu Gly Ala
                405                 410                 415

Phe Pro Lys Cys Phe Gln Met Gln Arg Leu Ile Phe Leu Leu Leu Ser
            420                 425                 430

His Asn Ser Phe Ser Ala Lys Leu Pro Ser Phe Leu Arg Asn Ser Asn
        435                 440                 445

Leu Leu Ser Tyr Val Asp Leu Ser Trp Asn Lys Phe Ser Gly Thr Leu
    450                 455                 460

Pro Gln Trp Ile Gly His Met Val Asn Leu His Phe Leu His Leu Ser
465                 470                 475                 480

His Asn Met Phe Tyr Gly His Ile Pro Ile Lys Ile Thr Asn Leu Lys
                485                 490                 495

Asn Leu His Tyr Phe Ser Leu Ala Ala Asn Asn Ile Ser Gly Ala Ile
            500                 505                 510

Pro Arg Cys Leu Ser Lys Leu Thr Met Met Ile Gly Lys Gln Ser Thr
        515                 520                 525

Ile Ile Glu Ile Asp Trp Phe His Ala Tyr Phe Asp Val Val Asp Gly
    530                 535                 540

Ser Leu Gly Arg Ile Phe Ser Val Val Met Lys His Gln Glu Gln Gln
545                 550                 555                 560

Tyr Gly Asp Ser Ile Leu Asp Val Val Gly Ile Asp Leu Ser Leu Asn
                565                 570                 575

Ser Leu Thr Gly Gly Ile Pro Asp Glu Ile Thr Ser Leu Lys Arg Leu
            580                 585                 590

Leu Ser Leu Asn Leu Ser Trp Asn Gln Leu Ser Gly Glu Ile Val Glu
        595                 600                 605

Lys Ile Gly Ala Met Asn Ser Leu Glu Ser Leu Asp Leu Ser Arg Asn
    610                 615                 620

Lys Phe Ser Gly Glu Ile Pro Pro Ser Leu Ala Asn Leu Ala Tyr Leu
625                 630                 635                 640

Ser Tyr Leu Asp Leu Ser Tyr Asn Asn Leu Thr Gly Arg Ile Pro Arg
```

```
            645                 650                 655

Gly Ser Gln Leu Asp Thr Leu Tyr Ala Glu Asn Pro His Ile Tyr Asp
        660                 665                 670

Gly Asn Asn Gly Leu Tyr Gly Pro Pro Leu Gln Arg Asn Cys Leu Gly
    675                 680                 685

Ser Glu Leu Pro Lys Asn Ser Ser Gln Ile Met Ser Lys Asn Val Ser
    690                 695                 700

Asp Glu Leu Met Phe Tyr Phe Gly Leu Gly Ser Gly Phe Thr Val Gly
705                 710                 715                 720

Leu Trp Val Val Phe Cys Val Val Leu Phe Lys Lys Thr Trp Arg Ile
                725                 730                 735

Ala Leu Phe Arg Leu Phe Asp Arg Ile His Asp Lys Val Tyr Val Phe
            740                 745                 750

Val Ala Ile Thr Trp Ala Ser Ile Gly Arg Glu Ala Thr Thr Asp
        755                 760                 765


<210> SEQ ID NO 10
<211> LENGTH: 749
<212> TYPE: DNA
<213> ORGANISM: Oryza sativa

<400> SEQUENCE: 10

ccaggctact actagtactc taccaacaaa aggagcaatg gccccaccgg tcagccaccc      60

gtcaggtggg tgcaacagtc caatcgcgta ggaaagcggc aaacacgaca ccacgagctg     120

cggtcccccc ccccacgcga gacgatccga cgaccctccg tcgcccgcgc ccacgatcgg     180

acggtccaga tcgacgtgtc cccctggcg atcccccgcg gccacgcgcg ggggcgggta     240

tccgcgagcg cgggagaggt ggggcccact tcccctcctc cttgcaggtg ggggacgtgg     300

ggccacgccc tgtcagtggc agcggcgggc gggtacccgc ggcgcgggta agggatggtg     360

ggcggtgaga aaagtttcgt ggtccaattg gttgtacttt ggcgtcagcg tggggcccca     420

cggtgacggg aaggaggcct atgagagctt gccacgtcac cgattttttt tgcgagacga     480

gattgatgca cttggggtgt gatgcgcccc gctttttgag ccccccctgcc tgctgtgttt     540

ccccttgctg cccgtatccg attccaaact gtggttgccc ttgtcgaccc atggattgat     600

gcaaacttta gtttttagta ataatagctt tttttcttt tcaactcgaa attttgaaaa     660

tattttatag gtgcgcatta aagaaattca ataaaaacac cgcattatcg aaagtgttgt     720

cagcgtgaat ctaatgatat actccgtag                                       749


<210> SEQ ID NO 11
<211> LENGTH: 147
<212> TYPE: DNA
<213> ORGANISM: Oryza sativa

<400> SEQUENCE: 11

atggccccac cggtggggga cgtggggcca cgccctgtca gtggcagcgg cgggcgggta      60

cccgcggcgc gggtaaggga tggtgggcgg tgcgcattaa agaaattcaa taaaaacacc     120

gcattatcga aagtgttgtc agcgtga                                         147


<210> SEQ ID NO 12
<211> LENGTH: 48
<212> TYPE: PRT
<213> ORGANISM: Oryza sativa

<400> SEQUENCE: 12
```

-continued

```
Met Ala Pro Pro Val Gly Asp Val Gly Pro Arg Pro Val Ser Gly Ser
1               5                   10                  15

Gly Gly Arg Val Pro Ala Ala Arg Val Arg Asp Gly Gly Arg Cys Ala
            20                  25                  30

Leu Lys Lys Phe Asn Lys Asn Thr Ala Leu Ser Lys Val Leu Ser Ala
        35                  40                  45
```

<210> SEQ ID NO 13
<211> LENGTH: 949
<212> TYPE: DNA
<213> ORGANISM: Oryza sativa

<400> SEQUENCE: 13

```
gagaccgaga gagagaagca gcacccaaac cctagccctc ccctctcctc ccgcacgcgc     60

gcgtcggcgc caccaccggg agctccgccg ccgccgccgc ctcatccgcc ccgtgccatg    120

gcggagaccc ccgagcgcag gaggtactca gggtccccct ctccttacag gggaaaccca    180

aaatcaaggt caagatcacg atcacctgct gctcgatccc agtctaggtc tccagtccct    240

gaccctagat ctcaggcaag gtcaagatca agaagccgcg agagggagcc tgatgctgta    300

aatcatggaa atacactgta tgtgactgga ctctcttctc gagtgactga aagagaactt    360

aaagattact tctctaaaga aggaagggtg actagttgcc atgttgtcct tgaaccccat    420

acacgtgttt ctcgtggatt tgcttttgtc accatggaca ctgttgaaga tgctgaacgc    480

tgtatcaagt atcttaacca gtctgtaatg gaaggccgga acatcacagt tgaaaagtca    540

cgtcgaggtc gcccaaggac gccaactcct ggaagctatc ttggtcatcg atatgaccgt    600

agagagccac gtgggagata ccgcagcaga ggaggtggct atggccgtga tgagtactac    660

ggcaatagct accgcaggtc tccgcctcca atgtacccat cctacaggga cacaagggac    720

taccctccat acagggacac aagggactac tccccccaca gggatgctcg agattactac    780

gacggaaggg gaggcagggg atactcccca catagatctc ctccttatgg cggtggcagg    840

gcccggaggg agcgatctag atcattgccg tattctccct accggatgcc tgagagaggc    900

tatggacgcc aagccggtgg tggtggctat gacaggtaag gttgctccc                949
```

<210> SEQ ID NO 14
<211> LENGTH: 822
<212> TYPE: DNA
<213> ORGANISM: Oryza sativa

<400> SEQUENCE: 14

```
atggcggaga cccccgagcg caggaggtac tcagggtccc cctctcctta caggggaaac     60

ccaaaatcaa ggtcaagatc acgatcacct gctgctcgat cccagtctag gtctccagtc    120

cctgacccta gatctcaggc aaggtcaaga tcaagaagcc gcgagaggga gcctgatgct    180

gtaaatcatg gaaatacact gtatgtgact ggactctctt ctcgagtgac tgaaagagaa    240

cttaaagatt acttctctaa agaaggaagg gtgactagtt gccatgttgt ccttgaaccc    300

catacacgtg tttctcgtgg atttgctttt gtcaccatgg acactgttga agatgctgaa    360

cgctgtatca agtatcttaa ccagtctgta atggaaggcc ggaacatcac agttgaaaag    420

tcacgtcgag gtcgcccaag gacgccaact cctggaagct atcttggtca tcgatatgac    480

cgtagagagc cacgtgggag ataccgcagc agaggaggtg gctatggccg tgatgagtac    540

tacggcaata gctaccgcag gtctccgcct ccaatgtacc catcctacag ggacacaagg    600

gactaccctc catacaggga cacaagggac tactccccccc acagggatgc tcgagattac    660
```

```
tacgacggaa ggggaggcag gggatactcc ccacatagat ctcctcctta tggcggtggc    720

agggcccgga gggagcgatc tagatcattg ccgtattctc cctaccggat gcctgagaga    780

ggctatggac gccaagccgg tggtggtggc tatgacaggt aa                       822


<210> SEQ ID NO 15
<211> LENGTH: 273
<212> TYPE: PRT
<213> ORGANISM: Oryza sativa

<400> SEQUENCE: 15

Met Ala Glu Thr Pro Glu Arg Arg Arg Tyr Ser Gly Ser Pro Ser Pro
1               5                   10                  15

Tyr Arg Gly Asn Pro Lys Ser Arg Ser Arg Ser Arg Ser Pro Ala Ala
            20                  25                  30

Arg Ser Gln Ser Arg Ser Pro Val Pro Asp Pro Arg Ser Gln Ala Arg
        35                  40                  45

Ser Arg Ser Arg Ser Arg Glu Arg Glu Pro Asp Ala Val Asn His Gly
    50                  55                  60

Asn Thr Leu Tyr Val Thr Gly Leu Ser Ser Arg Val Thr Glu Arg Glu
65                  70                  75                  80

Leu Lys Asp Tyr Phe Ser Lys Glu Gly Arg Val Thr Ser Cys His Val
                85                  90                  95

Val Leu Glu Pro His Thr Arg Val Ser Arg Gly Phe Ala Phe Val Thr
            100                 105                 110

Met Asp Thr Val Glu Asp Ala Glu Arg Cys Ile Lys Tyr Leu Asn Gln
        115                 120                 125

Ser Val Met Glu Gly Arg Asn Ile Thr Val Glu Lys Ser Arg Arg Gly
    130                 135                 140

Arg Pro Arg Thr Pro Thr Pro Gly Ser Tyr Leu Gly His Arg Tyr Asp
145                 150                 155                 160

Arg Arg Glu Pro Arg Gly Arg Tyr Arg Ser Arg Gly Gly Gly Tyr Gly
                165                 170                 175

Arg Asp Glu Tyr Tyr Gly Asn Ser Tyr Arg Arg Ser Pro Pro Pro Met
            180                 185                 190

Tyr Pro Ser Tyr Arg Asp Thr Arg Asp Tyr Pro Pro Tyr Arg Asp Thr
        195                 200                 205

Arg Asp Tyr Ser Pro His Arg Asp Ala Arg Asp Tyr Tyr Asp Gly Arg
    210                 215                 220

Gly Gly Arg Gly Tyr Ser Pro His Arg Ser Pro Pro Tyr Gly Gly Gly
225                 230                 235                 240

Arg Ala Arg Arg Glu Arg Ser Arg Ser Leu Pro Tyr Ser Pro Tyr Arg
                245                 250                 255

Met Pro Glu Arg Gly Tyr Gly Arg Gln Ala Gly Gly Gly Gly Tyr Asp
            260                 265                 270

Arg


<210> SEQ ID NO 16
<211> LENGTH: 24
<212> TYPE: DNA
<213> ORGANISM: Artificial Sequence
<220> FEATURE:
<223> OTHER INFORMATION: Forward primer for cloning cDNA of OsDN-PPR1

<400> SEQUENCE: 16

gagcgaactg cttggttggg aatg                                            24
```

<210> SEQ ID NO 17
<211> LENGTH: 28
<212> TYPE: DNA
<213> ORGANISM: Artificial Sequence
<220> FEATURE:
<223> OTHER INFORMATION: Reverse primer for cloning cDNA of OsDN-PPR1

<400> SEQUENCE: 17
cccaaagcat tcatctcctc aaataacg 28

<210> SEQ ID NO 18
<211> LENGTH: 22
<212> TYPE: DNA
<213> ORGANISM: Artificial Sequence
<220> FEATURE:
<223> OTHER INFORMATION: Forward primer for cloning cDNA of OsLRP1

<400> SEQUENCE: 18
cgaatggccg gcaatgtcat cc 22

<210> SEQ ID NO 19
<211> LENGTH: 28
<212> TYPE: DNA
<213> ORGANISM: Artificial Sequence
<220> FEATURE:
<223> OTHER INFORMATION: Reverse primer for cloning cDNA of OsLRP1

<400> SEQUENCE: 19
agtacctatt aatctgtggt agcctctc 28

<210> SEQ ID NO 20
<211> LENGTH: 27
<212> TYPE: DNA
<213> ORGANISM: Artificial Sequence
<220> FEATURE:
<223> OTHER INFORMATION: Forward primer for cloning gDNA of OsDN-LNP1

<400> SEQUENCE: 20
ccaggctact actagtactc taccaac 27

<210> SEQ ID NO 21
<211> LENGTH: 29
<212> TYPE: DNA
<213> ORGANISM: Artificial Sequence
<220> FEATURE:
<223> OTHER INFORMATION: Reverse primer for cloning gDNA of OsDN-LNP1

<400> SEQUENCE: 21
ctacggagta tatcattaga ttcacgctg 29

<210> SEQ ID NO 22
<211> LENGTH: 25
<212> TYPE: DNA
<213> ORGANISM: Artificial Sequence
<220> FEATURE:
<223> OTHER INFORMATION: Forward primer for cloning cDNA of OsRRM1

<400> SEQUENCE: 22
gagaccgaga gagagaagca gcacc 25

<210> SEQ ID NO 23
<211> LENGTH: 25
<212> TYPE: DNA
<213> ORGANISM: Artificial Sequence
<220> FEATURE:
<223> OTHER INFORMATION: Reverse primer for cloning cDNA of OsRRM1

```
<400> SEQUENCE: 23

gggagcaacc ttacctgtca tagcc                                    25


<210> SEQ ID NO 24
<211> LENGTH: 23
<212> TYPE: DNA
<213> ORGANISM: Artificial Sequence
<220> FEATURE:
<223> OTHER INFORMATION: Forward primer for real-time RT-PCR analysis of
      OsLRP1 gene

<400> SEQUENCE: 24

ctcccatcat ttctccgcaa ctc                                      23


<210> SEQ ID NO 25
<211> LENGTH: 23
<212> TYPE: DNA
<213> ORGANISM: Artificial Sequence
<220> FEATURE:
<223> OTHER INFORMATION: Reverse primer for real-time RT-PCR analysis of
      OsLRP1 gene

<400> SEQUENCE: 25

ccaagagacc catccacaac gtc                                      23


<210> SEQ ID NO 26
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsDN-LTP1 gene

<400> SEQUENCE: 26

gtgcgcatta aagaaattca                                          20


<210> SEQ ID NO 27
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsDN-LTP1 gene

<400> SEQUENCE: 27

tcacgctgac aacactttc                                           19
```

PLANTS HAVING ALTERED AGRONOMIC CHARACTERISTICS UNDER NITROGEN LIMITING CONDITIONS AND RELATED CONSTRUCTS AND METHODS INVOLVING LOW NITROGEN TOLERANCE GENES

FIELD

The field of the disclosure relates to plant breeding and genetics and, in particular, relates to recombinant DNA constructs useful in plants for conferring nitrogen use efficiency and/or tolerance to nitrogen limiting conditions and/or drought conditions.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, nitrogen, temperature extremes, and synthetic chemicals such as herbicides.

Abiotic stresses such as drought, high salinity and deficiency of nutrient elements adversely affect the growth and productivity of plants including crops, which significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

The absorption of nitrogen by plants plays an important role in their growth (Gallais et al., *J. Exp. Bot.* 55(396):295-306 (2004)). Plants synthesize amino acids from inorganic nitrogen in the environment. Consequently, nitrogen fertilization has been a powerful tool for increasing the yield of cultivated plants, such as rice, maize and soybean. Lack of sufficient plant-available nitrogen for optimum growth and development may be considered as an abiotic stress. In order to avoid pollution by nitrates and to maintain a sufficient profit margin, today farmers desire to reduce the use of nitrogen fertilizer. If a plant variety has increased nitrogen assimilation capacity, it would also be expected to have increased growth and yield. In summary, plant varieties that have better nitrogen use efficiency (NUE) are desirable.

Activation tagging can be utilized to identify genes with the ability to affect a trait. This approach has been used in the model plant species *Arabidopsis thaliana* (Weigel et al., Plant Physiol. 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant), that when placed in an organism as a transgene, can alter that trait.

SUMMARY

The following embodiments are among those encompassed by the disclosure:

One embodiment, includes an isolated polynucleotide enhancing nitrogen stress tolerance of plant through over-expression, comprising: (a) a polynucleotide with nucleotide sequence of at least 85% sequence identity, based on the Clustal V method of alignment, to SEQ ID NO: 4, 7, 10 or 13; (b) a polynucleotide with nucleotide sequence of at least 85% sequence identity, based on the Clustal V method of alignment, to SEQ ID NO: 5, 8, 11 or 14; (c) a polynucleotide encoding a polypeptide with amino acid sequence of at least 90% sequence identity, based on the Clustal V method of alignment, to SEQ ID NO: 6, 9, 12 or 15; or (d) the full complement of the nucleotide sequence of (a), (b) or (c), wherein over-expression of the polynucleotide in a plant enhances nitrogen stress tolerance. The nucleotide sequence comprises SEQ ID NO: 4, SEQ ID NO: 5, SEQ ID NO: 7, SEQ ID NO: 8, SEQ ID NO: 10, SEQ ID NO: 11, SEQ ID NO: 13 or SEQ ID NO: 14. The amino acid sequence of the polypeptide comprises SEQ ID NO: 6, SEQ ID NO: 9, SEQ ID NO: 12 or SEQ ID NO: 15.

Another embodiment, includes a recombinant DNA construct comprising the isolated polynucleotide operably linked to at least one regulatory sequence, wherein the polynucleotide comprises (a) a polynucleotide with nucleotide sequence of at least 85% sequence identity, based on the Clustal V method of alignment, to SEQ ID NO: 4, 5, 7, 8, 10, 11, 13 or 14; (b) a polynucleotide encoding a polypeptide with amino acid sequence of at least 90% sequence identity, based on the Clustal V method of alignment, to SEQ ID NO: 6, 9, 12 or 15; or (c) the full complement of the nucleotide sequence of (a) or (b); the at least one regulatory sequence is a promoter functional in a plant.

A third embodiment, includes a plant or seed comprising a recombinant DNA construct comprising the polynucleotide operably linked to at least one regulatory sequence, wherein the polynucleotide comprises (a) a polynucleotide with nucleotide sequence of at least 85% sequence identity, based on the Clustal V method of alignment, to SEQ ID NO: 4, 5, 7, 8, 10, 11, 13 or 14; (b) a polynucleotide encoding a polypeptide with amino acid sequence of at least 90% sequence identity, based on the Clustal V method of alignment, to SEQ ID NO: 6, 9, 12 or 15; or (c) the full complement of the nucleotide sequence of (a) or (b); the at least one regulatory sequence is a promoter functional in a plant.

Another embodiment, includes a plant comprising in its genome a recombinant DNA construct comprising a polynucleotide operably linked to at least one regulatory element, wherein the polynucleotide comprises (a) a polynucleotide with nucleotide sequence of at least 85% sequence identity, based on the Clustal V method of alignment, to SEQ ID NO: 4, 5, 7, 8, 10, 11, 13 or 14; (b) a polynucleotide encoding a polypeptide with amino acid sequence of at least 90% sequence identity, based on the Clustal V method of alignment, to SEQ ID NO: 6, 9, 12 or 15; or (c) the full complement of the nucleotide sequence of (a) or (b); the said plant exhibits improved nitrogen use efficiency (NUE) when compared to a control plant.

Another embodiment, includes an isolated polynucleotide enhancing drought tolerance of plant through over-expression, comprising: (a) a polynucleotide with nucleotide sequence of at least 85% sequence identity, based on the Clustal V method of alignment, to SEQ ID NO: 10; (b) a polynucleotide with nucleotide sequence of at least 85% sequence identity, based on the Clustal V method of alignment, to SEQ ID NO: 11; (c) a polynucleotide encoding a polypeptide with amino acid sequence of at least 90% sequence identity, based on the Clustal V method of alignment, to SEQ ID NO: 12; or (d) the full complement of the nucleotide sequence of (a), (b) or (c), wherein over-expression of the polynucleotide in a plant enhances drought stress tolerance. The nucleotide sequence comprises SEQ ID NO: 10 or SEQ ID NO: 11. The amino acid sequence of the polypeptide comprises SEQ ID NO: 12.

Another embodiment, includes a recombinant DNA construct comprising the isolated polynucleotide operably linked to at least one regulatory sequence, wherein the polynucleotide comprises (a) a polynucleotide with nucleotide sequence of at least 85% sequence identity, based on the Clustal V method of alignment, to SEQ ID NO: 10 or 11; (b) a polynucleotide encoding a polypeptide with amino acid sequence of at least 90% sequence identity, based on the Clustal V method of alignment, to SEQ ID NO: 12; or (c) the full complement of the nucleotide sequence of (a) or (b); the at least one regulatory sequence is a promoter functional in a plant.

Another embodiment, includes a plant or seed comprising a recombinant DNA construct comprising the polynucleotide operably linked to at least one regulatory sequence, wherein the polynucleotide comprises (a) a polynucleotide with nucleotide sequence of at least 85% sequence identity, based on the Clustal V method of alignment, to SEQ ID NO: 10 or 11; (b) a polynucleotide encoding a polypeptide with amino acid sequence of at least 90% sequence identity, based on the Clustal V method of alignment, to SEQ ID NO: 12; or (c) the full complement of the nucleotide sequence of (a) or (b); the at least one regulatory sequence is a promoter functional in a plant.

Another embodiment, includes a plant comprising in its genome a recombinant DNA construct comprising a polynucleotide operably linked to at least one regulatory element, wherein the polynucleotide comprises (a) a polynucleotide with nucleotide sequence of at least 85% sequence identity, based on the Clustal V method of alignment, to SEQ ID NO: 10 or 11; (b) a polynucleotide encoding a polypeptide with amino acid sequence of at least 90% sequence identity, based on the Clustal V method of alignment, to SEQ ID NO: 12; or (c) the full complement of the nucleotide sequence of (a) or (b); the said plant exhibits improved drought when compared to a control plant.

A further embodiment, includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, a method of increasing nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 6, 9, 12 or 15; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased nitrogen stress tolerance or NUE when compared to a control plant not comprising the recombinant DNA construct.

In another embodiment, a method of evaluating nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 6, 9, 12 or 15; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance or NUE compared to a control plant not comprising the recombinant DNA construct.

In another embodiment, a method of determining an alteration of an agronomic characteristic in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 6, 9, 12 or 15; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct, wherein said determining step (d) comprises determining whether the transgenic plant exhibits an alteration of at least one agronomic characteristic when compared, under nitrogen limiting conditions, to a control plant not comprising the recombinant DNA construct.

In another embodiment, a method of increasing drought stress tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 12; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought stress tolerance when compared to a control plant not comprising the recombinant DNA construct.

In another embodiment, a method of evaluating drought stress tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 12; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought stress tolerance compared to a control plant not comprising the recombinant DNA construct.

In another embodiment, the present disclosure concerns a recombinant DNA construct comprising any of the isolated polynucleotides of the present disclosure operably linked to at least one regulatory sequence, and a cell, a plant, and a seed comprising the recombinant DNA construct. The cell may be eukaryotic, e.g., a yeast, insect or plant cell, or prokaryotic, e.g., a bacterium.

BRIEF DESCRIPTION OF THE FIGURES

The disclosure can be more fully understood from the following detailed description of figure which forms a part of this application.

DESCRIPTION OF TABLES WITHIN THE SPECIFICATION

Figure 1:
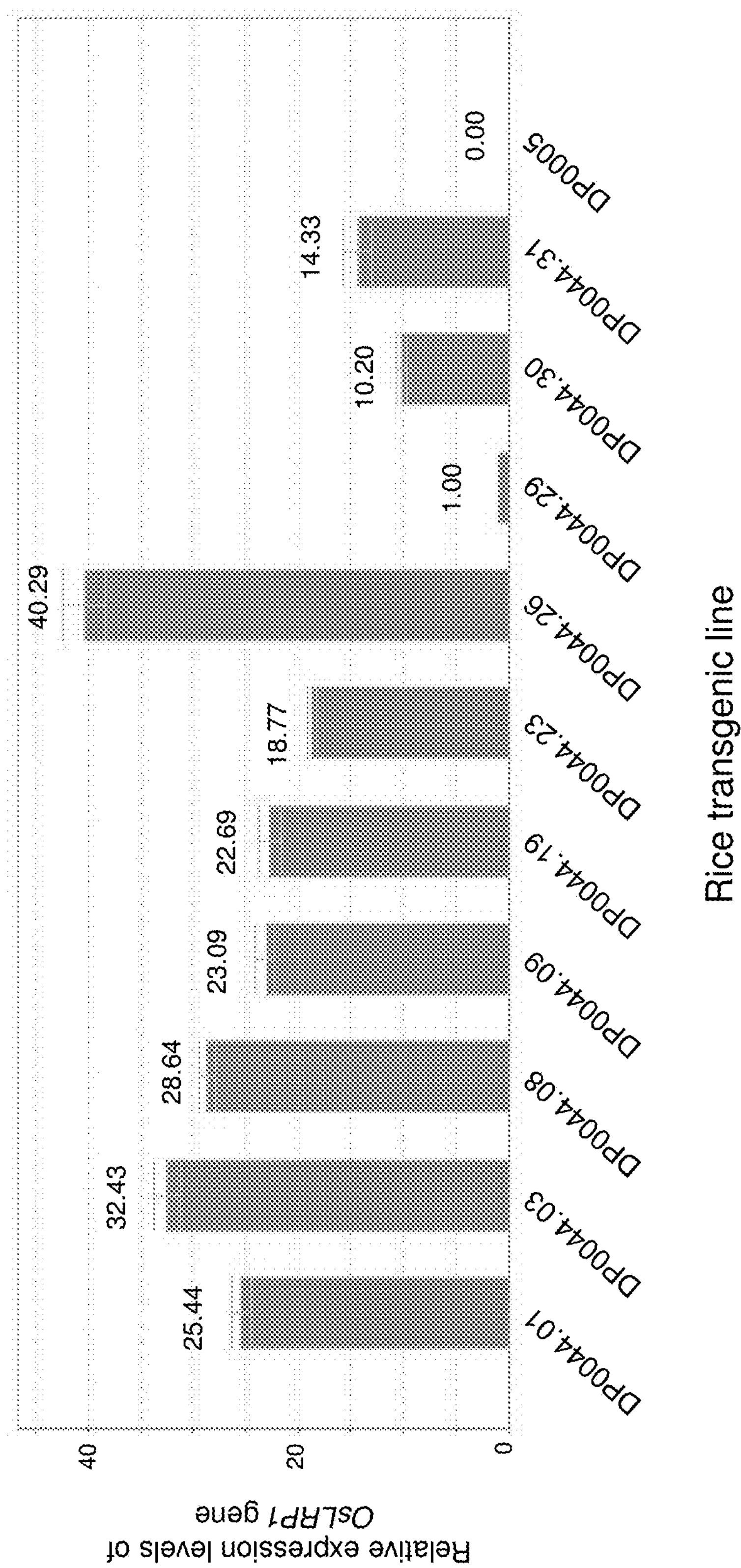
FIG. 1 shows the relative expression levels of OsLRP1 gene in leaves of different transgenic rice lines by real-time PCR analyses. The base expression level in DP0044.29 is set at 1.00, the numbers on the top of the columns are fold-changes compared to DP0044.29 rice. DP0005 is empty vector transformed ZH11 rice plants.

Table 1. SEQ ID NOs for nucleotide and amino acid sequences provided in the sequence listing Table 2. Rice gene names, Gene IDs (from TIGR) and Construct IDs Table 3. Primers for cloning rice abiotic stress tolerance genes Table 4. PCR reaction mixture for cloning abiotic stress tolerance gene Table 5. PCR cycle conditions for abiotic stress tolerance gene Table 6: Modified Hoagland's nutrient solution for culturing rice Table 7. Low nitrogen assay of OsLRP1 transgenic rice plants under greenhouse low nitrogen conditions (1$^{st}$ experiment)

Table 8. Low nitrogen assay of OsLRP1 transgenic rice plants under greenhouse low nitrogen conditions (2$^{nd}$ experiment, ZH11-TC as control)

Table 9. Low nitrogen assay of OsLRP1 transgenic rice plants under greenhouse low nitrogen conditions (2$^{nd}$ experiment, DP0158 as control)

Table 10. Low nitrogen assay of OsDN-LTP1 transgenic rice plants under greenhouse low nitrogen conditions (1$^{st}$ experiment)

Table 11. Low nitrogen assay of OsDN-LTP1 transgenic rice plants under greenhouse low nitrogen conditions (2$^{nd}$ experiment, ZH11-TC as control)

Table 12. Low nitrogen assay of OsDN-LTP1 transgenic rice plants under greenhouse low nitrogen conditions (2$^{nd}$ experiment, DP0158 as control)

Table 13. Low nitrogen assay of OsDN-LTP1 transgenic rice plants under greenhouse low nitrogen conditions (3$^{rd}$ experiment, ZH11-TC as control)

Table 14. Low nitrogen assay of OsDN-LTP1 transgenic rice plants under greenhouse low nitrogen conditions (2$^{nd}$ experiment, DP0158 as control)

Table 15. Chlorate sensitive assay of OsDN-PPR1 transgenic rice seedlings at transgenic line level (1$^{st}$ experiment)

Table 16. Chlorate sensitive assay of OsDN-PPR1 transgenic rice seedlings at transgenic line level (2$^{nd}$ experiment)

Table 17. Chlorate sensitive assay of OsDN-LNP1 transgenic rice seedlings at transgenic line level (1$^{st}$ experiment)

Table 18. Chlorate sensitive assay of OsDN-LNP1 transgenic rice seedlings at transgenic line level (2$^{nd}$ experiment)

Table 19. Chlorate sensitive assay of OsRRM1 rice seedlings at transgenic line level (1$^{st}$ experiment)

Table 20. Chlorate sensitive assay of OsRRM1 rice seedlings at transgenic line level (2$^{nd}$ experiment)

Table 21. Grain yield analysis of OsLRP1 transgenic rice under field low nitrogen condition Table 22. Grain yield analysis of OsLRP1 transgenic rice under field normal nitrogen condition Table 23. Biomass analysis of OsLRP1 transgenic rice under low nitrogen condition Table 24. Plant height analysis of OsLRP1 transgenic rice under low nitrogen condition Table 25. Plant height analysis of OsLRP1 transgenic rice under normal nitrogen condition Table 26. Grain yield analysis of OsRRM1 transgenic rice under field low nitrogen condition Table 27. Grain yield analysis of OsRRM1 transgenic rice under field normal nitrogen condition Table 28. Flag leaf SPAD value analysis of OsRRM1 transgenic rice under field low nitrogen condition Table 29. Top second leaf SPAD value analysis of OsRRM1 transgenic rice under field low nitrogen condition Table 30. Paraquat tolerance assay of OsDN-LNP1 transgenic rice plants at transgenic line level (1$^{st}$ experiment)

Table 31. Paraquat tolerance assay of OsDN-LNP1 transgenic rice plants at transgenic line level (2$^{nd}$ experiment)

Table 32. Grain yield analysis of OsDN-LNP1 transgenic rice plants under field drought conditions Table 33. Modified Hoagland's nutrient solution for culturing *Arabidopsis*

Table 34. P values for green leaf area and greenness evaluated for the over-expression OsDN-PPR1 on 4 consecutive days under low nitrogen condition Table 35. P values for green leaf area and greenness evaluated for the over expression OsRRM1 on 4 consecutive days under low nitrogen condition Sequence Identification

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial | DP0005 vector | 1 | n/a |
| Artificial | pBC-Yellow | 2 | n/a |
| Artificial | DsRED expression cassette | 3 | n/a |
| *Oryza sativa* | OsDN-PPR1 | 4, 5 | 6 |
| *Oryza sativa* | OsLRP1 | 7, 8 | 9 |
| *Oryza sativa* | OsDN-LTP1 | 10, 11 | 12 |
| *Oryza sativa* | OsRRM1 | 13, 14 | 15 |
| Artificial | Primers | 16-27 | n/a |

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of vector DP0005.

SEQ ID NO: 2 is the nucleotide sequence of the pBC-yellow vector.

SEQ ID NO: 3 is the nucleotide sequence of DsRed expression cassette.

SEQ ID NO: 4 is the nucleotide sequence of cDNA of OsDN-PPR1.

SEQ ID NO: 5 is the nucleotide sequence of CDS of OsDN-PPR1.

SEQ ID NO: 6 is the amino acid sequence of OsDN-PPR1.

SEQ ID NO: 7 is the nucleotide sequence of cDNA of OsLRP1.

SEQ ID NO: 8 is the nucleotide sequence of CDS of OsLRP1.

SEQ ID NO: 9 is the amino acid sequence of OsLRP1.

SEQ ID NO: 10 is the nucleotide sequence of gDNA of OsDN-LTP1.

SEQ ID NO: 11 is the nucleotide sequence of CDS of OsDN-LTP1.

SEQ ID NO: 12 is the amino acid sequence of OsDN-LTP1.

SEQ ID NO: 13 the nucleotide sequence of cDNA of OsRRM1.

SEQ ID NO: 14 the nucleotide sequence of CDS of OsRRM1.

SEQ ID NO: 15 is the amino acid sequence of OsRRM1.

SEQ ID NO: 16 is forward primer for cloning cDNA of OsDN-PPR1.

SEQ ID NO: 17 is reverse primer for cloning cDNA of OsDN-PPR1.

SEQ ID NO: 18 is forward primer for cloning cDNA of OsLRP1.

SEQ ID NO: 19 is reverse primer for cloning cDNA of OsLRP1.

SEQ ID NO: 20 is forward primer for cloning gDNA of OsDN-LNP1.

SEQ ID NO: 21 is reverse primer for cloning gDNA of OsDN-LNP1.

SEQ ID NO: 22 is forward primer for cloning cDNA of OsRRM1.

SEQ ID NO: 23 is reverse primer for cloning cDNA of OsRRM1.

SEQ ID NO: 24 is forward primer for real-time RT-PCR analysis of OsLRP1 gene.

SEQ ID NO: 25 is reverse primer for real-time RT-PCR analysis of OsLRP1 gene

SEQ ID NO: 26 is forward primer for real-time RT-PCR analysis of OsDN-LTP1 gene.

SEQ ID NO: 27 is reverse primer for real-time RT-PCR analysis of OsDN-LTP1 gene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "OsDN-PPR1 (Pentatricopeptide Repeat)" refers to a rice polypeptide that confers a low nitrogen tolerance phenotype and is encoded by the rice gene locus LOC_Os11g10740.1 "DN-PPR1 polypeptide" refers herein to the OsDN-PPR1 polypeptide and its homologs from other organisms.

The OsDN-PPR1 polypeptide (SEQ ID NO: 6) is encoded by the coding sequence (CDS) (SEQ ID NO: 5) or nucleotide sequence (SEQ ID NO: 4) at rice gene locus LOC_Os11g10740.1. This polypeptide which has four pentatricopeptide repeat (PPR repeat) domains, is annotated as "tetratricopeptide-like helical, putative" in TIGR (the internet at rice.plantbiology.msu.edu/index.shtml), and "tetratricopeptide-like helical domain containing protein/pentatricopeptide, putative" in NCBI (on the world web at ncbi.nlm.nih.gov/), however does not have any prior assigned function.

The term "OsLRP1 (Leucine Rich Repeat)" refers to a rice polypeptide that confers a low nitrogen tolerance phenotype and is encoded by the rice gene locus LOC_Os11g10720.1. "LRP1 polypeptide" refers herein to the OsLRP1 polypeptide and its homologs from other organisms.

The OsLRP1 polypeptide (SEQ ID NO: 9) is encoded by the coding sequence (CDS) (SEQ ID NO: 8) or nucleotide sequence (SEQ ID NO: 7) at rice gene locus LOC_Os11g10720.1. This polypeptide is annotated as "Cf2/Cf5 disease resistance protein, putative" in TIGR and "Leucine Rich Repeat family protein" in NCBI, however does not have any prior assigned function.

The term "OsDN-LTP1 (Low nitrogen Tolerance Protein)" refers to a rice polypeptide that confers a low nitrogen tolerance phenotype. "DN-LTP1 polypeptide" refers herein to the OsDN-LTP1 polypeptide and its homologs from other organisms. The OsDN-LTP1 polypeptide (SEQ ID NO: 12) is encoded by the coding sequence (CDS) (SEQ ID NO: 11) or nucleotide sequence (SEQ ID NO: 10)

The term "OsRRM1 (RNA Recognition Motif)" refers to a rice polypeptide that confers a low nitrogen tolerance phenotype and is encoded by the rice gene locus LOC_Os06g50890.1. "RRM1 polypeptide" refers herein to the OsRRM1 polypeptide and its homologs from other organisms.

The OsRRM1 polypeptide (SEQ ID NO: 15) is encoded by the coding sequence (CDS) (SEQ ID NO: 14) or nucleotide sequence (SEQ ID NO: 13) at rice gene locus LOC_Os06g50890.1. This polypeptide is annotated as "RNA recognition motif containing protein, expressed" in TIGR and "putative transformer-SR ribonucleoprotein" in NCBI, however does not have any prior assigned function.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristics of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristics" is a measurable parameter including but not limited to, greenness, yield, growth rate, biomass, fresh weight, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length, early seedling vigor, and seedling emergence under low temperature stress.

"Harvest index" refers to the grain weight divided by the total plant weight.

Increased biomass can be measured, for example, as an increase in plant height, plant total leaf area, plant fresh weight, plant dry weight or plant grain yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products.

Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including nutrient deprivation and/or water deprivation, because larger roots may better reach or take up nutrients and/or water.

"Environmental conditions" refer to conditions under which the plant is grown, such as the availability of water, availability of nutrients (for example nitrogen), or the presence of insects or disease.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

The terms "nitrogen stress tolerance", "low nitrogen tolerance" and "nitrogen deficiency tolerance" are used interchangeably herein, which indicate a trait of a plant and refer to the ability of the plant to survive under nitrogen limiting conditions or low nitrogen conditions.

"Increased nitrogen stress tolerance" of a polypeptide indicates that over-expression of the polypeptide in a transgenic plant confers increased nitrogen stress tolerance of the transgenic plant relative to a reference or control plant.

"Increased nitrogen stress tolerance" of a plant is measured relative to a reference or control plant, reflects ability of the plant to survive and/or grow better under nitrogen limiting conditions, and means that the nitrogen stress tolerance of the plant is increased by any amount or measured when compared to the nitrogen stress tolerance of the reference or control plant.

A "nitrogen stress tolerant plant" is a plant that exhibits nitrogen stress tolerance. A nitrogen stress tolerant plant can be a plant that exhibits an increase in at least one agronomic characteristic relative to a control plant under nitrogen limiting conditions.

"NUE" is nitrogen utilization efficiency and refers to a plant's ability to utilize nitrogen in low or high levels of fertilizer. It reflects the plant's ability to uptake, assimilate, and/or otherwise utilize nitrogen.

Soil plant analyses development (SPAD) value is SPAD reading which is measured by SPAD-502 plus (a chlorophyll meter, made by KONICA MINOLTA). The SPAD value is relative content of leaf chlorophyll and an important indicator of plant health. Many studies indicated that a significant and positive correlation was observed between leaf nitrogen content and SPAD value (Swain D. K. and Sandip S. J. (2010) *Journal of Agronomy* 9 (2):38-44), and leaf SPAD value is used as index of nitrogen status diagnosis in crops (Cai H.-G. et al. (2010) *Acta metallurgica sinica* 16 (4): 866-873).

The response and tolerance of rice plants to low nutrition stress is an integrated and comprehensive physiological and biochemical process. The tolerance of plants will be reflected in different aspect under different plant development phase and different stress conditions. The environment factors such as illumination and temperature are critical factors which effect rice growth, and the variation of these environment factors will influence the growth and development of rice plants. Researchers demonstrated that low nitrogen treated rice plants display low chlorophyll content in leaf, deduced tiller number, or reduced biomass. In our experiment, the leaf color (which can be indicated by chlorophyll, SPAD value), plant fresh weight, and tiller number are measured, and the low nitrogen tolerance plants are selected by combining the three parameters.

"Chlorate" refers to a chemical compound containing chlorate anion, a salt of chloric acid. It is a nitrate analog which can be uptake by plant with same transport system like nitrate, and then converted by nitrate reductase to chlorite which is toxic and leads to plant damage, withering, and plant death. Potassium chlorate is used in this disclosure.

"Chlorate sensitivity" is a trait of plant, reflects the level of damage, even death after chlorate uptake, transport or reduction when treated with chlorate solution, compared to a reference or control plant.

"Increased Chlorate sensitivity" of a plant is measured relative to a reference or control plant, and reflects higher ability of the plant to chlorate or nitrate uptake, transport or reduce than a reference or control plant in chlorate or nitrate solution. In general, chlorate sensitivity can be used as a marker of NUE. The more sensitive plants are to chlorate, the higher the NUE.

"Chlorate sensitive seedlings" are the damaged seedlings with phenotype of withered leaves in whole and without green leaf, and considered as dead after treated with chlorate solution.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-TC, line null, and empty vector plants indicate control plants. ZH11-TC represents rice plants generated from tissue cultured Zhonghua 11, line null represents segregated null plants, and empty vector represents plants transformed with empty vector DP0005 or DP0158.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. The heterologous polynucleotide can be stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenine or deoxyadenine (for RNA or DNA, respectively), "C" for cytosine or deoxycytosine, "G" for guanine or deoxyguanine, "U" for uracil, "T" for thymine or deoxythymine, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring improved nitrogen use efficiency and/or enhanced drought tolerance, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is preferably a DN-PPR1, LRP1, DN-LTP1 or RRM1. Over-expression of these polypeptide preferably increase plant low nitrogen tolerance activity and/or drought tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15. The polypeptide is preferably an OsDN-PPR1, OsLRP1, OsDN-LTP1 or OsRRM1 polypeptide.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 4, 5, 7, 8, 10, 11, 13 or 14; or (ii) a full complement of the nucleic acid sequence of (i). Any of the foregoing isolated polynucleotides may be utilized in any recombinant DNA constructs of the present disclosure. The isolated polynucleotide preferably encodes a DN-PPR1, LRP1, DN-LTP1 or RRM1 protein. Over-expression of this polypeptide preferably increase plant low nitrogen tolerance activity and/or drought tolerance activity.

Recombinant DNA Constructs

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 4, 5, 7, 8, 10, 11, 13 or 14; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a DN-PPR1, LRP1, DN-LTP1 or RRM1 protein. These polypeptides preferably have low nitrogen tolerance activity and/or drought tolerance activity, and may be from, for example, *Oryza sativa,*

*Arabidopsis thaliana, Zea mays, Glycine max, Glycine tabacina, Glycine soja* or *Glycine tomentella.*

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing", as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on over-expression of a nucleic acid sequence having homology to a native mRNA, in the sense orientation, which results in the reduction of all RNA having homology to the over-expressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294:858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct (including a suppression DNA construct) of the present disclosure may comprise at least one regulatory sequence.

A regulatory sequence may be a promoter.

A number of promoters can be used in recombinant DNA constructs (and suppression DNA constructs) of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current disclosure include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228 (1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156 (2):155-166 (1995); NCBI GenBank Accession No. X80206)). Zag2 transcripts can be detected five days prior to pollination to seven to eight days after pollination ("DAP"), and directs expression in the carpel of developing female inflorescences and Ciml which is specific to the nucleus of developing maize kernels. Ciml transcript is detected four to five days before pollination to six to eight DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp. (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize led promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1B10 promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs (and suppression DNA constructs) of the present disclosure may also include other regulatory sequences including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions

A composition of the present disclosure is a plant comprising in its genome any of the recombinant DNA constructs (including any of the suppression DNA constructs) of the present disclosure (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under nitrogen limiting conditions), or used in a breeding program to produce hybrid seed, which can be grown to produce plants that would exhibit such an altered agronomic characteristic. The seeds may be maize seeds, or rice seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A plant (for example, a rice, maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; and wherein said plant exhibits increased nitrogen stress tolerance and/or drought tolerance when compared to a control plant not comprising said recombinant DNA construct. The plant may further exhibit an alteration of at least one agronomic characteristic when compared to the control plant.

2. A plant (for example, a rice, maize or soybean plant) comprising in its genome a recombinant DNA construct comprising a polynucleotide operably linked to at least one regulatory sequence, wherein said polynucleotide encodes a DN-PPR1, LRP1, DN-LTP1 or RRM1 polypeptide, and wherein said plant exhibits increased nitrogen stress tolerance and/or drought tolerance when compared to a control plant not comprising said recombinant DNA construct. The plant may further exhibit an alteration of at least one agronomic characteristic when compared to the control plant. The DN-PPR1, LRP1, DN-LTP1 or RRM1 polypeptide may be from *Arabidopsis thaliana, Zea mays, Glycine max, Glycine tabacina, Glycine soja* or *Glycine tomentella.*

3. A plant (for example, a rice, maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15, and wherein said plant exhibits an alteration of at least one agronomic characteristic under nitrogen limiting conditions when compared to a control plant not comprising said recombinant DNA construct.

4. Any progeny of the above plants in embodiment 1-3, any seeds of the above plants in embodiment 1-3, any seeds of progeny of the above plants in embodiment 1-3, and cells from any of the above plants in embodiment 1-3 and progeny thereof.

In any of the foregoing embodiment 1-4 or any other embodiments of the present disclosure, the recombinant DNA construct may comprises at least a promoter functional in a plant as a regulatory sequence.

In any of the foregoing embodiment 1-4 or any other embodiments of the present disclosure, the alteration of at least one agronomic characteristic is either an increase or decrease.

In any of the foregoing embodiment 1-4 or any other embodiments of the present disclosure, the at least one agronomic characteristic is may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear length, early seedling vigor, and seedling emergence under low temperature stress. For example, the alteration of at least one agronomic characteristic may be an increase in yield, greenness, plant height or biomass.

In any of the foregoing embodiment 1-4 or any other embodiments of the present disclosure, the plant may exhibit the alteration of at least one agronomic characteristic when compared, under nitrogen stress conditions, to a control plant not comprising said recombinant DNA construct.

In any of the foregoing embodiment 1-4 or any other embodiments of the present disclosure, the plant may exhibit the alteration of at least one agronomic characteristic when compared, under drought stress conditions, to a control plant not comprising said recombinant DNA construct.

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The examples below describe some representative protocols and techniques for simulating nitrogen limiting conditions and/or evaluating plants under such conditions, simulating drought conditions and/or evaluating drought tolerance; and simulating oxidative stress conditions.

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

SPAD value can be measured during low or high nitrogen condition in the field and greenhouse test by a chlorophyll meter. The SPAD value is a parameter indicating the plant health, and reflects plant nitrogen content by predicting the chlorophyll content. The plants with higher low nitrogen tolerance will have higher SPAD value compared to a control or reference plant.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

One of ordinary skill in the art would readily recognize a suitable control or reference plant to be utilized when assessing or measuring an agronomic characteristic or phenotype of a transgenic plant in any embodiment of the present disclosure in which a control is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or the suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for increasing chlorate sensitive in a plant, methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, and methods for producing seed. The plant may be a monocotyledonous or dicotyledonous plant, for example, a rice, maize, *Arabidopsis*, soybean plant. The plant may also be sunflower, sorghum, canola, wheat, alfalfa, cotton, barley or millet. The seed may be a rice, maize, *Arabidopsis* or soybean seed, for example a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing nitrogen stress tolerance and/or chlorate sensitivity in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; and (b) regenerating a transgenic plant from the regenerable plant cell after step (a), wherein the transgenic plant comprises in its genome the recombinant DNA construct and exhibits increased nitrogen stress tolerance and/or chlorate sensitivity when compared to a control plant not comprising the recombinant DNA construct. The method may further comprise (c) obtaining a progeny plant derived from the transgenic plant, wherein said progeny plant comprises in its genome the recombinant DNA construct and exhibits increased nitrogen stress tolerance and/or chlorate sensitivity when compared to a control plant not comprising the recombinant DNA construct.

A method of evaluating nitrogen stress tolerance and/or chlorate sensitivity in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; (b) regenerating a transgenic plant from the regenerable plant cell after step (a), wherein the transgenic plant comprises in its genome the recombinant DNA construct; and (c) evaluating the transgenic plant for nitrogen stress tolerance and/or chlorate sensitivity compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance and/or chlorate sensitivity compared to a control plant not comprising the recombinant DNA construct.

A method of increasing drought stress tolerance and/or paraquat tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 12; and (b) regenerating a transgenic plant from the regenerable plant cell after step (a), wherein the transgenic plant comprises in its genome the recombinant DNA construct and exhibits increased drought stress tolerance and/or paraquat tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance and/or paraquat tolerance when compared to a control plant not comprising the recombinant DNA construct.

A method of evaluating drought stress tolerance and/or paraquat tolerance in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 12; (b) regenerating a transgenic plant from the regenerable plant cell after step (a), wherein the transgenic plant comprises in its genome the recombinant DNA construct; and (c) evaluating the transgenic plant for drought stress tolerance and/or paraquat tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for drought stress tolerance and/or paraquat tolerance compared to a control plant not comprising the recombinant DNA construct.

A method of determining an alteration of an agronomic characteristic in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 6, 9, 12 or 15; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared, optionally under nitrogen limiting conditions and/or drought stress conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared, optionally under nitrogen limiting conditions, to a control plant not comprising the recombinant DNA construct.

A method of producing seed (for example, seed that can be sold as a nitrogen stress tolerant product offering) comprising any of the preceding methods, and further comprising obtaining seeds from said progeny plant, wherein said seeds comprise in their genome said recombinant DNA construct.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, in said introducing step said regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the at least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. The alteration of at least one agronomic characteristic may be an increase in yield, greenness, plant height or biomass.

In any of the preceding methods or any other embodiments of methods of the present disclosure, the plant may exhibit the alteration of at least one agronomic characteristic when compared, under nitrogen stress conditions and/or drought stress conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" or engineered endonucleases such as meganucleases produced to modify plant genomes (see e.g., WO 2009/114321; Gao et al. (2010) Plant Journal 1:176-187). Another site-directed engineering is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristic of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Cloning and Over-Expression Vector Construction of Abiotic Stress Tolerance Genes Based on preliminary screening of rice activation tagging population and the sequences information of gene ID shown in the Table 2, primers were designed for cloning rice genes OsDN-PPR1, OsLRP1, OsDN-LNP1 and OsRRM1. The primers and the expected-lengths of the amplified genes are shown in Table 3.

For OsDN-PPR1, OsLRP1 and OsRRM1, their cDNA were cloned by PCR using pooled cDNA from leaf, stem and root tissues of Zhonghua 11 plant as the template. For OsDN-LNP1, its gDNAs was cloned, and amplified using genomic DNA of Zhonghua 11 as the template. The PCR reaction mixtures and PCR procedures are shown in Table 4 and Table 5.

TABLE 2

| Rice gene names, Gene IDs (from TIGR) and Construct IDs | | |
|---|---|---|
| Gene name | Gene LOC ID | Construct ID |
| OsDN-PPR1 | LOC_Os11g10740 | DP0039 |
| OsLRP1 | LOC_Os11g10720 | DP0044 |
| OsDN-LTP1 | LOC_Os05g41259 | DP0047 |
| OsRRM1 | LOC_Os06g50890 | DP0049 |

TABLE 3

| Primers for cloning rice abiotic stress tolerance genes | | | | |
|---|---|---|---|---|
| Primer | Sequence | SEQ ID NO: | Gene name | Length of amplified fragment (bp) |
| gc-408 | 5'-GAGCGAACTGCTTGGTTGGGAATG-3' | 16 | OsDN-PPR1 | 1444 |
| gc-409 | 5'-CCCAAAGCATTCATCTCCTCAAATAACG-3 | 17 | | |
| gc-403 | 5'-CGAATGGCCGGCAATGTCATCC-3' | 18 | OsLRP1 | 2315 |
| gc-404 | 5'-AGTACCTATTAATCTGTGGTAGCCTCTC-3' | 19 | | |
| gc-571 | 5'-CCAGGCTACTACTAGTACTCTACCAAC-3' | 20 | OsDN-LTP1 | 749 |
| gc-572 | 5'-CTACGGAGTATATCATTAGATTCACGCTG-3' | 21 | | |
| gc-211 | 5'-GAGACCGAGAGAGAGAAGCAGCACC-3' | 22 | OsRRM1 | 949 |
| gc-214 | 5'-GGGAGCAACCTTACCTGTCATAGCC-3' | 23 | | |

TABLE 4

| PCR reaction mixture for cloning abiotic stress tolerance gene | |
|---|---|
| Reaction mix | 50 μL |
| Template | 1 μL |
| TOYOBO KOD-FX (1.0 U/μL) | 1 μL |
| 2×PCR buffer for KOD-FX | 25 μL |
| 2 mM dNTPs (0.4 mM each) | 10 μL |
| Primer-F/R (10 μM) | 2 μL each |
| $ddH_2O$ | 9 μL |

TABLE 5

| PCR cycle conditions for abiotic stress tolerance gene | | |
|---|---|---|
| 94° C. | 3 min | |
| 98° C. | 10 s | ×30 |
| 58° C. | 30 s | |
| 68° C. | (1 Kb/min) 1 min | |
| 68° C. | 5 min | |

The PCR amplified products were extracted from the agarose gel after the electrophoresis and purified using a column kit and then ligated with TA cloning vectors. The sequences and orientation in these constructs were confirmed by DNA sequencing. Then these genes were cloned into plant binary construct DP0005 (pCAMBIA1300-AsRed) (SEQ ID NO: 1). The generated over-expression vectors were listed in Table 2. The cloned nucleotide sequence in construct of DP0039 and coding sequence of OsDN-PPR1 are provided as SEQ ID NO: 4 and 5, the encoded amino acid sequence of OsDN-PPR1 is SEQ ID NO: 6; the cloned nucleotide sequence in construct of DP0044 and coding sequence of OsLRP1 are provided as SEQ ID NO: 7 and 8, the encoded amino acid sequence of OsLRP1 is SEQ ID NO: 9; the cloned nucleotide sequence in construct of DP0047 and coding sequence of OsDN-LNP1 are provided as SEQ ID NO: 10 and 11, the encoded amino acid sequence of OsDN-LNP1 is SEQ ID NO: 12; and the cloned nucleotide sequence in construct of DP0049 and coding sequence of OsRRM1 are provided as SEQ ID NO: 13 and 14, the encoded amino acid sequence of OsRRM1 is SEQ ID NO: 15.

DsRed gene expression cassette (SEQ ID NO: 3 in the sequence list) was transfer to the plant binary construct DP0005 to generate another empty vector DP0158.

Example 2

Transformation for Transgenic Rice Lines

In this research, all of the over-expression vectors and empty vector (DP0005 and DP0158) were transformed into the Zhonghua 11 (*Oryza sativa* L.) by *Agrobacteria*-mediated method as described by Lin and Zhang ((2005) *Plant Cell Rep.* 23:540-547). Zhonghua 11 was cultivated by institute of crop sciences, Chinese Academy of Agricultural Sciences. The first batch of seeds used in this research was provided by Beijing Weiming Kaituo Agriculture Biotech Co., Ltd. Calli induced from embryos was transformed with *Agrobacteria* with the vector. The transgenic seedlings ($T_0$) generated in transformation laboratory were transplanted in the field to get $T_1$ seeds. The $T_1$ and $T_2$ seeds were stored at cold room (4° C.), and $T_2$ seeds were used for following trait screening.

$T_1$ transgenic plants were selected by hygromycin by culturing the rice plants (from 1-2 cm in height) in 50 mg/L hygromycin solution, the survived plants (hygromycin-resistant) were planted in field to produce $T_2$ seeds. Only the hygromycin-resistant $T_2$ transgenic rice was used in trait screen.

Example 3

Gene Expression Analysis

Transgene expression levels of the genes in the transgenic rice plants were analyzed. A standard RT-PCR or a real-time PCR procedure, such as the QuantiTect® Reverse Transcription Kit from Qiagen® and Real Time-PCR(SYBR®Premix Ex Taq™, TaKaRa), was used. EF1α gene was used as an internal control to show that the amplification and loading of samples from the transgenic rice and wild-type were similar. Gene expression was normalized based on the EF1α mRNA levels.

As shown in FIG. 1, the expression level of OsLRP1 gene in DP0044.29 rice is set at 1.00, OsLRP1 over-expressed in all the ten lines, and no expression was detected in empty vector transformed plants (DP0005).

```
                                          (SEQ ID NO: 24)
DP0044-1:       5'-CTCCCATCATTTCTCCGCAACTC-3'

                                          (SEQ ID NO: 25)
DP0044-2:       5'-CCAAGAGACCCATCCACAACGTC-3'
```

Figure 2:
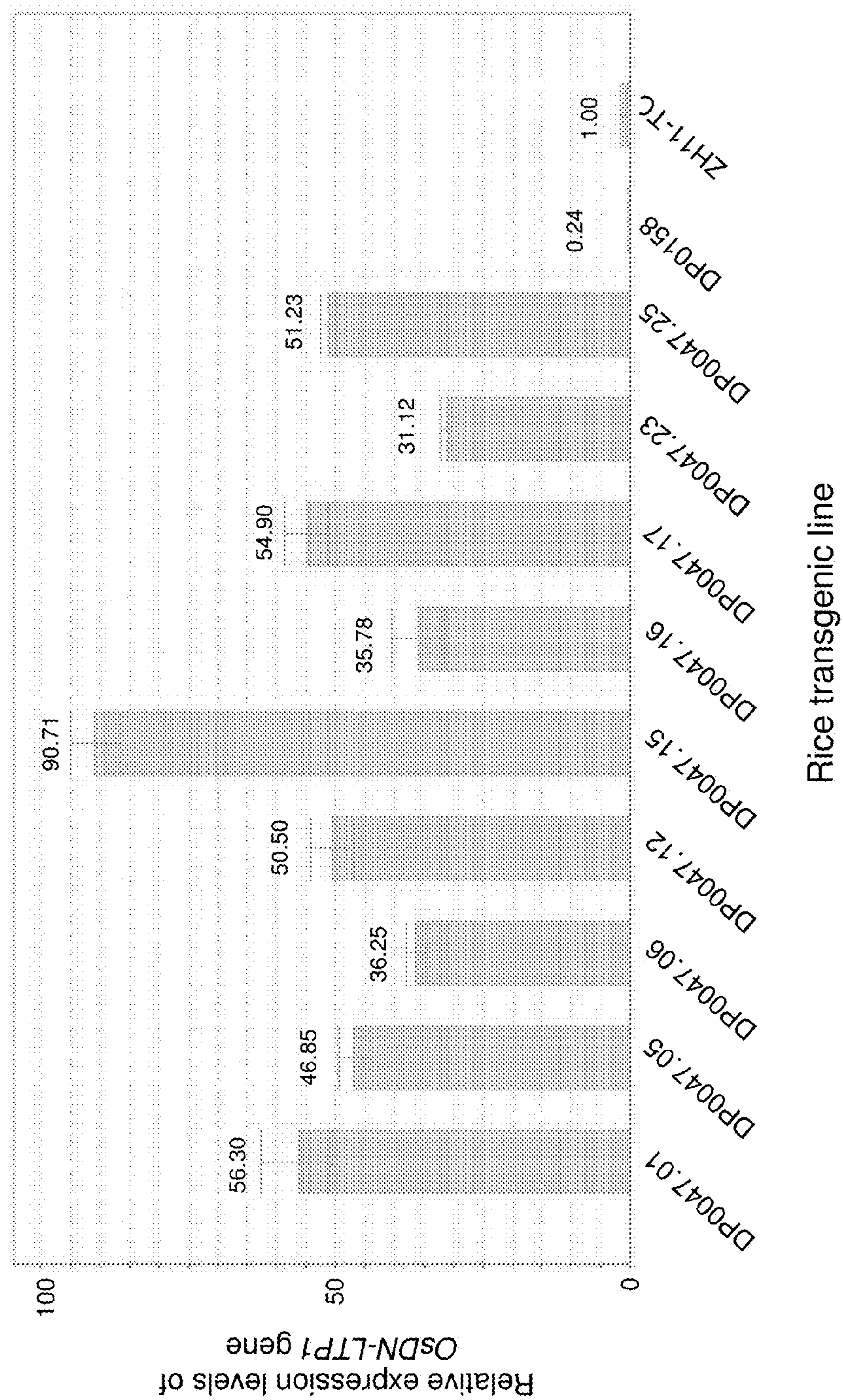
FIG. 2 shows the relative expression levels of OsDN-LTP1 gene in leaves of different transgenic rice lines by real-time PCR analyses. The base expression level in ZH11-TC is set at 1.00, the numbers on the top of the columns are fold-changes compared to ZH11-TC rice.

As shown in FIG. 2. OsLTP1 over-expressed in all the tested lines, while the expression levels of OsLTP1 were very low in the both controls of ZH11-TC and DP0158 seedlings.

```
                                          (SEQ ID NO: 26)
DP0047-F1:      5'-GTGCGCATTAAAGAAATTCA-3'

                                          (SEQ ID NO: 27)
DP0047-R1:      5'-TCACGCTGACAACACTTTC-3'
```

Example 4

Greenhouse NUE Screening of Transgenic Rice Plants

In order to investigate whether the genes could improve low nitrogen tolerance or nitrogen use efficiency (NUE) in rice plants, the transgenic rice plants were screened in greenhouse low nitrogen assays. In the greenhouse, two types of lamps are provided as light source, i.e. sodium lamp and metal halide lamp, the ratio is 1:1. Lamps provide the 16 h/8 h period of day/night, and are placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C.

NUE Screening Method:

Transgenic $T_2$ seeds were sterilized by 800 ppm carbendazol for 8 h at 32° C. and washed 3-5 times, then soaked in water for 16 h at 32° C., germinated for 18 h at 35-37° C. in an incubator. The germinated seeds were selected and planted in pot filled with vermiculite. Randomized block design was used in this trait screen. Every screen unit has 4 blocks which include 2 controls (ZH11-TC and empty vector, or line null) and 4 transgenic lines. 8 seedlings of each transgenic line were planted in 4 pots and located in different positions of the 4 blocks. 9-12 transgenic lines of each gene were screened.

After cultured for 7-10 days, water was replaced by modified Hoagland solution containing 0.75 mM nitrogen ($KNO_3$) (Table 6). To make aerobic condition, the nutrition solution was drained off every Monday, Wednesday, and Friday for 2-3 h, and then new modified Hoagland containing low nitrogen solution was added. After cultured in low nitrogen solution for 35-40 days, tiller (including the stem and all tillers) numbers were counted, SPAD value was measured by a SPAD meter (SPAD 502 Plus, made by KONICA MINOLTA) with three different positions of the second leaf from the top, and the SPAD value was the average of three readings; and, the fresh weight of the seedlings (cutting from the joint of root and stem) was measured by one percent of the balance. After statistical analysis of these data (tiller number, SPAD value and fresh weight), the positive lines were selected by a cut-off of $P<0.05$.

TABLE 6

Modified Hoagland's nutrient solution for culturing rice

| Molecular formula | Mass concentration (g/L) |
|---|---|
| $KH_2PO_4$ | 34.38 |
| $MgSO_4 \cdot 7H_2O$ | 246.50 |
| $CaCl_2 \cdot 2H_2O$ | 146.88 |
| KCl | 242.29 |
| $KNO_3$ | 101.00 |
| $Na_2SiO_3 \cdot 9H_2O$ | 142.00 |
| $H_3BO_3$ | 1.85 |
| $MnCl_2 \cdot 4H_2O$ | 1.98 |
| $ZnSO_4 \cdot 7H_2O$ | 2.87 |
| $CuSO_4 \cdot 5H_2O$ | 0.25 |
| $(NH_4)_6MoO_{24} \cdot 2H_2O$ | 0.24 |
| EDTA-2Na | 7.45 |
| $FeSO_4 \cdot 7H_2O$ | 5.57 |

NUE Screening Results

1) Validation Results for OsLRP1(DP0044) Transgenic Rice

For OsLRP1 transgenic rice plants, 12 transgenic lines were tested, their line null was used as controls in the first experiment. As shown in Table 7, five lines had greater average tiller numbers, SPAD values and fresh weights than their corresponding controls. Two transgenic lines (DP0044.26 and DP0046.30) showed better for these three parameters. Ten lines exhibited greater tiller numbers. These results demonstrate that the OsLRP1 transgenic rice plants may have enhanced low nitrogen tolerance or improved NUE.

TABLE 7

Low nitrogen assay of OsLRP1 transgenic rice plants under greenhouse low nitrogen conditions (1st experiment)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0044.01 | 1.4 | 0.1036 | | 34.68 | 0.9082 | | 2.886 | 0.3677 | |
| DP0044.01-Null | 1.9 | | | 34.39 | | | 3.663 | | |
| DP0044.03 | 1.1 | 0.5950 | | 28.27 | 0.8332 | | 2.230 | 0.7339 | |
| DP0044.03-Null | 1.0 | | | 27.36 | | | 2.520 | | |
| DP0044.05 | 1.6 | 0.2275 | | 34.83 | 0.0046 | Y | 4.098 | 0.0815 | |
| DP0044.05-Null | 1.1 | | | 28.45 | | | 2.483 | | |
| DP0044.07 | 1.5 | 0.1970 | | 34.65 | 0.2418 | | 3.954 | 0.2267 | |
| DP0044.07-Null | 1.1 | | | 33.09 | | | 3.385 | | |

TABLE 7-continued

Low nitrogen assay of OsLRP1 transgenic rice plants under greenhouse low nitrogen conditions (1st experiment)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0044.08 | 1.4 | 0.1705 | | 31.80 | 0.2886 | | 3.233 | 0.6395 | |
| DP0044.08-Null | 1.1 | | | 33.70 | | | 3.503 | | |
| DP0044.09 | 1.3 | 1.0000 | | 35.71 | 0.6419 | | 3.585 | 0.3097 | |
| DP0044.09-Null | 1.3 | | | 36.71 | | | 4.465 | | |
| DP0044.19 | 1.1 | 0.3506 | | 38.71 | 0.6400 | | 5.076 | 0.6136 | |
| DP0044.19-Null | 1.3 | | | 38.26 | | | 4.871 | | |
| DP0044.23 | 1.0 | 1.0000 | | 32.90 | 0.3230 | | 3.521 | 0.4135 | |
| DP0044.23-Null | 1.0 | | | 35.66 | | | 4.073 | | |
| DP0044.26 | 1.4 | 0.0796 | | 36.54 | 0.0555 | | 5.174 | 0.0376 | Y |
| DP0044.26-Null | 1.0 | | | 34.69 | | | 3.646 | | |
| DP0044.29 | 1.0 | 1.0000 | | 31.58 | 0.0119 | | 2.559 | 0.0137 | |
| DP0044.29-Null | 1.0 | | | 35.74 | | | 3.866 | | |
| DP0044.30 | 1.5 | 0.0796 | | 36.75 | 0.0160 | Y | 4.566 | 0.0122 | Y |
| DP0044.30-Null | 1.1 | | | 30.95 | | | 2.664 | | |
| DP0044.31 | 1.5 | 0.1970 | | 36.99 | 0.1411 | | 4.624 | 0.0205 | Y |
| DP0044.31-Null | 1.1 | | | 34.03 | | | 3.640 | | |

In the second experiment, ten lines were tested, ZH11-TC and DP0158 seedlings were used as controls, and randomized block design was used. Twelve rice plants from each transgenic line, ZH11-TC and DP0158 were planted in one container, repeated twice. When the rice plants grew to 3-leaf stage, Hoagland solution containing 0.75 mM potassium nitrate was applied to these plants. After low nitrogen stressed for 34 days, tiller number, SPAD value and fresh weight were measured. The average tiller number of all the OsLRP1 transgenic rice was significantly greater than that of ZH11-TC (P value=0.0408) and greater than that of DP0158 (P value=0.1009) control; the average SPAD value of OsLRP1 transgenic rice was greater than that of ZH11-TC and DP0158 controls; and the average fresh weight of OsLRP1 transgenic rice was greater than that of ZH11-TC and DP0158 at construct level.

As shown in Table 8, nine lines exhibited greater tiller number, six lines exhibited greater SPAD value than ZH11-TC control. As shown in Table 9, nine lines exhibited greater tiller number, eight lines exhibited greater SPAD value, and ten lines exhibited fresh weight than DP0158 control. These results demonstrate OsLRP1 transgenic rice obtained enhanced low nitrogen tolerance or improved NUE, and over-expression of OsLRP1 enhances NUE of transgenic plants.

TABLE 8

Low nitrogen assay of OsLRP1 transgenic rice plants under greenhouse low nitrogen conditions (2nd experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0044.01 | 1.7 | 0.0952 | | 35.05 | 0.6052 | | 3.160 | 0.9425 | |
| DP0044.05 | 1.8 | 0.0190 | Y | 35.56 | 0.3455 | | 3.474 | 0.2687 | |
| DP0044.07 | 1.7 | 0.0952 | | 34.62 | 0.8791 | | 3.313 | 0.6155 | |
| DP0044.08 | 1.8 | 0.0381 | Y | 33.61 | 0.4931 | | 3.137 | 0.8723 | |
| DP0044.09 | 2.1 | 0.0010 | Y | 36.27 | 0.1244 | | 3.533 | 0.1830 | |
| DP0044.19 | 1.6 | 0.1251 | | 35.38 | 0.4300 | | 3.328 | 0.5766 | |
| DP0044.26 | 1.4 | 0.5569 | | 32.53 | 0.1125 | | 2.921 | 0.3308 | |
| DP0044.29 | 1.3 | 0.9296 | | 34.00 | 0.7195 | | 3.135 | 0.8676 | |
| DP0044.30 | 1.6 | 0.1620 | | 32.39 | 0.0877 | | 2.961 | 0.4117 | |
| DP0044.31 | 2.1 | 0.0002 | Y | 35.17 | 0.5372 | | 3.451 | 0.3071 | |
| ZH11-TC | 1.3 | | | 34.43 | | | 3.180 | | |
| DP0044 (construct) | 1.7 | 0.0408 | Y | 34.46 | 0.9805 | | 3.241 | 0.7898 | |

TABLE 9

Low nitrogen assay of OsLRP1 transgenic rice plants under greenhouse low nitrogen conditions (2nd experiment, DP0158 as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0044.01 | 1.7 | 0.1906 | | 35.05 | 0.0526 | | 3.160 | 0.1921 | |
| DP0044.05 | 1.8 | 0.0472 | Y | 35.56 | 0.0181 | Y | 3.474 | 0.0130 | Y |
| DP0044.07 | 1.7 | 0.1906 | | 34.62 | 0.1157 | | 3.313 | 0.0603 | |
| DP0044.08 | 1.8 | 0.0865 | | 33.61 | 0.4619 | | 3.137 | 0.2241 | |
| DP0044.09 | 2.1 | 0.0034 | Y | 36.27 | 0.0031 | Y | 3.533 | 0.0068 | Y |
| DP0044.19 | 1.6 | 0.2405 | | 35.38 | 0.0271 | Y | 3.328 | 0.0530 | |
| DP0044.26 | 1.4 | 0.8200 | | 32.53 | 0.8682 | | 2.921 | 0.6862 | |
| DP0044.29 | 1.3 | 0.6540 | | 34.00 | 0.2882 | | 3.135 | 0.2264 | |
| DP0044.30 | 1.6 | 0.2990 | | 32.39 | 0.7744 | | 2.961 | 0.5784 | |
| DP0044.31 | 2.1 | 0.0008 | Y | 35.17 | 0.0415 | Y | 3.451 | 0.0165 | Y |
| DP0158 | 1.4 | | | 32.73 | | | 2.814 | | |
| DP0044 (construct) | 1.7 | 0.1009 | | 34.46 | 0.1030 | | 3.241 | 0.0653 | |

2) Validation Results for OsDN-LTP1 (DP0047) Transgenic Rice

For OsDN-LTP1 transgenic rice, 12 transgenic lines were tested and ZH11-TC and DP0005 seedlings were used as controls in the first experiment. When the seedlings grew to 3-leaf stage, Hoagland solution containing 0.75 mM potassium nitrate was applied to these plants for 37 days. The average tiller numbers and the fresh weights were greater than that of DP0005 controls. As shown in Table 10, three transgenic seedlings had significantly greater fresh weights and two transgenic lines had significantly greater tiller numbers than DP0005 controls. When compared to ZH11-TC controls, ten transgenic lines showed better tiller numbers. These results indicate that the OsDN-LTP1 transgenic rice plants had enhanced low nitrogen tolerance or improved NUE.

In the second experiment, ten lines were tested, ZH11-TC and DP0158 seedlings were used as controls, and randomized block design was used. Twelve rice plants from each transgenic line, ZH11-TC and DP0158 were planted in one container. When the rice plants grew to 3-leaf stage, Hoagland solution containing 0.75 mM potassium nitrate was applied to these plants. After low nitrogen stressed for 35 days, tiller number, SPAD value and fresh weight were measured. The average tiller number, SPAD value and fresh weight of the OsDN-LTP1 transgenic rice were 1.6, 34.23 and 3.484 respectively. The average SPAD value was significantly greater than ZH11-TC control. All the transgenic lines exhibited greater tiller numbers, SPAD values and fresh weights than either ZH11-TC or DP0158 controls (Table 11 and 12). These results demonstrate OsDN-LTP1 transgenic rice obtained enhanced low nitrogen tolerance or improved NUE, and over-expression of OsDN-LTP1 plays a role in enhancing NUE.

TABLE 10

Low nitrogen assay of OsDN-LTP1 transgenic rice plants under greenhouse low nitrogen conditions (1st experiment)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.01 | 2.6 | 0.3172 | | 38.60 | 0.6139 | | 6.411 | 0.4936 | |
| DP0005 | 2.0 | | | 39.29 | | | 5.940 | | |
| DP0047.03 | 2.6 | 0.0885 | | 37.59 | 0.3849 | | 5.519 | 0.4738 | |
| DP0005 | 1.6 | | | 39.00 | | | 5.021 | | |
| DP0047.06 | 3.0 | 0.0014 | Y | 39.04 | 0.1189 | | 6.489 | 0.0006 | Y |
| DP0005 | 1.3 | | | 36.93 | | | 4.165 | | |
| DP0047.16 | 2.5 | 0.0032 | Y | 36.68 | 0.9947 | | 5.510 | 0.1550 | |
| DP0005 | 1.4 | | | 36.69 | | | 4.553 | | |
| DP0047.17 | 2.1 | 0.1231 | | 34.58 | 0.6115 | | 5.540 | 0.0002 | Y |
| DP0005 | 1.4 | | | 35.19 | | | 3.640 | | |
| DP0047.19 | 2.0 | 0.7535 | | 39.73 | 0.0543 | | 6.754 | 0.0007 | Y |
| DP0005 | 1.9 | | | 36.64 | | | 4.613 | | |
| DP0047.23 | 1.5 | 0.0532 | | 36.31 | 0.2336 | | 4.643 | 0.5403 | |
| DP0005 | 1.0 | | | 37.85 | | | 4.316 | | |
| DP0047.25 | 2.4 | 0.4384 | | 34.65 | 0.1783 | | 4.310 | 0.7660 | |
| DP0005 | 2.0 | | | 36.28 | | | 4.108 | | |

TABLE 11

Low nitrogen assay of OsDN-LTP1 transgenic rice plants under greenhouse low nitrogen conditions ($2^{nd}$ experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.01 | 1.6 | 0.2301 | | 33.61 | 0.1104 | | 3.479 | 0.2199 | |
| DP0047.05 | 1.6 | 0.2301 | | 35.14 | 0.0049 | Y | 3.489 | 0.2090 | |
| DP0047.06 | 1.6 | 0.2486 | | 32.72 | 0.3740 | | 3.477 | 0.2222 | |
| DP0047.12 | 1.6 | 0.1880 | | 35.12 | 0.0051 | Y | 3.502 | 0.1953 | |
| DP0047.15 | 1.6 | 0.1880 | | 33.29 | 0.1804 | | 3.479 | 0.2202 | |
| DP0047.16 | 1.6 | 0.2125 | | 34.11 | 0.0464 | Y | 3.479 | 0.2196 | |
| DP0047.17 | 1.6 | 0.2682 | | 34.07 | 0.0494 | Y | 3.479 | 0.2199 | |
| DP0047.19 | 1.6 | 0.1880 | | 34.26 | 0.0342 | Y | 3.495 | 0.2023 | |
| DP0047.23 | 1.6 | 0.2041 | | 34.88 | 0.0091 | Y | 3.485 | 0.2128 | |
| DP0047.25 | 1.6 | 0.2486 | | 35.09 | 0.0055 | Y | 3.475 | 0.2243 | |
| ZH11-TC | 1.3 | | | 31.60 | | | 3.078 | | |
| DP0047 (construct) | 1.6 | 0.2068 | | 34.23 | 0.0169 | Y | 3.484 | 0.2099 | |

TABLE 12

Low nitrogen assay of OsDN-LTP1 transgenic rice plants under greenhouse low nitrogen conditions ($2^{nd}$ experiment, DP0158 as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.01 | 1.6 | 0.2301 | | 33.61 | 0.3334 | | 3.479 | 0.1790 | |
| DP0047.05 | 1.6 | 0.2301 | | 35.14 | 0.0289 | Y | 3.489 | 0.1697 | |
| DP0047.06 | 1.6 | 0.2486 | | 32.72 | 0.7951 | | 3.477 | 0.1810 | |
| DP0047.12 | 1.6 | 0.1880 | | 35.12 | 0.0300 | Y | 3.502 | 0.1580 | |
| DP0047.15 | 1.6 | 0.1880 | | 33.29 | 0.4775 | | 3.479 | 0.1793 | |
| DP0047.16 | 1.6 | 0.2125 | | 34.11 | 0.1732 | | 3.479 | 0.1788 | |
| DP0047.17 | 1.6 | 0.2682 | | 34.07 | 0.1816 | | 3.479 | 0.1790 | |
| DP0047.19 | 1.6 | 0.1880 | | 34.26 | 0.1366 | | 3.495 | 0.1639 | |
| DP0047.23 | 1.6 | 0.2041 | | 34.88 | 0.0477 | Y | 3.485 | 0.1729 | |
| DP0047.25 | 1.6 | 0.2486 | | 35.09 | 0.0317 | Y | 3.475 | 0.1828 | |
| DP0158 | 1.3 | | | 32.39 | | | 3.039 | | |
| DP0047 (construct) | 1.6 | 0.2068 | | 34.23 | 0.0949 | | 3.484 | 0.1701 | |

In the third experiment, the same ten lines were tested, and the experiment design and the treatment were same to that in the second experiment. After low nitrogen stressed for 35 days, tiller number, SPAD value and fresh weight were measured. The average tiller number, SPAD value and fresh weight of the OsDN-LTP1 transgenic rice were more than that of ZH11-TC and DP0158 controls at construct level. The SPAD value of OsDN-LTP1 transgenic rice was significantly greater than both ZH11-TC and DP0158 controls; and the tiller number and fresh weight were significantly greater than DP0158 seedlings. As shown in Table 13 and 14, all the transgenic lines showed greater tiller number, SPAD value and fresh weights than either ZH11-TC or DP0158 controls. These results demonstrate OsDN-LTP1 transgenic rice obtained enhanced low nitrogen tolerance or improved NUE, and OsDN-LTP1 plays a role in enhancing NUE of transgenic plants.

TABLE 13

Low nitrogen assay of OsDN-LTP1 transgenic rice plants under greenhouse low nitrogen conditions ($3^{rd}$ experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.01 | 1.8 | 0.5251 | | 33.66 | 0.0926 | | 3.415 | 0.9186 | |
| DP0047.05 | 1.8 | 0.4647 | | 34.07 | 0.0472 | Y | 3.662 | 0.5429 | |
| DP0047.06 | 1.8 | 0.4647 | | 33.77 | 0.0779 | | 3.682 | 0.5062 | |
| DP0047.12 | 2.0 | 0.2270 | | 33.58 | 0.1050 | | 3.618 | 0.6305 | |

TABLE 13-continued

Low nitrogen assay of OsDN-LTP1 transgenic rice plants under greenhouse low nitrogen conditions (3rd experiment, ZH11-TC as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.15 | 2.1 | 0.0749 | | 33.83 | 0.0698 | | 3.733 | 0.4164 | |
| DP0047.16 | 2.1 | 0.1349 | | 34.09 | 0.0454 | Y | 3.537 | 0.8037 | |
| DP0047.17 | 1.9 | 0.3090 | | 33.80 | 0.0733 | | 3.860 | 0.2381 | |
| DP0047.19 | 2.1 | 0.1349 | | 34.18 | 0.0385 | Y | 4.027 | 0.0967 | |
| DP0047.23 | 1.9 | 0.2657 | | 33.88 | 0.0653 | | 3.551 | 0.7735 | |
| DP0047.25 | 2.0 | 0.2270 | | 34.01 | 0.0521 | | 3.723 | 0.4328 | |
| ZH11-TC | 1.6 | | | 31.39 | | | 3.451 | | |
| DP0047 (construct) | 1.9 | 0.2052 | | 33.89 | 0.0517 | | 3.681 | 0.4545 | |

TABLE 14

Low nitrogen assay of OsDN-LTP1 transgenic rice plants under greenhouse low nitrogen conditions (2nd experiment, DP0158 as control)

| | Tiller number | | | SPAD value | | | Fresh weight | | |
|---|---|---|---|---|---|---|---|---|---|
| Line ID | Average tiller number | P value | P ≤ 0.05 | Average SPAD value | P value | P ≤ 0.05 | Average fresh weight | P value | P ≤ 0.05 |
| DP0047.01 | 1.8 | 0.0897 | | 33.66 | 0.0290 | Y | 3.415 | 0.0287 | Y |
| DP0047.05 | 1.8 | 0.0730 | | 34.07 | 0.0129 | Y | 3.662 | 0.0038 | Y |
| DP0047.06 | 1.8 | 0.0730 | | 33.77 | 0.0236 | Y | 3.682 | 0.0031 | Y |
| DP0047.12 | 2.0 | 0.0232 | Y | 33.58 | 0.0338 | Y | 3.618 | 0.0056 | Y |
| DP0047.15 | 2.1 | 0.0045 | Y | 33.83 | 0.0207 | Y | 3.733 | 0.0019 | Y |
| DP0047.16 | 2.1 | 0.0106 | Y | 34.09 | 0.0123 | Y | 3.537 | 0.0111 | Y |
| DP0047.17 | 1.9 | 0.0376 | Y | 33.80 | 0.0219 | Y | 3.860 | 0.0005 | Y |
| DP0047.19 | 2.1 | 0.0106 | Y | 34.18 | 0.0102 | Y | 4.027 | 0.0001 | Y |
| DP0047.23 | 1.9 | 0.0297 | Y | 33.88 | 0.0191 | Y | 3.551 | 0.0099 | Y |
| DP0047.25 | 2.0 | 0.0232 | Y | 34.01 | 0.0146 | Y | 3.723 | 0.0021 | Y |
| DP0158 | 1.3 | | | 30.72 | | | 2.656 | | |
| DP0047 (construct) | 1.9 | 0.0145 | Y | 33.89 | 0.0134 | Y | 3.681 | 0.0009 | Y |

Example 5

Laboratory Chlorate Screening of Transgenic Rice Plants

Nitrate is a major source of inorganic nitrogen utilized by higher plants. Chlorate is a nitrate analog which can be uptake, transported by the same system with nitrogen and reduced to a toxic compound (chlorite) by nitrate reductase (NR) in plants. To further confirm the nitrogen use efficiency, chlorate solution is selected to treat seedlings, and seedlings which are sensitive to chlorate will be considered to have better nitrogen use efficiency or low nitrogen tolerance.

Laboratory Chlorate Screening Method:

In this assay, over-expression transgenic rice plants from ten transgenic lines were selected and screened by chlorate solution. ZH11-TC and empty vector (DP0158) transgenic plants were used as controls.

$T_2$ transgenic seeds were sterilized and germinated as description in Example 4, and this assay was performed in culture room kept temperature at 28-30° C. and humidity around ~30%. The germinated seeds were placed in a tube with a hole at the bottom, and water cultured at 30° C. for 6 days till one-leaf and one-terminal bud stage. Uniform seedlings about 5.5 cm in height were selected for chlorate screening. Randomized block design was used in this experiment. There are five blocks in one screened container. Each transgenic line was placed in one row (12 plants/line), and ZH11-TC and DP0158 seedlings were placed in 3 rows (3*12 plants) randomly in one block. Then the seedlings were treated with 0.4 mM chlorate in concentration for 3-5 days at 10 h day/14 h night, the treated seedlings first encountered night and uptake the chlorate solution which was changed in the third day. After treated for 5 days, the seedlings were then cultured in 1/10 Hoagland's solution (Table 6) for 4 days. The seedlings with withered leaves and totally without green are counted as sensitive; while the seedlings only with necrosed leaves or stem, or bleached leaves are not considered to be sensitive seedlings.

Sensitive rate was used as a parameter to for this screen, which is the percentage of the number of sensitive plants over the total plant number.

The data was analyzed at construct level (all transgenic plants compared to the control) and transgenic line level (different transgenic lines compared to the control) using a statistic model of "Y~seg+line (seg)+rep+error", with random effect: "rep"; Statistic Method: "SAS Proc Glimmix".

Chlorate Screening Results:

1) Validation Results for OsDN-PPR1 (DP0039) Transgenic Rice

In the first experiment, for OsDN-PPR1 transgenic rice, after treated with 0.4 mM chlorate solution for 2 days and cultured in 1/10 Hoagland solution for 4 days, 227 of the 600 transgenic seedlings (38%) died, while only 14 of the 180 (8%) DP0158 seedlings died, and 32 of the 180 (18%) ZH11-TC seedlings died. The sensitive rate of OsDN-PPR1 transgenic seedlings was significantly (P value=0.0000) higher than that of either DP0158 or ZH11-TC controls. These results indicate that the OsDN-PPR1 transgenic seedlings had enhanced chlorate sensitive rate compared to both DP0158 and ZH11-TC seedlings at construct level. Table 15 shows the analysis at transgenic line level. Eight lines exhibited higher sensitive rates than both of ZH11-TC and DP0158. Five lines exhibited significantly higher sensitive rates than ZH11-TC control, and eight lines exhibited significantly higher sensitive rates than DP0158 seedlings.

TABLE 15

Chlorate sensitive assay of OsDN-PPR1 transgenic rice seedlings at transgenic line level (1st experiment)

| Line ID | Number of dead seedlings | Number of total seedlings | Sensitive rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0039.04 | 9 | 60 | 15 | 0.6196 | | 0.1089 | |
| DP0039.07 | 16 | 60 | 27 | 0.1401 | | 0.0005 | Y |
| DP0039.13 | 5 | 60 | 8 | 0.0895 | | 0.8903 | |
| DP0039.14 | 15 | 60 | 25 | 0.2249 | | 0.0012 | Y |
| DP0039.15 | 20 | 60 | 33 | 0.0144 | Y | 0.0000 | Y |
| DP0039.18 | 39 | 60 | 65 | 0.0000 | Y | 0.0000 | Y |
| DP0039.19 | 33 | 60 | 55 | 0.0000 | Y | 0.0000 | Y |
| DP0039.20 | 36 | 60 | 60 | 0.0000 | Y | 0.0000 | Y |
| DP0039.22 | 37 | 60 | 62 | 0.0000 | Y | 0.0000 | Y |
| DP0039.25 | 17 | 60 | 28 | 0.0837 | | 0.0002 | Y |
| ZH11-TC | 32 | 180 | 18 | | | | |
| DP0158 | 14 | 180 | 8 | | | | |

In the second experiment, the same nine transgenic lines were tested. 356 of the 600 (59%) OsDN-PPR1 transgenic rice died after chlorate treatment, while 91 of 180 (51%) DP0158 seedlings died and 65 of 180 (36%) ZH11-TC seedlings died. The sensitive rate of OsDN-PPR1 transgenic seedlings was significantly higher than that of both DP0158 and ZH11-TC controls. Further analysis at transgenic line level indicated four same transgenic lines (DP0039.07, DP0039.18, DP0039.19 and DP0039.22) showed higher sensitive rates than DP0158 seedlings (Table 16) and four transgenic lines (DP0039.18, DP0039.19, DP0039.22 and DP0039.25) showed higher sensitive rates than ZH11-TC seedling in two experiments. These results clearly and consistently demonstrate that OsDN-PPR1 transgenic rice plants exhibited enhanced chlorate sensitive compared to DP0158 and ZH11-TC seedlings at construct and transgenic line level at seedling stages. Over-expression of OsDN-PPR1 under CaMV 35S promoter increased the chlorate sensitivity of transgenic plants.

TABLE 16

Chlorate sensitive assay of OsDN-PPR1 transgenic rice seedlings at transgenic line level (2nd experiment)

| Line ID | Number of dead seedlings | Number of total seedlings | Sensitive rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0039.01 | 42 | 60 | 70 | 0.0000 | Y | 0.0115 | Y |
| DP0039.04 | 28 | 60 | 47 | 0.1501 | | 0.6017 | |
| DP0039.07 | 39 | 60 | 65 | 0.0003 | Y | 0.0567 | |
| DP0039.13 | 39 | 60 | 65 | 0.0003 | Y | 0.0567 | |
| DP0039.14 | 22 | 60 | 37 | 0.9377 | | 0.0667 | |
| DP0039.18 | 43 | 60 | 72 | 0.0000 | Y | 0.0064 | Y |
| DP0039.19 | 45 | 60 | 75 | 0.0000 | Y | 0.0019 | Y |
| DP0039.20 | 28 | 60 | 47 | 0.1501 | | 0.6017 | |
| DP0039.22 | 39 | 60 | 65 | 0.0003 | Y | 0.0567 | |
| DP0039.25 | 31 | 60 | 52 | 0.0368 | Y | 0.8768 | |
| ZH11-TC | 65 | 180 | 36 | | | | |
| DP0158 | 91 | 180 | 51 | | | | |

2) Validation Results of OsDN-LNP1(DP0047) Transgenic Rice

For OsDN-LNP1 transgenic rice, in the first experiment, 266 of the 576 transgenic seedlings (46%) died, whereas 67 of the 192 (35%) ZH11-TC seedlings died, and the sensitive rate of OsDN-LNP1 transgenic seedlings was significantly (P value=0.0112) higher than that of the ZH11-TC control. The result indicates that the OsDN-LNP1 transgenic seedlings had enhanced chlorate sensitive rate compared to ZH11-TC seedlings at construct level.

Further analysis at transgenic line level indicate that seven of the ten transgenic lines had higher sensitive rates than ZH11-TC seedlings, and the sensitive rates of four transgenic lines were significantly higher than ZH11-TC seedlings. These results demonstrate that OsDN-LNP1 transgenic rice plants have enhanced chlorate sensitive rates compared to ZH11-TC seedlings at construct and transgenic line level at seedling stages. OsDN-LNP1 increased the chlorate sensitivity of transgenic plants.

TABLE 17

Chlorate sensitive assay of OsDN-LNP1 transgenic rice seedlings at transgenic line level (1st experiment)

| Line ID | Number of dead seedlings | Number of total seedlings | Sensitive rate (%) | P value | P ≤ 0.05 |
|---|---|---|---|---|---|
| DP0047.01 | 27 | 60 | 45 | 0.1641 | |
| DP0047.03 | 27 | 60 | 45 | 0.1641 | |
| DP0047.05 | 32 | 60 | 53 | 0.0141 | Y |
| DP0047.06 | 31 | 60 | 52 | 0.0244 | Y |
| DP0047.10 | 42 | 60 | 70 | 0.0000 | Y |
| DP0047.15 | 21 | 60 | 35 | 0.9881 | |
| DP0047.16 | 19 | 60 | 32 | 0.6471 | |
| DP0047.17 | 35 | 60 | 58 | 0.0023 | Y |
| DP0047.19 | 15 | 36 | 42 | 0.4415 | |
| DP0047.25 | 17 | 60 | 28 | 0.3514 | |
| ZH11-TC | 67 | 192 | 35 | | |

In the second experiment, 273 of the 600 transgenic seedlings (46%) died, whereas 59 of the 180 (33%) ZH11-TC seedlings died. The sensitive rate of OsDN-LNP1 transgenic seedlings was significantly (P value=0.0052) higher than ZH11-TC control. Analysis at transgenic line level indicates that eight of the ten transgenic lines had higher sensitive rates than ZH11-TC seedlings, and the sensitive rates of four transgenic lines were significantly higher than ZH11-TC seedlings (Table 18). These results further demonstrate that OsDN-LNP1 transgenic rice plants have enhanced chlorate sensitive rates compared to ZH11-TC seedlings at construct and transgenic line level at seedling stages. OsDN-LNP1 increased the chlorate sensitivity of transgenic plants.

As elucidated in example 4, over-expression of OsDN-LNP1 gene improved nitrogen use efficiency of the transgenic rice. These cross-validations further confirm the increase low nitrogen tolerance or NUE of OsDN-LNP1 transgenic rice.

TABLE 18

Chlorate sensitive assay of OsDN-LNP1 transgenic rice seedlings at transgenic line level (2nd experiment)

| Line ID | Number of dead seedlings | Number of total seedlings | Sensitive rate (%) | P value | P ≤ 0.05 |
|---|---|---|---|---|---|
| DP0047.01 | 15 | 60 | 25 | 0.2635 | |
| DP0047.03 | 32 | 60 | 53 | 0.0065 | Y |
| DP0047.05 | 21 | 60 | 35 | 0.7526 | |
| DP0047.15 | 15 | 60 | 25 | 0.2635 | |
| DP0047.16 | 28 | 60 | 47 | 0.0580 | |
| DP0047.17 | 42 | 60 | 70 | 0.0000 | Y |
| DP0047.19 | 26 | 60 | 43 | 0.1443 | |
| DP0047.20 | 34 | 60 | 57 | 0.0019 | Y |
| DP0047.22 | 28 | 60 | 47 | 0.0580 | |
| DP0047.25 | 32 | 60 | 53 | 0.0066 | Y |
| ZH11-TC | 59 | 180 | 33 | | |

3) Validation Results of OsRRM1(DP0049) Transgenic Rice

In the first experiment, after chlorate treatment, 259 of the 600 (43%) OsRRM1 transgenic seedlings died, while 39 of the 180 (22%) DP0158 seedlings died and 57 of the 180 (32%) ZH11-TC seedlings died. The sensitive rate of OsRRM1 transgenic seedlings was significantly higher than that of DP0158 (P value=0.0000) and ZH11-TC (P value=0.0192) controls, indicating the OsRRM1 transgenic seedlings had increased chlorate sensitivity. Further analysis at transgenic line level demonstrates that seven of the ten transgenic lines had higher sensitive rates than DP0158 seedlings and ZH11-TC controls. These results demonstrate that OsRRM1 transgenic rice plants had enhanced chlorate sensitivity compared to both ZH11-TC and DP0158 seedlings at construct and transgenic line level at seedling stages. Over-expression of OsRRM1 under CaMV 35S increased the chlorate sensitivity of transgenic plants.

TABLE 19

Chlorate sensitive assay of OsRRM1 rice seedlings at transgenic line level (1st experiment)

| Line ID | Number of dead seedlings | Number of total seedlings | Sensitive rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0049.12 | 25 | 60 | 42 | 0.1633 | | 0.0040 | Y |
| DP0049.13 | 10 | 60 | 17 | 0.0311 | | 0.4091 | |
| DP0049.16 | 26 | 60 | 43 | 0.1061 | | 0.0021 | Y |
| DP0049.17 | 28 | 60 | 47 | 0.0405 | Y | 0.0005 | Y |
| DP0049.19 | 28 | 60 | 47 | 0.0405 | Y | 0.0005 | Y |
| DP0049.20 | 37 | 60 | 62 | 0.0002 | Y | 0.0000 | Y |
| DP0049.26 | 37 | 60 | 62 | 0.0002 | Y | 0.0000 | Y |
| DP0049.27 | 39 | 60 | 65 | 0.0000 | Y | 0.0000 | Y |
| DP0049.28 | 10 | 60 | 17 | 0.0311 | | 0.4091 | |
| DP0049.32 | 19 | 60 | 32 | 0.9969 | | 0.1229 | |

TABLE 19-continued

Chlorate sensitive assay of OsRRM1 rice seedlings at transgenic line level (1st experiment)

| Line ID | Number of dead seedlings | Number of total seedlings | Sensitive rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0158 | 39 | 180 | 22 | | | | |
| DP0158 | 39 | 180 | 22 | | | | |

In the second experiment, after chlorate treatment, 476 of the 600 (79%) OsRRM1 transgenic seedlings died, while 83 of the 180 (46%) DP0158 seedlings died and 83 of the 180 (46%) ZH11-TC seedlings died. The sensitive rate of OsRRM1 transgenic seedlings was significantly higher than DP0158 (P value=0.0000) and ZH11-TC (P value=0.0000) controls. These results indicate that the OsRRM1 transgenic seedlings had increased chlorate sensitivity. Analysis at transgenic line level demonstrates that all the ten transgenic lines exhibited higher sensitive rates than both DP0158 and ZH11-TC controls (Table 20). In the two experiments, many lines showed better chlorate sensitivity. These results demonstrate that OsRRM1 transgenic rice plants had enhanced chlorate sensitivity compared to both ZH11-TC and DP0158 seedlings at construct and transgenic line level at seedling stages. Over-expression of OsRRM1 under CaMV 35S increased the chlorate sensitivity of transgenic plants.

TABLE 20

Chlorate sensitive assay of OsRRM1 rice seedlings at transgenic line level (2nd experiment)

| Line ID | Number of dead seedlings | Number of of total seedlings | Sensitive rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0049.12 | 52 | 60 | 87 | 0.0000 | Y | 0.0000 | Y |
| DP0049.13 | 34 | 60 | 57 | 0.1628 | | 0.1628 | |
| DP0049.16 | 48 | 60 | 80 | 0.0000 | Y | 0.0000 | Y |
| DP0049.17 | 45 | 60 | 75 | 0.0004 | Y | 0.0004 | Y |
| DP0049.19 | 41 | 60 | 68 | 0.0046 | Y | 0.0046 | Y |
| DP0049.20 | 53 | 60 | 88 | 0.0000 | Y | 0.0000 | Y |
| DP0049.26 | 58 | 60 | 97 | 0.0000 | Y | 0.0000 | Y |
| DP0049.27 | 52 | 60 | 87 | 0.0000 | Y | 0.0000 | Y |
| DP0049.28 | 46 | 60 | 77 | 0.0002 | Y | 0.0002 | Y |
| DP0049.32 | 47 | 60 | 78 | 0.0000 | Y | 0.0000 | Y |
| ZH11-TC | 83 | 180 | 46 | | | | |
| DP0158 | 83 | 180 | 46 | | | | |

Example 6

Field Low Nitrogen Screens of Mature Plants

Field low nitrogen screens were carried out in Beijing. Two nitrogen levels: N-0 (using fertilizer without nitrogen) and N-1 (with normal fertilizer at 180 kg Nitrogen/ha) were set in this experiment. Seed germination and seedling culturing were performed as described in Example 4. The germinated seeds were planted in a seedbed field. At 3-leaf stage, the seedlings were transplanted into two testing fields, with 4 replicates and 10 plants per replicate for each transgenic line, (the 4 replicates planted in the same block). The ZH11-TC and DP0158 plants were nearby the transgenic lines in the same block, and were used as controls in the statistical analysis.

The rice plants were managed by normal practice using pesticides, but applying phosphorous fertilizer and potassium fertilizer for N-0 treatment and normal fertilizers for N-1.

The SPAD value of the fully expanded flag leaf and top second leaf were measured by SPAD-502 chlorophyll meter at about 10 day after heading. The SPAD value of each transgenic rice plant is the arithmetic mean of SPAD values from three rice plants in the middle of one rice row.

The plant height which is the length from the rice stem base to the end of panicle or the end of the highest leaf was measured at 20 day after heading. Six rice plants in the middle of one rice row were measured and the arithmetic mean of these three values is the plant height of the transgenic rice plant.

At the end of the season, six representative plants of each transgenic line were harvested from the middle of the row per line. The panicles which have five seeds are considered as effective panicles, and the effective panicle number is the total of the effective panicle per plant. The biomass per plant is the dry weight of the rice plant without root and panicle. The SPAD value, plant height, effective number, biomass and grain weight data was statistically analyzed using mixed linear model by ASRemI program. Positive transgenic lines are selected based on the analysis (P≤0.1).

1) Field NUE Validation Results of OsLRP1 (DP0039) Transgenic Rice

As shown in Table 21, the grain yield of OsLRP1 transgenic rice was 31.47 g per plant, was lower than that of ZH11-TC and higher than DP0158 control under low nitrogen condition at construct level. The similar results were obtained for the OsLRP1 transgenic rice under normal nitrogen condition (Table 22). There was no difference between OsLRP1 transgenic rice and the controls in grain yield, biomass and effective panicle number; however OsLRP1 transgenic rice exhibited higher plant height than both ZH11-TC and DP0158 controls at low nitrogen conditions.

Table 24 demonstrates that two lines were significantly taller than ZH11-TC control and six transgenic lines were significantly taller than DP0158 control under low nitrogen condition. Table 25 demonstrates that one transgenic line was significantly taller than ZH11-TC and four plants were significantly taller than DP0158 control under normal nitrogen conditions. At the construct level, OsLRP1 transgenic rice plants were taller than both ZH11-TC and DP0158 controls under low nitrogen condition, and were shorter than both ZH11-TC and DP0158 controls under normal condition. These results demonstrate that OsLRP1 transgenic rice plants exhibited enhanced low nitrogen tolerance and/or NUE under low nitrogen field conditions as reflected by plant height. OsLRP1 gene can be used to improve low nitrogen tolerance and/or NUE.

TABLE 21

Grain yield analysis of OsLRP1 transgenic rice under field low nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0039.04 | 39 | 24 | 33.12 | 0.809 | | 0.169 | |
| DP0039.07 | 40 | 24 | 30.57 | 0.357 | | 0.828 | |
| DP0039.13 | 39 | 24 | 32.39 | 0.928 | | 0.292 | |
| DP0039.14 | 40 | 24 | 29.87 | 0.214 | | 0.920 | |
| DP0039.18 | 40 | 24 | 34.31 | 0.433 | | 0.055 | Y |
| DP0039.19 | 40 | 24 | 31.12 | 0.505 | | 0.640 | |
| DP0039.20 | 40 | 24 | 30.93 | 0.448 | | 0.703 | |
| DP0039.22 | 40 | 24 | 29.79 | 0.201 | | 0.891 | |
| DP0039.25 | 40 | 24 | 31.11 | 0.500 | | 0.645 | |
| ZH11-TC | 39 | 23 | 32.59 | | | | |
| DP0158 | 39 | 22 | 30.09 | | | | |
| DP0039 (construct) | | | 31.47 | 0.510 | | 0.420 | |

TABLE 22

Grain yield analysis of OsLRP1 transgenic rice under field normal nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0039.04 | 40 | 24 | 45.08 | 0.773 | | 0.232 | |
| DP0039.07 | 39 | 24 | 42.63 | 0.237 | | 0.764 | |
| DP0039.13 | 38 | 20 | 46.10 | 0.932 | | 0.119 | |
| DP0039.14 | 40 | 20 | 43.48 | 0.382 | | 0.542 | |
| DP0039.18 | 40 | 24 | 45.42 | 0.870 | | 0.187 | |
| DP0039.19 | 40 | 24 | 46.92 | 0.703 | | 0.062 | Y |
| DP0039.20 | 40 | 24 | 42.31 | 0.193 | | 0.853 | |
| DP0039.22 | 29 | 18 | 44.92 | 0.746 | | 0.285 | |
| DP0039.25 | 39 | 24 | 41.81 | 0.139 | | 1.000 | |
| ZH11-TC | 40 | 24 | 45.87 | | | | |
| DP0158 | 40 | 23 | 41.80 | | | | |
| DP0039 (construct) | | | 44.30 | 0.411 | | 0.193 | |

TABLE 23

Biomass analysis of OsLRP1 transgenic rice under low nitrogen condition

| Line ID | Number of survival plants | Number of harvested plants | Biomass (g) | CK = ZH11-TC P value | CK = ZH11-TC P ≤ 0.1 | K = DP0158 P value | K = DP0158 P ≤ 0.1 |
|---|---|---|---|---|---|---|---|
| DP0039.04 | 39 | 24 | 25.45 | 0.176 | | 0.258 | |
| DP0039.07 | 40 | 24 | 24.09 | 0.566 | | 0.729 | |
| DP0039.13 | 39 | 24 | 24.51 | 0.413 | | 0.554 | |
| DP0039.14 | 40 | 24 | 24.30 | 0.487 | | 0.639 | |
| DP0039.18 | 40 | 24 | 25.13 | 0.243 | | 0.344 | |
| DP0039.19 | 40 | 24 | 24.37 | 0.463 | | 0.609 | |
| DP0039.20 | 40 | 24 | 24.08 | 0.569 | | 0.732 | |

TABLE 23-continued

| Biomass analysis of OsLRP1 transgenic rice under low nitrogen condition | | | | | | | |
|---|---|---|---|---|---|---|---|
| | Number of | Number of | | CK = ZH11-TC | | K = DP0158 | |
| Line ID | survival plants | harvested plants | Biomass (g) | P value | P ≤ 0.1 | P value | P ≤ 0.1 |
| DP0039.22 | 40 | 24 | 25.88 | 0.109 | | 0.167 | |
| DP0039.25 | 40 | 24 | 25.63 | 0.147 | | 0.220 | |
| ZH11-TC | 39 | 23 | 23.08 | | | | |
| DP0158 | 39 | 22 | 23.48 | | | | |
| DP0039 (construct) | | | 24.82 | 0.212 | | 0.332 | |

TABLE 24

| Plant height analysis of OsLRP1 transgenic rice under low nitrogen condition | | | | | | | |
|---|---|---|---|---|---|---|---|
| | Number of | Number of | | CK = ZH11-TC | | CK = DP0158 | |
| Line ID | survival plants | measured plants | Plant height | P value | P ≤ 0.1 | P value | P ≤ 0.1 |
| DP0039.04 | 39 | 24 | 116.73 | 0.008 | Y | 0.000 | Y |
| DP0039.07 | 40 | 24 | 113.26 | 0.874 | | 0.035 | Y |
| DP0039.13 | 39 | 24 | 112.84 | 0.883 | | 0.083 | Y |
| DP0039.14 | 40 | 24 | 112.54 | 0.717 | | 0.129 | |
| DP0039.18 | 40 | 24 | 114.36 | 0.336 | | 0.004 | Y |
| DP0039.19 | 40 | 24 | 117.44 | 0.001 | Y | 0.000 | Y |
| DP0039.20 | 40 | 24 | 108.44 | 0.001 | | 0.147 | |
| DP0039.22 | 40 | 24 | 112.12 | 0.497 | | 0.213 | |
| DP0039.25 | 40 | 24 | 113.65 | 0.654 | | 0.016 | Y |
| ZH11-TC | 39 | 24 | 113.05 | | | | |
| DP0158 (construct) | 39 | 24 | 110.43 | | | | |
| DP0039 | | | 113.49 | 0.773 | | 0.046 | Y |

TABLE 25

| Plant height analysis of OsLRP1 transgenic rice under normal nitrogen condition | | | | | | | |
|---|---|---|---|---|---|---|---|
| | Number of | Number of | | CK = ZH11-TC | | CK = DP0158 | |
| Line ID | survival plants | measured plants | Plant height | P value | P ≤ 0.1 | P value | P ≤ 0.1 |
| DP0039.04 | 40 | 24 | 129.14 | 0.643 | | 0.017 | Y |
| DP0039.07 | 39 | 24 | 128.43 | 0.898 | | 0.064 | Y |
| DP0039.13 | 38 | 24 | 125.52 | 0.006 | | 0.503 | |
| DP0039.14 | 40 | 24 | 118.25 | 0.000 | | 0.000 | |
| DP0039.18 | 40 | 24 | 128.36 | 0.845 | | 0.066 | Y |
| DP0039.19 | 40 | 24 | 131.91 | 0.005 | Y | 0.000 | Y |
| DP0039.20 | 40 | 24 | 120.72 | 0.000 | | 0.000 | |
| DP0039.22 | 29 | 24 | 125.36 | 0.016 | | 0.501 | |
| DP0039.25 | 39 | 24 | 126.08 | 0.032 | | 0.874 | |
| ZH11-TC | 40 | 24 | 128.58 | | | | |
| DP0158 | 40 | 24 | 126.27 | | | | |
| DP0039 (construct) | | | 125.98 | 0.068 | | 0.840 | |

2) Field NUE Validation Results of OsRRM1 (DP0049) Transgenic Rice

The grain yield, biomass, effective panicle number and plant height of OsRRM1 transgenic rice plants were measured. Table 25 shows that the grain yield of the OsRRM1 transgenic rice was lower than that of ZH11-TC and DP0158 controls at construct level under low nitrogen conditions, there was no significant difference between the transgenic rice and controls. Table 26 shows the grain yield results under field normal nitrogen conditions. The grain yield of OsRRM1 transgenic rice was higher than that of ZH11-TC and DP0158 controls at construct level, eight lines exhibited higher grain yields than ZH11-TC control, and all the twelve lines exhibited higher grain yields than DP0158 control. There were no significant difference between the OsRRM1 transgenic rice and the controls for the parameters of biomass, effective panicle number and plant height. These results demonstrate that OsRRM1 transgenic rice plants obtained higher grain yield under normal nitrogen conditions, and little decreased grain yield under low nitrogen conditions.

The SPAD values of the plants under low nitrogen conditions were measured. As shown in Table 28, the flag leaf SPAD value of OsRRM1 transgenic rice plants was 40.58, and was significantly higher than that of ZH11-TC and DP0158 plants at construct level. At transgenic line level, ten lines exhibited significantly higher flag leaf SPAD values than ZH11-TC control, and eight lines exhibited significantly higher flag leaf SPAD values than that of DP0158 control. As shown in Table 29, the top second leaf SPAD value of OsRRM1 transgenic rice plants was 39.57, and was significantly higher than that of ZH11-TC and DP0158 plants at construct level. At transgenic line level, eleven lines exhibited significantly higher top second leaf SPAD values than ZH11-TC control, and ten lines exhibited significantly higher top second leaf SPAD values than that of DP0158 control. These results demonstrate that OsRRM1 transgenic rice plants showed better growth status than the controls under field low nitrogen conditions, OsRRM1 may plays a role in improving low nitrogen tolerance and/or NUE.

TABLE 26

Grain yield analysis of OsRRM1 transgenic rice under field low nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0049.10 | 39 | 19 | 31.43 | 0.594 | | 0.535 | |
| DP0049.12 | 40 | 24 | 30.03 | 0.238 | | 0.979 | |
| DP0049.13 | 39 | 24 | 30.18 | 0.266 | | 0.967 | |
| DP0049.16 | 38 | 20 | 28.54 | 0.063 | | 0.477 | |
| DP0049.17 | 40 | 24 | 29.71 | 0.185 | | 0.860 | |
| DP0049.19 | 37 | 24 | 29.61 | 0.170 | | 0.826 | |
| DP0049.20 | 36 | 19 | 28.71 | 0.073 | | 0.524 | |
| DP0049.22 | 39 | 21 | 24.69 | 0.000 | | 0.013 | |
| DP0049.26 | 39 | 24 | 31.45 | 0.599 | | 0.531 | |
| DP0049.27 | 39 | 24 | 31.26 | 0.541 | | 0.591 | |
| DP0049.28 | 40 | 24 | 29.11 | 0.109 | | 0.650 | |
| DP0049.32 | 40 | 24 | 33.01 | 0.846 | | 0.177 | |
| ZH11-TC | 40 | 24 | 32.59 | | | | |
| DP0158 | 40 | 24 | 30.09 | | | | |
| DP0049 (construct) | | | 29.81 | 0.083 | | 0.862 | |

TABLE 27

Grain yield analysis of OsRRM1 transgenic rice under field normal nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0049.10 | 33 | 9 | 50.48 | 0.140 | | 0.006 | Y |
| DP0049.12 | 40 | 24 | 44.90 | 0.723 | | 0.253 | |
| DP0049.13 | 38 | 20 | 48.93 | 0.260 | | 0.009 | Y |
| DP0049.16 | 38 | 22 | 44.73 | 0.675 | | 0.279 | |
| DP0049.17 | 38 | 22 | 46.26 | 0.886 | | 0.100 | |
| DP0049.19 | 36 | 20 | 46.73 | 0.751 | | 0.070 | Y |
| DP0049.20 | 38 | 22 | 47.98 | 0.436 | | 0.022 | Y |
| DP0049.22 | 31 | 17 | 42.49 | 0.280 | | 0.825 | |
| DP0049.26 | 40 | 23 | 47.53 | 0.541 | | 0.035 | Y |
| DP0049.27 | 40 | 24 | 49.20 | 0.219 | | 0.006 | Y |
| DP0049.28 | 36 | 23 | 46.47 | 0.823 | | 0.084 | Y |
| DP0049.32 | 39 | 20 | 44.34 | 0.598 | | 0.382 | |
| ZH11-TC | 40 | 24 | 45.87 | | | | |
| DP0158 | 40 | 24 | 41.80 | | | | |
| DP0049 (construct) | | | 46.67 | 0.649 | | 0.006 | Y |

TABLE 28

Flag leaf SPAD value analysis of OsRRM1 transgenic rice under field low nitrogen condition

| Line ID | Number of survival plants | Number of measured plants | SPAD value | CK = ZH11-TC P value | CK = ZH11-TC P ≤ 0.1 | CK = DP0158 P value | CK = DP0158 P ≤ 0.1 |
|---|---|---|---|---|---|---|---|
| DP0049.10 | 39 | 12 | 40.51 | 0.028 | Y | 0.069 | Y |
| DP0049.12 | 40 | 12 | 39.95 | 0.160 | | 0.299 | |
| DP0049.13 | 39 | 12 | 40.87 | 0.007 | Y | 0.020 | Y |

TABLE 28-continued

Flag leaf SPAD value analysis of OsRRM1 transgenic rice under field low nitrogen condition

| Line ID | Number of survival plants | Number of measured plants | SPAD value | CK = ZH11-TC P value | CK = ZH11-TC P ≤ 0.1 | CK = DP0158 P value | CK = DP0158 P ≤ 0.1 |
|---|---|---|---|---|---|---|---|
| DP0049.16 | 38 | 12 | 41.14 | 0.002 | Y | 0.006 | Y |
| DP0049.17 | 40 | 12 | 40.26 | 0.062 | Y | 0.138 | |
| DP0049.19 | 37 | 12 | 40.26 | 0.062 | Y | 0.134 | |
| DP0049.20 | 36 | 12 | 40.65 | 0.017 | Y | 0.044 | Y |
| DP0049.22 | 39 | 12 | 39.54 | 0.394 | | 0.631 | |
| DP0049.26 | 39 | 12 | 40.97 | 0.004 | Y | 0.012 | Y |
| DP0049.27 | 39 | 12 | 41.35 | 0.001 | Y | 0.002 | Y |
| DP0049.28 | 40 | 12 | 40.47 | 0.031 | Y | 0.076 | Y |
| DP0049.32 | 40 | 12 | 40.97 | 0.005 | Y | 0.013 | Y |
| ZH11-TC | 40 | 12 | 38.95 | | | | |
| DP0158 | 40 | 12 | 39.21 | | | | |
| DP0049 (construct) | | | 40.58 | 0.002 | Y | 0.010 | Y |

TABLE 29

Top second leaf SPAD value analysis of OsRRM1 transgenic rice under field low nitrogen condition

| Line ID | Number of survival plants | Number of measured plants | SPAD value | CK = ZH11-TC P value | CK = ZH11-TC P ≤ 0.1 | CK = DP0158 P value | CK = DP0158 P ≤ 0.1 |
|---|---|---|---|---|---|---|---|
| DP0049.10 | 39 | 12 | 39.78 | 0.011 | Y | 0.022 | Y |
| DP0049.12 | 40 | 12 | 39.26 | 0.054 | Y | 0.093 | Y |
| DP0049.13 | 39 | 12 | 40.02 | 0.005 | Y | 0.011 | Y |
| DP0049.16 | 38 | 12 | 40.14 | 0.003 | Y | 0.006 | Y |
| DP0049.17 | 40 | 12 | 39.29 | 0.045 | Y | 0.082 | Y |
| DP0049.19 | 37 | 12 | 39.55 | 0.022 | Y | 0.040 | Y |
| DP0049.20 | 36 | 12 | 39.82 | 0.010 | Y | 0.020 | Y |
| DP0049.22 | 39 | 12 | 38.41 | 0.332 | | 0.470 | |
| DP0049.26 | 39 | 12 | 39.54 | 0.022 | Y | 0.041 | Y |
| DP0049.27 | 39 | 12 | 40.35 | 0.001 | Y | 0.003 | Y |
| DP0049.28 | 40 | 12 | 39.20 | 0.060 | Y | 0.104 | |
| DP0049.32 | 40 | 12 | 39.44 | 0.033 | Y | 0.058 | Y |
| ZH11-TC | 40 | 12 | 37.57 | | | | |
| DP0158 | 40 | 12 | 37.79 | | | | |
| DP0049 (construct) | | | 39.57 | 0.003 | Y | 0.008 | Y |

Example 7

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress and cold stress usually leads to increased reactive oxygen species (ROS) in plants and sometimes, the drought and/or cold tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant and cold tolerant transgenic rice plants was tested.

Paraquat Assay Methods:

Ten transgenic lines of each transgenic rice line were tested by paraquat assay. Tissue-cultured Zhonghua 11 plants (ZH11-TC) were used as controls. $T_2$ transgenic seeds were sterilized and germinated as described in Example 4, and this assay was carried out in growth room with temperature at 28-30° C. and humidity ~30%. The germinated seeds were placed in a tube with a hole at the bottom, and water cultured at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 μM paraquat solution for 7 days at 10 h day/14 h night, and the treated seedlings first encountered dark and took up the paraquat solution which was changed every two days.

After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS Proc Glimmix".

Paraquat Assay Results:

1) Paraquat Validation Results of OsDN-LNP1(DP0047) Transgenic Rice

In the first experiment, after paraquat solution treated, 259 of the 600 OsDN-LNP1 transgenic seedlings (43%) kept green and showed tolerant phenotype, while 34 of the 180 (19%) seedlings from ZH11-TC showed tolerant phenotype. The tolerance rate of all screened OsDN-LNP1 transgenic seedlings was significantly greater than ZH11-TC (P value=0.0000) control. These results indicate that the OsDN-LNP1 transgenic seedlings exhibited enhanced paraquat tolerance compared to ZH11-TC control at construct level.

Analysis at transgenic line level indicates that all transgenic lines exhibited greater tolerance rates compared with ZH11-TC control, and nine lines exhibited significantly greater tolerance rates (Table 30). These results demonstrate that OsDN-LNP1 transgenic rice plants had enhanced paraquat tolerance at construct and transgenic line level at seedling stages. OsDN-LNP1 functions in enhancing paraquat tolerance or antioxidative ability of transgenic plants.

TABLE 30

Paraquat tolerance assay of OsDN-LNP1 transgenic rice plants at transgenic line level (1st experiment)

| Line ID | Number of tolerant seedlings | Number of total seedlings | Tolerance rate (%) | P value | P ≤ 0.05 |
|---|---|---|---|---|---|
| DP0047.01 | 21 | 60 | 35 | 0.0138 | Y |
| DP0047.03 | 15 | 60 | 25 | 0.3145 | |
| DP0047.05 | 31 | 60 | 52 | 0.0000 | Y |
| DP0047.06 | 28 | 60 | 47 | 0.0001 | Y |
| DP0047.12 | 32 | 60 | 53 | 0.0000 | Y |
| DP0047.15 | 26 | 60 | 43 | 0.0005 | Y |
| DP0047.17 | 27 | 60 | 45 | 0.0002 | Y |
| DP0047.19 | 26 | 60 | 43 | 0.0005 | Y |
| DP0047.23 | 23 | 60 | 38 | 0.0038 | Y |
| DP0047.25 | 30 | 60 | 50 | 0.0000 | Y |
| ZH11-TC | 34 | 180 | 19 | | |

In the second experiment, the same ten lines were tested. After paraquat solution treated, 381 of the 600 (64%) OsDN-LNP1 transgenic rice kept green and showed tolerant phenotype, whereas 100 of the 180 (56%) ZH11-TC seedlings showed tolerance phenotype. The tolerance rate of OsDN-LNP1 transgenic rice was significantly greater than ZH11-TC (P value=0.0209) seedlings.

Analysis at transgenic line level was shown in Table 31. Six lines exhibited greater tolerance rates than ZH11-TC control, and four lines showed significantly greater tolerance rates than ZH11-TC seedlings. In the two experiments, many lines exhibited better paraquat tolerance. These results clearly demonstrate that OsDN-LNP1 had enhanced paraquat tolerance or antioxidative ability of transgenic plants.

TABLE 31

Paraquat tolerance assay of OsDN-LNP1 transgenic rice plants at transgenic line level (2nd experiment)

| Line ID | Number of tolerant seedlings | Number of total seedlings | Tolerance rate (%) | P value | P ≤ 0.05 |
|---|---|---|---|---|---|
| DP0047.01 | 43 | 60 | 72 | 0.0331 | Y |
| DP0047.03 | 32 | 60 | 53 | 0.7658 | |
| DP0047.05 | 28 | 60 | 47 | 0.2379 | |
| DP0047.06 | 35 | 60 | 58 | 0.7085 | |
| DP0047.12 | 44 | 60 | 73 | 0.0193 | Y |
| DP0047.15 | 28 | 60 | 47 | 0.2379 | |
| DP0047.17 | 50 | 60 | 83 | 0.0005 | Y |
| DP0047.19 | 36 | 60 | 60 | 0.5499 | |
| DP0047.23 | 31 | 60 | 52 | 0.6027 | |
| DP0047.25 | 54 | 60 | 90 | 0.0000 | Y |
| ZH11-TC | 100 | 180 | 56 | | |

Example 8

Field Drought Assay of Mature Transgenic Rice Plants

Flowering stage drought stress is an important problem in agriculture practice. The transgenic rice plants were further tested under field drought conditions. For the Field drought assays of mature rice plants, 12 transgenic lines of each gene construct were tested. The $T_2$ seeds were first sterilized as described in Example 4. The germinated seeds were planted in a seedbed field. At 3-leaf stage, the seedlings were transplanted into the testing field, with 4 replicates and 10 plants per replicate for each transgenic line, and the 4 replicates were planted in the same block. ZH11-TC and DP0158 were nearby the transgenic lines in the same block, and were used as controls in the statistical analysis.

The rice plants were managed by normal practice using pesticides and fertilizers. Watering was stopped at the tillering stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and/or drought tolerance. Special attention was paid to leaf rolling degree at noontime. At the end of the growing season, six representative plants of each transgenic line were harvested from the middle of the row per line, and grain weight per plant was measured. The grain weight data were statistically analyzed using mixed linear model. Positive transgenic lines were selected based on the analysis (P≤0.1).

Figure 3:
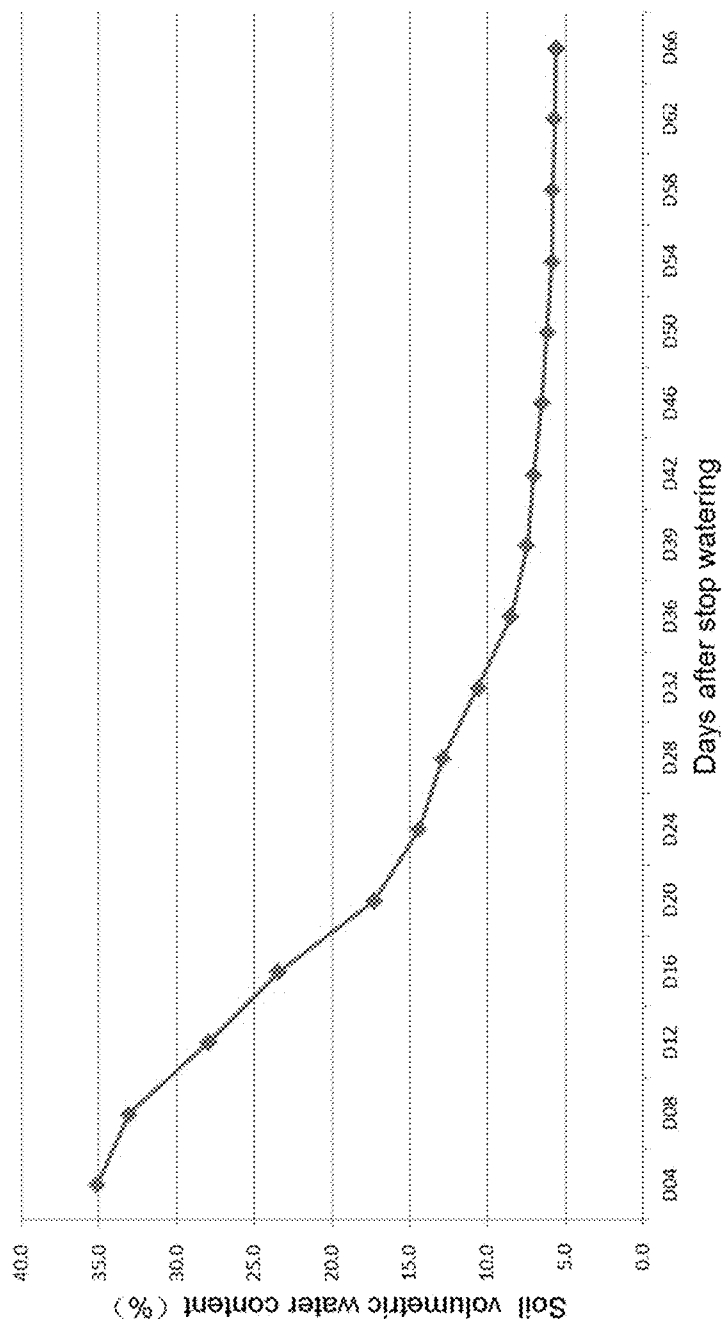
FIG. 3 shows changes of soil volumetric water content at different developmental stage for drought testing OsDN-LNP1 transgenic rice. The OsDN-LNP1 transgenic rice started heading at 37 days after stopping watering.

Field Drought Assay Results:

Twelve OsDN-LNP2 transgenic lines were tested in Hainan Province in the first experiment, ZH11-TC and DP0158 rice plants planted nearby were used as control. Watering was stopped from panicle initiation stage II-III to seed maturity to produce heavier drought stress. The soil volumetric moisture content decreased from 35% to 5% during heading and maturation stage (FIG. 3). Drought stress appeared after 20 days without water, and the rice leaves curled. During this drought stress, DP0047.19 rice plants showed greener leaf color and less leaf curl degree than ZH11-TC and DP0158 controls at vegetative stage. 37 days after stopping watering, 50% of transgenic rice and ZH11-TC and DP0158 rice plants started heading, and the leaf roll degree increased. DP0047.12, DP0047.19, DP0047.20, DP0047.25 and DP0047.26 showed better seed setting rates at maturation stage.

At the end of the planting season, six representative plants of each transgenic line were harvested from the middle of the row per line, and grain weight per plant was measured. As shown in Table 32, the grain yield of OsDN-LNP1 transgenic rice was 7.13 g per plant, was more than that of DP0158 and less than that of ZH11-TC at construct level; four lines exhibited higher grain yield per plant than that of ZH11-TC and DP1058 controls. These results demonstrate that OsDN-LNP2 rice plant exhibited better drought tolerance at vegetative stage and better grain yield per plant than control after drought stress, and OsDN-LNP1 play a role in enhancing drought tolerance at vegetative stage and may improve the grain yield at maturation stage.

TABLE 32

Grain yield analysis of OsDN-LNP1 transgenic rice plants under field drought conditions

| Line ID | Number of survival plants | Number of harvested plants | Yield per plant (g) | CK = ZH11-TC diff | CK = ZH11-TC P value | CK = ZH11-TC P ≤ 0.1 | CK = DP0158 diff | CK = DP0158 P value | CK = DP0158 P ≤ 0.1 |
|---|---|---|---|---|---|---|---|---|---|
| DP0047.01 | 40 | 24 | 7.01 | −0.72 | 0.360 | | 0.59 | 0.455 | |
| DP0047.03 | 38 | 24 | 7.52 | −0.21 | 0.788 | | 1.09 | 0.147 | |
| DP0047.12 | 40 | 24 | 8.52 | 0.79 | 0.311 | | 2.10 | 0.007 | Y |
| DP0047.15 | 40 | 24 | 6.28 | −1.45 | 0.064 | | −0.15 | 0.852 | |
| DP0047.16 | 39 | 24 | 7.19 | −0.54 | 0.476 | | 0.76 | 0.329 | |
| DP0047.17 | 40 | 24 | 5.48 | −2.24 | 0.004 | | −0.94 | 0.230 | |
| DP0047.19 | 40 | 24 | 6.55 | −1.18 | 0.121 | | 0.12 | 0.878 | |
| DP0047.20 | 40 | 24 | 8.08 | 0.35 | 0.654 | | 1.65 | 0.035 | Y |
| DP0047.22 | 39 | 24 | 7.23 | −0.50 | 0.523 | | 0.80 | 0.293 | |
| DP0047.23 | 40 | 24 | 7.89 | 0.16 | 0.840 | | 1.46 | 0.062 | Y |
| DP0047.25 | 40 | 24 | 5.81 | −1.92 | 0.013 | | −0.61 | 0.417 | |
| DP0047.26 | 38 | 24 | 7.98 | 0.25 | 0.728 | | 1.56 | 0.037 | Y |
| ZH11-TC | 40 | 24 | 7.73 | | | | | | |
| DP0158 | 39 | 24 | 6.43 | | | | | | |
| DP0047 (construct) | | | 7.13 | −0.60 | 0.396 | | 0.70 | 0.320 | |

Example 9

Transformation and Evaluation of Maize with Rice Low Nitrogen Tolerance Genes Maize plants can be transformed to over-express *Oryza sativa* low nitrogen tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as $T_1$ plants, can be subjected to a low nitrogen stress. Using image analysis, plant area, volume, growth rate and color can be measured at multiple times before and during low nitrogen stress. Significant delay in leaf area reduction, a reduced yellow-color accumulation, and/or an increased growth rate during low nitrogen stress, relative to a control, will be considered evidence that the gene functions in maize to enhance NUE.

Example 10

Transformation and Evaluation of Gaspe Flint Derived Maize Lines

As described in Example 7, maize plants can be transformed to over-express the rice low nitrogen tolerance genes, or corresponding homologs from another species. In certain circumstances, recipient plant cells can be from a uniform maize line which having a short life cycle ("fast cycling"), a reduced size, and high transformation potential, and are disclosed in Tomes et al. U.S. Pat. No. 7,928,287.

The population of transgenic ($T_0$) plants resulting from the transformed maize embryos can be grown in a controlled greenhouse environment using a modified randomized block design to reduce or eliminate environmental error. For example, a group of 30 plants, comprising 24 transformed experimental plants and 6 control plants (collectively, a "replicate group"), are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of 30 plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

Each plant in the line population is identified and tracked throughout the evaluation process, and the data gathered from that plant are automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor (U.S. Pat. Nos. 7,403,855 and 7,702,462).

Each greenhouse plant in the $T_0$ line population, including any control plants, is analyzed for agronomic characteristics of interest, and the agronomic data for each plant are recorded or stored in a manner so as to be associated with the identifying data for that plant. Confirmation of a phenotype (gene effect) can be accomplished in the $T_1$ generation with a similar experimental design to that described above.

Example 11

Laboratory NUE Screening of Rice Low Nitrogen Tolerance Genes in *Arabidopsis*

To understand whether rice low nitrogen tolerance genes can improve dicot plants' low nitrogen tolerance, or other traits, rice low nitrogen tolerance gene over-expression vectors were transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

A 16.8-kb T-DNA based binary vector (SEQ ID NO: 2) which is called pBC-yellow was used in this experiment. This vector contains the RD29a promoter driving expression of the gene for ZS-Yellow, which confers yellow fluorescence to transformed seed. The OsDN-PPR1 and OsRRM1 gene were cloned as described in Example 1, and constructed in the Gateway vector. Then using the INVITROGEN™ GATEWAY® technology, an LR Recombination Reaction was performed on the entry clone containing the directionally cloned PCR product and the pBC-yellow vector to generate GWD0039 and GWD0049 vectors. In these vectors, OsDN-PPR1 and OsRRM1 gene were driven by constitutive promoter CaMV 35S.

Growth Chamber NUE Screening Method:

The $T_1$ generation fluorescent seeds were selected, surface sterilized and stratified in the dark at 4° C. for three days. Then 32 $T_1$ individuals were sown next to 32 empty vector control (pBCyellow-empty vector) individuals on one low nitrogen media containing 0.5× N-Free Hoagland's, 0.4 mM potassium nitrate, 0.1% sucrose, 1 mM MES and 0.25% Phytagel™ as shown in Table 33. Two repeats were prepared. The plates were horizontally placed in the growth chamber and cultured for a period of 10 days at 22° C., 60% relative humidity and a 16 hour day cycle. Seedling status was evaluated by imaging the entire plate from 10-13 days after stratifications.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin was shown by dose-response studies to be an indicator of nitrogen assimilation (patent application US20110209245).

The images were analyzed using Nitrosight software and the number of Pixel (for size of the plants) and the intensity of Bin2 (for green color of leaves) for each of the 32/64 transgenic seedlings were compared with 32/64 seedlings of empty vector control for similar parameters. The green color and better growth of the seedling as compared to the empty vector control seedling signifies improved NUE. The data was statistically analyzed and a gene was considered as a weak validation with a P value less than $10^{-4}$ and a strong validation at $10^{-5}$ for Bin2 and Area in replicates and multiple days (Day 10 to Day 13 of assay). In this experiment the statement regarding a positive response being less than $10^{-3}$ holds.

TABLE 33

Modified Hoagland's nutrient solution for culturing *Arabidopsis*

| Molecular formula | Molecular weight | Concentration (mM) |
|---|---|---|
| $KNO_3$ | 101.1 | 0.4 |
| $MgSO_4 \cdot 7H_2O$ | 246.49 | 1.0 |
| $CaCl_2$ | 110.98 | 2.5 |
| $Na_2HPO_4$ | 141.96 | 1.0 |
| $K_2SO_4$ | 174.26 | 1.3 |
| Fe-EDTA | 367.1 | $4.6 \times 10^{-3}$ |
| MES | 195.2 | 1.0 |
| $H_3BO_3$ | 61.84 | $12.5 \times 10^{-3}$ |
| $MnSO_4 \cdot H_2O$ | 169.01 | $1.0 \times 10^{-3}$ |
| $ZnSO_4 \cdot 7H_2O$ | 287.5 | $1.0 \times 10^{-3}$ |
| $CuSO_4 \cdot 5H_2O$ | 249.71 | $0.25 \times 10^{-3}$ |
| $Na_2MoO_4 \cdot 2H_2O$ | 241.95 | $0.25 \times 10^{-3}$ |

Growth Chamber NUE Screening Results:

1) As shown in Table 34, the P values of the transgenic *Arabidopsis*' area were lower than $10^{-3}$ at $10^{th}$ day in both repeats, and at $11^{th}$ day in one repeat after stratifications, and the P value of the transgenic plants' greenness was lower than $10^{-3}$ at $12^{th}$ day. The growth status of the OsDN-PPR1 transgenic *Arabidopsis* was better than the empty vector transformed *Arabidopsis*. These results indicate the OsDN-PPR1 transgenic *Arabidopsis* grew better than the control in low nitrogen medium. Over-expression of OsDN-PPR1 under CaMV 35S increased the low nitrogen tolerance or NUE of a dicot plants.

Over-expression of OsDN-PPR1 increased low nitrogen tolerance or NUE and also increased the chlorate sensitivity of transgenic rice as described in Example 5 and 6. This cross-validation further indicates that a monocot gene (OsDN-PPR1 from rice) can function in a dicot plant (*Arabidopsis*).

TABLE 34

P values for green leaf area and greenness evaluated for the over-expression OsDN-PPR1 on 4 consecutive days under low nitrogen condition

| | $10^{th}$ Day | | $11^{th}$ Day | | $12^{th}$ Day | | $13^{th}$ Day | |
|---|---|---|---|---|---|---|---|---|
| Plate # | Bin2-p-value | Area-p-value | Bin2-p-value | Area-p-value | Bin2-p-value | Area-p-value | Bin2-p-value | Area-p-value |
| a | 8.57E−01 | 1.49E−03 | 9.66E−01 | 6.61E−04 | 9.01E−01 | 1.42E−01 | 3.88E−02 | 2.33E−01 |
| b | 2.83E−01 | 4.49E−03 | 6.99E−02 | 1.09E−02 | 1.28E−03 | 6.92E−02 | 9.52E−01 | 7.33E−02 |

2) the P values of OsRRM1-transgenic *Arabidopsis* area were lower than $10^{-3}$ at $11^{th}$ day one repeat after stratifications, and the P value of the transgenic plants' greenness was lower than $10^{-3}$ at $10^{th}$ and $11^{th}$ day in both repeat and was lower than $10^{-3}$ at $12^{th}$ and $13^{th}$ in one repeat (Table 35), indicating the OsRRM1 transgenic *Arabidopsis* grew better than the control in low nitrogen medium. Over-expression of OsRRM1 under CaMV 35S increased the low nitrogen tolerance or NUE of a dicot plants. Over-expression of OsRRM1 increased low nitrogen tolerance or NUE and also increased the chlorate sensitivity of transgenic rice as described in Example 5 and 6. This cross-validation further indicates that a monocot gene (OsRRM1 from rice) can function in a dicot plant (*Arabidopsis*).

TABLE 35

P values for green leaf area and greenness evaluated for the over expression OsRRM1 on 4 consecutive days under low nitrogen condition

| | $10^{th}$ Day | | $11^{th}$ Day | | $12^{th}$ Day | | $13^{th}$ Day | |
|---|---|---|---|---|---|---|---|---|
| Plate # | Bin2-p-value | Area-p-value | Bin2-p-value | Area-p-value | Bin2-p-value | Area-p-value | Bin2-p-value | Area-p-value |
| a | 1.46E−07 | 8.76E−03 | 2.78E−04 | 1.57E−02 | 4.61E−07 | 2.72E−02 | 1.84E−01 | 3.09E−02 |
| b | 2.28E−03 | 5.25E−02 | 2.71E−04 | 2.48E−02 | 2.11E−02 | 1.70E−02 | 8.53E−03 | 1.89E−02 |

What is claimed is:

1. A method of increasing nitrogen stress tolerance in a plant, comprising:

(a) expressing a polynucleotide in a plant cell, wherein the polynucleotide encodes a polypeptide having an amino acid sequence of at least 95% sequence identity when compared to SEQ ID NO: 12 and wherein the polynucleotide is under the control of a heterologous regulatory element; and (b) obtaining a plant from the plant cell, wherein said plant exhibits increased nitrogen stress tolerance when compared to a control plant not comprising the heterologous regulatory element.

2. The method of claim 1, wherein the progeny plant exhibits increased yield.

3. The method of claim 1, wherein the plant is rice or maize.

4. The method of claim 1, wherein the heterologous regulatory element is a promoter.

* * * * *